US012215325B2

(12) United States Patent
Xu et al.

(10) Patent No.: US 12,215,325 B2
(45) Date of Patent: Feb. 4, 2025

(54) XYLOSE METABOLIZING YEAST

(71) Applicant: BASF SE, Ludwigshafen am Rhein (DE)

(72) Inventors: Haowen Xu, Tarrytown, NY (US); Dominik Satory, Tarrytown, NY (US); Christopher Jackson, New York, NY (US)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 17/041,320

(22) PCT Filed: Mar. 27, 2019

(86) PCT No.: PCT/EP2019/057753
§ 371 (c)(1),
(2) Date: Sep. 24, 2020

(87) PCT Pub. No.: WO2019/185737
PCT Pub. Date: Oct. 3, 2019

(65) Prior Publication Data

US 2021/0017526 A1 Jan. 21, 2021

Related U.S. Application Data

(60) Provisional application No. 62/648,619, filed on Mar. 27, 2018.

(51) Int. Cl.

| | |
|---|---|
| ***C12N 15/52*** | (2006.01) |
| ***C12N 1/16*** | (2006.01) |
| ***C12N 1/18*** | (2006.01) |
| ***C12N 9/92*** | (2006.01) |
| ***C12P 7/10*** | (2006.01) |
| ***C12R 1/865*** | (2006.01) |

(52) U.S. Cl.
CPC ............... *C12N 15/52* (2013.01); *C12N 1/16* (2013.01); *C12N 9/92* (2013.01); *C12P 7/10* (2013.01); *C12N 1/185* (2021.05); *C12P 2203/00* (2013.01); *C12R 2001/865* (2021.05); *C12Y 503/01005* (2013.01)

(58) Field of Classification Search
CPC . C12N 15/52; C12N 1/16; C12N 9/92; C12N 1/185; C12N 15/81; C12N 9/1022; C12N 9/90; C12P 7/10; C12P 2203/00; C12P 7/06; C12R 2001/865; C12Y 502/01005; C12Y 202/01001; Y02E 50/10
See application file for complete search history.

(56) References Cited

U.S. PATENT DOCUMENTS 7,198,933 B2 * 4/2007 Zeikus ..................... C12N 9/92 536/23.4
7,998,722 B2 * 8/2011 Viitanen ................. C12P 7/065 435/320.1
8,404,472 B2 * 3/2013 Zucca ............ C12Y 101/03038 435/254.2
8,772,012 B2 * 7/2014 Katahira .................. C12N 9/90 536/23.1
9,605,269 B2 * 3/2017 Sillers ....................... C12P 7/28
9,701,972 B2 * 7/2017 Klaassen .................. C12N 9/92
10,093,922 B2 * 10/2018 Zieler ................ C12N 15/1027
10,400,244 B2 * 9/2019 Dragovic ............ C12N 15/113
10,450,588 B2 * 10/2019 Klaassen .............. C12N 9/1205
10,612,032 B2 * 4/2020 Harvey ................ C12N 15/635
10,619,174 B2 * 4/2020 Bremond ............ C12N 9/0006
10,689,670 B2 * 6/2020 Papapetridis ............. C12P 7/06
2013/0323822 A1 * 12/2013 Brevnova ...... C12Y 302/01004 435/254.21
2014/0162312 A1 * 6/2014 Klaassen ............. C12N 15/815 435/47
2014/0186884 A1 * 7/2014 Nunn, Jr. .................. C12P 7/40 435/254.6
2014/0377813 A1 * 12/2014 Dragovic ................ C12P 35/00 435/119
2016/0002674 A1 1/2016 Onishi et al.
2019/0316111 A1 * 10/2019 Thevelein ............ C12P 7/6409

(Continued)

FOREIGN PATENT DOCUMENTS

WO 03062387 A2 7/2003
WO 2010001363 A1 1/2010
WO 2013017644 A1 2/2013

(Continued)

OTHER PUBLICATIONS

UniProt Accession No. XYLA_THENN, published Jul. 28, 2009 (Year: 2009).*
Geneseq Accession No. AXR32122, published Nov. 26, 2009 (Year: 2009).*
Demeke et al., Development of a D-xylose fermenting and inhibitor tolerant industrial *Saccharomyces cerevisiae* strain with high performance in lignocellulose hydrolysates using metabolic and evolutionary engineering. Biotechnol. Biofuels., 2013, vol. 6:89, pp. 1-24. (Year: 2013).*
International Search Report and Written Opinion for corresponding PCT/EP2019/057753 mailed Aug. 13, 2019, 22 pages.
Verhoeven M. D. et al, "Mutations in PMR1 stimulate xylose isomerase activity and anaerobic growth on xylose of engineered *Saccharomyces cerevisiae* by influencing manganese homeostasis", Scientific Reports,vol. 7, No. 1, Apr. 12, 2017.
Kwak S. et al, "Production of fuels and chemicals from xylose by engineered *Saccharomyces cerevisiae*: a review and perspective", Microbial Cell Factories, vol. 16, May 11, 2017.
Feng Q. et al, "Signature pathway expression of xylose utilization in the genetically engineered industrial yeast *Saccharomyces cerevisiae*", PLOS ONE, vol. 13(4):e0195633, Apr. 5, 2018.

(Continued)

*Primary Examiner* — Ganapathirama Raghu
(74) *Attorney, Agent, or Firm* — Armstrong Teasdale LLP

(57) ABSTRACT

Described herein are microorganisms, in particular yeast, which have been transformed with one or more expression construct(s) for i) the overexpression of the native genes encoding xylulose kinase (XKS1), transaldolase (TAL1), transketolase 1 (TKL1) and transketolase 2 (TKL2) and ii) the expression of a functional heterologous gene encoding a xylose isomerase (XI), where the xylose isomerase (XI) gene is derived from a microorganism selected from the group consisting of *T. neapolitana, A. andensis* and *C. clariflavum*. Also described herein are expression constructs, methods for fermenting pentose sugars using the microorganisms and methods for producing such microorganisms.

7 Claims, 12 Drawing Sheets

Specification includes a Sequence Listing.

(56) References Cited

U.S. PATENT DOCUMENTS

2021/0017526 A1* 1/2021 Xu ......................... C12N 15/52

FOREIGN PATENT DOCUMENTS

WO 2016062821 A1 4/2016
WO 2017164388 A1 9/2017

OTHER PUBLICATIONS

Bracher J.M. et al, "Reassessment of requirements for anaerobic xylose fermentation by engineered, non-evolved *Saccharomyces cerevisiae* strains", Fems Yeast Research, Sep. 24, 2018.
Vieille C. et al, "XyIA cloning and sequencing and biochemical characterization of xylose isomerase from Thermotoga neapolitana", Applied and Environmental Microbiology, vol. 61, No. 5, May 1, 1995.

* cited by examiner

SEQUENCE LISTING

<160> NUMBER OF SEQ ID NOS: 94

<210> SEQ ID NO 1
<211> LENGTH: 1320
<212> TYPE: DNA
<213> ORGANISM: Thermonanaerobacterium xylanolyticum

<400> SEQUENCE: 1

```
atgaataaat attttgagaa cgtatctaaa ataaaatatg aaggaccaaa atcaaacaat     60

ccttattctt ttaaatttta caatcctgag gaagtaatcg atggtaagac gatggaggag    120

catcttcgct tttctatagc ttattggcac acttttactg ctgatggaac agatcaattt    180

ggcaaagcta ccatgcaaag gccatggaat cactatacag atcctatgga catagctaaa    240

gcaagggtag aggcagcatt tgagtttttt gataagataa atgcaccgta tttctgcttc    300

catgatagag atattgcccc tgaaggagac actcttagag agacgaacaa aaatttagat    360

acaatagttg ctatgataaa ggattacttg aagaccagca agacgaaagt tttgtggggt    420

actgcgaatc ttttctccaa tccaagattt gtgcatggtg catcaacgtc ttgcaatgcc    480

gatgttttcg catattctgc atcacaagtc aaaaaagcac ttgagattac taaggagctt    540

ggtggcgaaa actacgtatt ctggggtgga agagaaggat atgagacact tctcaataca    600

gatatggagt ttgagcttga taattttgca agatttttgc acatggctgt tgattatgca    660

aaggaaatcg gctttgaagg ccagctcttg attgagccga agccaaagga gcctacaaag    720

catcaatacg actttgacgt ggcaaatgta ttggcattct tgagaaaata cgatcttgac    780

aaatatttca aagttaatat cgaagcaaat catgcaacat tagcattcca tgatttccag    840

catgagctaa gatacgccag aataaacggt gtattaggat cgattgacgc aaatacaggt    900

gatatgctat taggctggga tacagatcag ttccctacag atatacgcat gacaacactt    960

gctatgtatg aagtcataaa gatgggcgga tttgacaaag gtggactcaa tttcgatgcg   1020

aaagtaagac gtgcttcatt tgagccagaa gatcttttct tgggtcacat agcaggaatg   1080

gatgcttttg caaaaggctt caaagtggct tacaagcttg taaaagatgg cgtttttgac   1140

aagttcatcg aggaaagata tgcaagctac aaagatggca taggtgcaga tattgtaagt   1200

ggaaaagctg attttagaag ccttgagaag tacgcattag agcacagcca gattgtcaac   1260

aaatcaggaa gacaagagct attagaatca atcctaaatc agtatttgtt tgcagaataa   1320
```

<210> SEQ ID NO 2
<211> LENGTH: 439
<212> TYPE: PRT
<213> ORGANISM: Thermonanaerobacterium xylanolyticum

<400> SEQUENCE: 2

```
Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95
```

-continued

```
Tyr Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Trp Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ser Gln Val Lys Lys Ala Leu Glu Ile
                165                 170                 175

Thr Lys Glu Leu Gly Gly Glu Asn Tyr Val Phe Trp Gly Gly Arg Glu
            180                 185                 190

Gly Tyr Glu Thr Leu Leu Asn Thr Asp Met Glu Phe Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Leu Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Thr Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Asp Gly Ile Gly Ala Asp Ile Val Ser
385                 390                 395                 400

Gly Lys Ala Asp Phe Arg Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435
```

<210> SEQ ID NO 3
<211> LENGTH: 1320
<212> TYPE: DNA
<213> ORGANISM: Pseudobacteroides cellulosolvens

<400> SEQUENCE: 3

```
atgtcagaat tttttagtaa tgtttcaaag attcaatatg aaggtaagaa ctctgataat      60

ccattggctt ttaagtatta taacccagat gaggttatag gcggaaagac aatgaaggat     120
```

```
catttgagat tcgcagttgc ttactggcat acattccagg gaacaggcgg agatccattc    180

ggacctggta cagcagtaag accatgggac aatataacag atccaatgga acttgctaaa    240

gcaaaagtag ctgcaaactt cgagttctgt gaaaaattag gtgtaccgtt ctactgtttc    300

catgacaggg atatagcacc tgaagcttca actcttagag aaacaaataa gagacttgat    360

gaaatagttg ctcttatgaa ggaatatatg aaaaccagca gtgttaagct cctctgggga    420

actacaaatg cattcggtaa cccaagattt gtacacggtg cttcaacatc accaaatgcc    480

gatgtttttg catttgcagc agctcaggtt aaaaaagcaa tggaaataac tttagagctt    540

ggcggacaga actatgtatt ctggggtgga agagaaggtt atgagaccct attaaacaca    600

gacatgaagc ttgagcttga caacatggga agattcttaa gaatggctgt tgattacgca    660

aaagaaatag gctttaaagg acaattcctc attgaaccaa agccgaagga acctacaaaa    720

caccagtatg atttcgatac agctacagtt gttggtttct taagagctca tggtcttgaa    780

aacgatttca agatgaacat agaagcaaac catgctaccc ttgctgctca taccttccag    840

catgaagtat atactgcaag agtaaacaat gtattcggaa gtattgatgc aaatcaggga    900

gacttgctct taggatggga tacagaccaa ttcccaacta atatttatga tacaacactt    960

tgcatgtatg aagttcttaa agcaggcggt ttcacaaccg gcggattaaa cttcgactct   1020

aaagtaagaa gaggttcatt tgagccaatc gatcttttct atgcacatat tgcaggaatg   1080

gatgcttttg ctaagggtct taagattgct tacaagatgg tttcagaagg caagttcgat   1140

aaagttattg aagaccgtta tgcaagctac aaaagcggta ttggtagcga tatagttaat   1200

ggaaaagttg gatttaaaga attggaaaaa tatgcattgg agcatgatca ggttaagaac   1260

gtatcaggaa gacaggaagt tcttgaaagc atgctgaaca agtatatttt agaagattaa   1320
```

```
<210> SEQ ID NO 4
<211> LENGTH: 439
<212> TYPE: PRT
<213> ORGANISM: Pseudobacteroides cellulosolvens

<400> SEQUENCE: 4

Met Ser Glu Phe Phe Ser Asn Val Ser Lys Ile Gln Tyr Glu Gly Lys
1               5                   10                  15

Asn Ser Asp Asn Pro Leu Ala Phe Lys Tyr Tyr Asn Pro Asp Glu Val
            20                  25                  30

Ile Gly Gly Lys Thr Met Lys Asp His Leu Arg Phe Ala Val Ala Tyr
        35                  40                  45

Trp His Thr Phe Gln Gly Thr Gly Gly Asp Pro Phe Gly Pro Gly Thr
    50                  55                  60

Ala Val Arg Pro Trp Asp Asn Ile Thr Asp Pro Met Glu Leu Ala Lys
65                  70                  75                  80

Ala Lys Val Ala Ala Asn Phe Glu Phe Cys Glu Lys Leu Gly Val Pro
                85                  90                  95

Phe Tyr Cys Phe His Asp Arg Asp Ile Ala Pro Glu Ala Ser Thr Leu
            100                 105                 110

Arg Glu Thr Asn Lys Arg Leu Asp Glu Ile Val Ala Leu Met Lys Glu
        115                 120                 125

Tyr Met Lys Thr Ser Ser Val Lys Leu Leu Trp Gly Thr Thr Asn Ala
    130                 135                 140

Phe Gly Asn Pro Arg Phe Val His Gly Ala Ser Thr Ser Pro Asn Ala
145                 150                 155                 160

Asp Val Phe Ala Phe Ala Ala Ala Gln Val Lys Lys Ala Met Glu Ile
```

-continued

```
                165                 170                 175

Thr Leu Glu Leu Gly Gly Gln Asn Tyr Val Phe Trp Gly Gly Arg Glu
            180                 185                 190

Gly Tyr Glu Thr Leu Leu Asn Thr Asp Met Lys Leu Glu Leu Asp Asn
        195                 200                 205

Met Gly Arg Phe Leu Arg Met Ala Val Asp Tyr Ala Lys Glu Ile Gly
    210                 215                 220

Phe Lys Gly Gln Phe Leu Ile Glu Pro Lys Pro Lys Glu Pro Thr Lys
225                 230                 235                 240

His Gln Tyr Asp Phe Asp Thr Ala Thr Val Val Gly Phe Leu Arg Ala
                245                 250                 255

His Gly Leu Glu Asn Asp Phe Lys Met Asn Ile Glu Ala Asn His Ala
            260                 265                 270

Thr Leu Ala Ala His Thr Phe Gln His Glu Val Tyr Thr Ala Arg Val
        275                 280                 285

Asn Asn Val Phe Gly Ser Ile Asp Ala Asn Gln Gly Asp Leu Leu Leu
    290                 295                 300

Gly Trp Asp Thr Asp Gln Phe Pro Thr Asn Ile Tyr Asp Thr Thr Leu
305                 310                 315                 320

Cys Met Tyr Glu Val Leu Lys Ala Gly Gly Phe Thr Thr Gly Gly Leu
                325                 330                 335

Asn Phe Asp Ser Lys Val Arg Arg Gly Ser Phe Glu Pro Ile Asp Leu
            340                 345                 350

Phe Tyr Ala His Ile Ala Gly Met Asp Ala Phe Ala Lys Gly Leu Lys
        355                 360                 365

Ile Ala Tyr Lys Met Val Ser Glu Gly Lys Phe Asp Lys Val Ile Glu
    370                 375                 380

Asp Arg Tyr Ala Ser Tyr Lys Ser Gly Ile Gly Ser Asp Ile Val Asn
385                 390                 395                 400

Gly Lys Val Gly Phe Lys Glu Leu Glu Lys Tyr Ala Leu Glu His Asp
                405                 410                 415

Gln Val Lys Asn Val Ser Gly Arg Gln Glu Val Leu Glu Ser Met Leu
            420                 425                 430

Asn Lys Tyr Ile Leu Glu Asp
        435
```

<210> SEQ ID NO 5
<211> LENGTH: 770
<212> TYPE: DNA
<213> ORGANISM: Anditalea andensis

<400> SEQUENCE: 5

```
atgtctaaaa cctattttcc atcaattgaa aaaattaaat tcgaaggaag ggattccaaa     60

aatccttttg ctttcaaatt ttacgatgaa aaccgtgtag taggggggtaa aagcatgaag    120

gagcacttca agtttgccat cgcatactgg cattcattca atgccaaagg ggatgatcct    180

tttggtccag gaaccaaaac ttttgaatgg gatgagtcat ccgatgctgt tcagagagcc    240

aaagataaaa tggatgctgc atttgaattt attcaaaaga taggagcacc atattactgc    300

ttccatgatg tggatctggt agatgaaggt gattctatag aggaatatga aagaaggatg    360

aaggccatag tcgagtatgc taagcaaaag cagcaagata ctggtatcaa gcttctttgg    420

ggcacagcca atgttttcag taacccacgt tatatgaatg gtgcttcgac taaccccgat    480

tttaatgtag tttcatgggc agctactcaa gttaagaatt ctattgatgc tactatagcc    540
```

```
ctaggtgggg aaaactatgt attctggggt ggaagagaag gatatatgtc tttactcaat    600

accgatatga aacgagaaac agaacattta gctcagtttc ttaccatggc gcgggattat    660

gcgcgtcagc agggttttaa aggtaatttc cttatagagc caaaaccaat ggagcctacc    720

aaacaccagt atgatttcga ttctgctacg gtagccggtt ttctaagact               770


<210> SEQ ID NO 6
<211> LENGTH: 437
<212> TYPE: PRT
<213> ORGANISM: Anditalea andensis

<400> SEQUENCE: 6

Met Ser Lys Thr Tyr Phe Pro Ser Ile Glu Lys Ile Lys Phe Glu Gly
1               5                   10                  15

Arg Asp Ser Lys Asn Pro Phe Ala Phe Lys Phe Tyr Asp Glu Asn Arg
            20                  25                  30

Val Val Gly Gly Lys Ser Met Lys Glu His Phe Lys Phe Ala Ile Ala
        35                  40                  45

Tyr Trp His Ser Phe Asn Ala Lys Gly Asp Asp Pro Phe Gly Pro Gly
    50                  55                  60

Thr Lys Thr Phe Glu Trp Asp Glu Ser Ser Asp Ala Val Gln Arg Ala
65                  70                  75                  80

Lys Asp Lys Met Asp Ala Ala Phe Glu Phe Ile Gln Lys Ile Gly Ala
                85                  90                  95

Pro Tyr Tyr Cys Phe His Asp Val Asp Leu Val Asp Glu Gly Asp Ser
            100                 105                 110

Ile Glu Glu Tyr Glu Arg Arg Met Lys Ala Ile Val Glu Tyr Ala Lys
        115                 120                 125

Gln Lys Gln Gln Asp Thr Gly Ile Lys Leu Leu Trp Gly Thr Ala Asn
    130                 135                 140

Val Phe Ser Asn Pro Arg Tyr Met Asn Gly Ala Ser Thr Asn Pro Asp
145                 150                 155                 160

Phe Asn Val Val Ser Trp Ala Ala Thr Gln Val Lys Asn Ser Ile Asp
                165                 170                 175

Ala Thr Ile Ala Leu Gly Gly Glu Asn Tyr Val Phe Trp Gly Gly Arg
            180                 185                 190

Glu Gly Tyr Met Ser Leu Leu Asn Thr Asp Met Lys Arg Glu Thr Glu
        195                 200                 205

His Leu Ala Gln Phe Leu Thr Met Ala Arg Asp Tyr Ala Arg Gln Gln
    210                 215                 220

Gly Phe Lys Gly Asn Phe Leu Ile Glu Pro Lys Pro Met Glu Pro Thr
225                 230                 235                 240

Lys His Gln Tyr Asp Phe Asp Ser Ala Thr Val Ala Gly Phe Leu Arg
                245                 250                 255

Leu Tyr Gly Leu Asp Lys Asp Phe Lys Leu Asn Ile Glu Val Asn His
            260                 265                 270

Ala Thr Leu Ala Gly His Thr Phe Gln His Glu Leu Gln Val Ala Ala
        275                 280                 285

Asp Ala Gly Met Leu Gly Ser Ile Asp Ala Asn Arg Gly Asp Tyr Gln
    290                 295                 300

Asn Gly Trp Asp Thr Asp Gln Phe Ala Leu Asn Leu Gln Glu Leu Thr
305                 310                 315                 320

Glu Ala Met Leu Val Ile Leu Glu Ala Gly Gly Ile Gln Gly Gly Gly
                325                 330                 335
```

```
Val Asn Phe Asp Ala Lys Leu Arg Arg Asn Ser Thr Asp Leu Glu Asp
            340                 345                 350

Leu Phe His Ala His Ile Gly Ser Met Asp Ala Phe Ala Arg Ala Leu
        355                 360                 365

Leu Ile Ala Gln Asp Ile Leu Asp Asn Ser Asp Tyr Arg Ala Met Arg
    370                 375                 380

Lys Ala Arg Tyr Ala Ser Phe Asp Glu Gly Lys Gly Lys Glu Phe Glu
385                 390                 395                 400

Ser Gly Lys Leu Thr Leu Glu Asp Leu Arg Glu His Ala Leu Ala Thr
                405                 410                 415

Gly Glu Pro Lys Ser Ile Ser Gly Arg Gln Glu Met Tyr Glu Asn Leu
            420                 425                 430

Leu Asn Gln Phe Ile
        435


<210> SEQ ID NO 7
<211> LENGTH: 1317
<212> TYPE: DNA
<213> ORGANISM: Algibacter lectus

<400> SEQUENCE: 7

atggctacta aagaatattt taaaggcatt agcaacatta aatttgaagg taaggaatct     60

gataatccat tagcattcaa atattacaat ccggaccagg ttgtagcagg aaaaaccatg    120

aaagaatggt ttaaattttc aattgcttac tggcatacat tctgtgggca aggtggagat    180

ccatttggtc caggaacaca aagttttgag tgggataaat catcagatcc aattcaagcg    240

gcaaaagata aagccgatgc agctttcgaa tttattggaa aaatgggatt cgattatttc    300

tgtttccacg atttcgattt aattcaagaa ggtgcaacat ttgcagagtc agaaagtaga    360

ttagagacta tcacagatta cataaaaggt aaacaagccg aaagtggtgt aaaattactt    420

tggggaacag caaactgttt ttctaaccca cgttacatga atggtgcttc tacaaatcca    480

gatttcgatg tggtagctag agcaggcgga caagtaaaat tagctttaga tgcgactatt    540

aaattaggtg gtgaaaacta cgtattctgg ggaggtcgtg aaggttacat gtctttatta    600

aatactgata tggggcgtga attagatcac atggggcaat ttttaaccat ggctagagat    660

tacgcaagag ctcaaggttt taaaggaaac ttttttatcg agcctaagcc aatggagcca    720

tctaaacacc aatacgattt cgattcggct acagctatcg gtttcttaag agaatatggt    780

ttagataaag atttcaaaat aaacatagaa gtaaaccatg ctacattagc acaacatacg    840

ttccaacacg aaattgaaac ggctgcaaaa gctggtatgt taggtagctt agatgctaac    900

cgtggcgatt accaaaatgg ttgggatacc gatcaattcc caaacaatat tcaagaaaca    960

acagaagcta tgttagtttt catgaaagct ggtggtttac aaggtggtgg tgttaatttc   1020

gatgctaaaa ttagaagaaa ctcaaccgat ttagacgatg ttttccatgc acatattggt   1080

ggagcagata cttttgctag agcattatta acagccgata aaattattac agattcagct   1140

tacgataaat tacgtaaaga gcgttacagt tctttcgatg ctggaaaagg taaagatttt   1200

gaagctggta aattaaactt acaagatttg tataaaattg ctcaagataa tggtgaactg   1260

caattacaaa gcggtaagca agaattgttt gagaatatta tcaatcagta tatctag      1317


<210> SEQ ID NO 8
<211> LENGTH: 438
<212> TYPE: PRT
<213> ORGANISM: Algibacter lectus
```

<400> SEQUENCE: 8

```
Met Ala Thr Lys Glu Tyr Phe Lys Gly Ile Ser Asn Ile Lys Phe Glu
1               5                   10                  15

Gly Lys Glu Ser Asp Asn Pro Leu Ala Phe Lys Tyr Tyr Asn Pro Asp
            20                  25                  30

Gln Val Val Ala Gly Lys Thr Met Lys Glu Trp Phe Lys Phe Ser Ile
        35                  40                  45

Ala Tyr Trp His Thr Phe Cys Gly Gln Gly Gly Asp Pro Phe Gly Pro
    50                  55                  60

Gly Thr Gln Ser Phe Glu Trp Asp Lys Ser Ser Asp Pro Ile Gln Ala
65                  70                  75                  80

Ala Lys Asp Lys Ala Asp Ala Ala Phe Glu Phe Ile Gly Lys Met Gly
                85                  90                  95

Phe Asp Tyr Phe Cys Phe His Asp Phe Asp Leu Ile Gln Glu Gly Ala
            100                 105                 110

Thr Phe Ala Glu Ser Glu Ser Arg Leu Glu Thr Ile Thr Asp Tyr Ile
        115                 120                 125

Lys Gly Lys Gln Ala Glu Ser Gly Val Lys Leu Leu Trp Gly Thr Ala
    130                 135                 140

Asn Cys Phe Ser Asn Pro Arg Tyr Met Asn Gly Ala Ser Thr Asn Pro
145                 150                 155                 160

Asp Phe Asp Val Val Ala Arg Ala Gly Gly Gln Val Lys Leu Ala Leu
                165                 170                 175

Asp Ala Thr Ile Lys Leu Gly Gly Glu Asn Tyr Val Phe Trp Gly Gly
            180                 185                 190

Arg Glu Gly Tyr Met Ser Leu Leu Asn Thr Asp Met Gly Arg Glu Leu
        195                 200                 205

Asp His Met Gly Gln Phe Leu Thr Met Ala Arg Asp Tyr Ala Arg Ala
    210                 215                 220

Gln Gly Phe Lys Gly Asn Phe Phe Ile Glu Pro Lys Pro Met Glu Pro
225                 230                 235                 240

Ser Lys His Gln Tyr Asp Phe Asp Ser Ala Thr Ala Ile Gly Phe Leu
                245                 250                 255

Arg Glu Tyr Gly Leu Asp Lys Asp Phe Lys Ile Asn Ile Glu Val Asn
            260                 265                 270

His Ala Thr Leu Ala Gln His Thr Phe Gln His Glu Ile Glu Thr Ala
        275                 280                 285

Ala Lys Ala Gly Met Leu Gly Ser Leu Asp Ala Asn Arg Gly Asp Tyr
    290                 295                 300

Gln Asn Gly Trp Asp Thr Asp Gln Phe Pro Asn Asn Ile Gln Glu Thr
305                 310                 315                 320

Thr Glu Ala Met Leu Val Phe Met Lys Ala Gly Gly Leu Gln Gly Gly
                325                 330                 335

Gly Val Asn Phe Asp Ala Lys Ile Arg Arg Asn Ser Thr Asp Leu Asp
            340                 345                 350

Asp Val Phe His Ala His Ile Gly Gly Ala Asp Thr Phe Ala Arg Ala
        355                 360                 365

Leu Leu Thr Ala Asp Lys Ile Ile Thr Asp Ser Ala Tyr Asp Lys Leu
    370                 375                 380

Arg Lys Glu Arg Tyr Ser Ser Phe Asp Ala Gly Lys Gly Lys Asp Phe
385                 390                 395                 400

Glu Ala Gly Lys Leu Asn Leu Gln Asp Leu Tyr Lys Ile Ala Gln Asp
                405                 410                 415
```

```
Asn Gly Glu Leu Gln Leu Gln Ser Gly Lys Gln Glu Leu Phe Glu Asn
            420                 425                 430

Ile Ile Asn Gln Tyr Ile
        435


<210> SEQ ID NO 9
<211> LENGTH: 1329
<212> TYPE: DNA
<213> ORGANISM: Epilithonimonas lactis

<400> SEQUENCE: 9

atggcaatta cgacaggaaa caaagagtac tttaaaggaa tagaaaaaat caagtttgag      60

ggaagagaat cagataatcc gttggcattc aaattttacg atgagaattt ggtcgttcgt     120

ggaaaaacga tgaaagaata tttcaagttt gcatctgctt actggcatac attctgcgca     180

actggtggag acccgtttgg tgcaggaact cagcaatttg actggttaac ggcttctgat     240

gcaaaacaga gagcaacaga aaaaatggat gccgctttcg aatttttcac caaattaggt     300

gttccttact actgtttcca cgattacgat ttgattgacg aggcagataa ctttacagaa     360

tctaccaaaa gactggaatt tattactgat tacgctaaag gaaagcaggc tgcttctggt     420

gtgaaactgc tttggggaac ttccaactgt ttctcaaacc caagatttat gaacggtgcg     480

gcaaccaatc cttcatttga cgttttggcg tacgcaggtg gacaggtgaa aaatgcttta     540

gatgctacga taaaattagg tggcgaaaac tatgtattct ggggcggccg tgaaggttat     600

atgtctttat taaacacgaa tatgaagcgt gagcaagagc acatggcgaa gtttttacat     660

ttggctaaag attacgcaag agctcaggga ttcaaaggaa ctttcttcat cgagccaaaa     720

ccgatggagc ctacaaaaca ccagtacgac ttcgatgctg cgacttgttt aaatttcctt     780

cgtcagtacg atttattgaa tgattttaaa ttaaatcttg aagttaatca cgctactttg     840

gctcaacata ctttcgagca cgaacttcag gtagctgcag ataacaatgt tttgggaagc     900

attgatgcga acagaggaga ttatcaaaac ggttgggata cagatcagtt cccggttgat     960

ttgtacgaaa tgactcaggc gatgttggtg attatccagg ctggaggttt ccagggcgga    1020

ggtgttaact ttgatgcaaa aatcagaaga aactcaaccg acctggaaga tattttcatc    1080

gctcacatca gcggaatgga caattttgca agatcgttcc tggctgctga taaaatttta    1140

gaaaaatcaa aatattctga gatcagaacc aacagatatt cttcgtttga ttctggaaaa    1200

ggtaaagatt tcgaaaacgg aagcttatct ttaacagatc ttgccactta tgctcaagga    1260

ttaggtgaag ttggaagaga gagcggaaag caggaatatc ttgagagtat tattaatcag    1320

tatttataa                                                            1329


<210> SEQ ID NO 10
<211> LENGTH: 442
<212> TYPE: PRT
<213> ORGANISM: Epilithonimonas lactis

<400> SEQUENCE: 10

Met Ala Ile Thr Thr Gly Asn Lys Glu Tyr Phe Lys Gly Ile Glu Lys
1               5                   10                  15

Ile Lys Phe Glu Gly Arg Glu Ser Asp Asn Pro Leu Ala Phe Lys Phe
            20                  25                  30

Tyr Asp Glu Asn Leu Val Val Arg Gly Lys Thr Met Lys Glu Tyr Phe
        35                  40                  45

Lys Phe Ala Ser Ala Tyr Trp His Thr Phe Cys Ala Thr Gly Gly Asp
```

```
    50                  55                  60

Pro Phe Gly Ala Gly Thr Gln Gln Phe Asp Trp Leu Thr Ala Ser Asp
65                  70                  75                  80

Ala Lys Gln Arg Ala Thr Glu Lys Met Asp Ala Ala Phe Glu Phe Phe
                85                  90                  95

Thr Lys Leu Gly Val Pro Tyr Tyr Cys Phe His Asp Tyr Asp Leu Ile
            100                 105                 110

Asp Glu Ala Asp Asn Phe Thr Glu Ser Thr Lys Arg Leu Glu Phe Ile
        115                 120                 125

Thr Asp Tyr Ala Lys Gly Lys Gln Ala Ala Ser Gly Val Lys Leu Leu
    130                 135                 140

Trp Gly Thr Ser Asn Cys Phe Ser Asn Pro Arg Phe Met Asn Gly Ala
145                 150                 155                 160

Ala Thr Asn Pro Ser Phe Asp Val Leu Ala Tyr Ala Gly Gly Gln Val
                165                 170                 175

Lys Asn Ala Leu Asp Ala Thr Ile Lys Leu Gly Gly Glu Asn Tyr Val
            180                 185                 190

Phe Trp Gly Gly Arg Glu Gly Tyr Met Ser Leu Leu Asn Thr Asn Met
        195                 200                 205

Lys Arg Glu Gln Glu His Met Ala Lys Phe Leu His Leu Ala Lys Asp
    210                 215                 220

Tyr Ala Arg Ala Gln Gly Phe Lys Gly Thr Phe Phe Ile Glu Pro Lys
225                 230                 235                 240

Pro Met Glu Pro Thr Lys His Gln Tyr Asp Phe Asp Ala Ala Thr Cys
                245                 250                 255

Leu Asn Phe Leu Arg Gln Tyr Asp Leu Leu Asn Asp Phe Lys Leu Asn
            260                 265                 270

Leu Glu Val Asn His Ala Thr Leu Ala Gln His Thr Phe Glu His Glu
        275                 280                 285

Leu Gln Val Ala Ala Asp Asn Asn Val Leu Gly Ser Ile Asp Ala Asn
    290                 295                 300

Arg Gly Asp Tyr Gln Asn Gly Trp Asp Thr Asp Gln Phe Pro Val Asp
305                 310                 315                 320

Leu Tyr Glu Met Thr Gln Ala Met Leu Val Ile Ile Gln Ala Gly Gly
                325                 330                 335

Phe Gln Gly Gly Gly Val Asn Phe Asp Ala Lys Ile Arg Arg Asn Ser
            340                 345                 350

Thr Asp Leu Glu Asp Ile Phe Ile Ala His Ile Ser Gly Met Asp Asn
        355                 360                 365

Phe Ala Arg Ser Phe Leu Ala Ala Asp Lys Ile Leu Glu Lys Ser Lys
    370                 375                 380

Tyr Ser Glu Ile Arg Thr Asn Arg Tyr Ser Ser Phe Asp Ser Gly Lys
385                 390                 395                 400

Gly Lys Asp Phe Glu Asn Gly Ser Leu Ser Leu Thr Asp Leu Ala Thr
                405                 410                 415

Tyr Ala Gln Gly Leu Gly Glu Val Gly Arg Glu Ser Gly Lys Gln Glu
            420                 425                 430

Tyr Leu Glu Ser Ile Ile Asn Gln Tyr Leu
        435                 440
```

<210> SEQ ID NO 11
<211> LENGTH: 1338
<212> TYPE: DNA
<213> ORGANISM: Xanthomonas campestris

<400> SEQUENCE: 11

```
atgagcaaca ccgtctacat cggcgccaaa gagtatttcc ccggcatcgg caagatcggc     60

ttcgaaggcc gcgactccga caacccgctc gcgttcaagg tttacgacgc caacaagaag    120

atcggcgcca agaccatggc cgagcacctg cgctttgccg tggcctactg gcacagcttc    180

tgcggcaacg gcgccgatcc gttcggcccg ggcacgcgtg cgtatccgtg ggatatcggc    240

aacagcgcgc tcgatcgtgc cgaggccaag gccgatgccg cgttcgaatt cttcaccaag    300

ctcggcgtgc cgtattactg ctttcacgat atcgacctgt cgccggatgc cgacgacatc    360

ggcgagtacg aaagcaacct caagcacatg gtgggcatcg ccaagcagcg ccaggccgac    420

accggcatca agctgctctg gggcaccgcc aacctgttct cgcacccgcg ctacatgaat    480

ggtgcatcga ccaacccgga cttcaatgtg gtggcgcgtg ccgcggtgca ggtcaaggcg    540

gcgatcgatg ccacggtgga actgggcggt gaaaactacg tgttctgggg cggccgcgaa    600

ggctatgcct gcctgcacaa cacgcagatg aagcgcgagc aggacaacat ggcgcgcttc    660

ctcaccctgg cacgcgacta cggccgcgcg atcggcttca aaggcaactt cctgatcgag    720

cccaagccca tggagccgat gaagcaccaa tacgacttcg acagcgccac ggtgatcggc    780

ttcctgcgtc agcatggcct ggaccaggat ttcaagctca atatcgaggc caaccacgcc    840

accctgtccg gtcacagctt cgagcacgat ctgcaggttg ccagtgatgc cggcctgctc    900

ggcagcatcg atgccaaccg cggcaacccg cagaatggct gggataccga ccagttcccg    960

accgacctgt acgacaccgt cggcgcgatg ctggtggtgc tgcgccaggg cgggctggca   1020

ccgggtggcc tgaatttcga cgccaaggtg cgccgcgagt cgtccgaccc gcaggacctg   1080

ttcctggcgc acatcggtgg catggacgcg ttcgcacgcg ggctggaagt ggccaatgcg   1140

ctgctgacgt cttcgccgct ggagacctgg cgcgccgagc gttacgccag cttcgacagc   1200

ggcgccggtg ccgactttgc caacggcacc agcacgctgg cggatctggc caagtacgcc   1260

gccggtaatg cgcccaagca actcagcggc cgtcaggaag cctacgaaaa cctgatcaat   1320

cagtatctga tccggtga                                                 1338
```

<210> SEQ ID NO 12
<211> LENGTH: 445
<212> TYPE: PRT
<213> ORGANISM: Xanthomonas campestris

<400> SEQUENCE: 12

```
Met Ser Asn Thr Val Tyr Ile Gly Ala Lys Glu Tyr Phe Pro Gly Ile
1               5                   10                  15

Gly Lys Ile Gly Phe Glu Gly Arg Asp Ser Asp Asn Pro Leu Ala Phe
            20                  25                  30

Lys Val Tyr Asp Ala Asn Lys Lys Ile Gly Ala Lys Thr Met Ala Glu
        35                  40                  45

His Leu Arg Phe Ala Val Ala Tyr Trp His Ser Phe Cys Gly Asn Gly
    50                  55                  60

Ala Asp Pro Phe Gly Pro Gly Thr Arg Ala Tyr Pro Trp Asp Ile Gly
65                  70                  75                  80

Asn Ser Ala Leu Asp Arg Ala Glu Ala Lys Ala Asp Ala Ala Phe Glu
                85                  90                  95

Phe Phe Thr Lys Leu Gly Val Pro Tyr Tyr Cys Phe His Asp Ile Asp
            100                 105                 110

Leu Ser Pro Asp Ala Asp Asp Ile Gly Glu Tyr Glu Ser Asn Leu Lys
```

```
        115                 120                 125

His Met Val Gly Ile Ala Lys Gln Arg Gln Ala Asp Thr Gly Ile Lys
    130                 135                 140

Leu Leu Trp Gly Thr Ala Asn Leu Phe Ser His Pro Arg Tyr Met Asn
145                 150                 155                 160

Gly Ala Ser Thr Asn Pro Asp Phe Asn Val Val Ala Arg Ala Ala Val
                165                 170                 175

Gln Val Lys Ala Ala Ile Asp Ala Thr Val Glu Leu Gly Gly Glu Asn
            180                 185                 190

Tyr Val Phe Trp Gly Gly Arg Glu Gly Tyr Ala Cys Leu His Asn Thr
        195                 200                 205

Gln Met Lys Arg Glu Gln Asp Asn Met Ala Arg Phe Leu Thr Leu Ala
    210                 215                 220

Arg Asp Tyr Gly Arg Ala Ile Gly Phe Lys Gly Asn Phe Leu Ile Glu
225                 230                 235                 240

Pro Lys Pro Met Glu Pro Met Lys His Gln Tyr Asp Phe Asp Ser Ala
                245                 250                 255

Thr Val Ile Gly Phe Leu Arg Gln His Gly Leu Asp Gln Asp Phe Lys
            260                 265                 270

Leu Asn Ile Glu Ala Asn His Ala Thr Leu Ser Gly His Ser Phe Glu
        275                 280                 285

His Asp Leu Gln Val Ala Ser Asp Ala Gly Leu Leu Gly Ser Ile Asp
    290                 295                 300

Ala Asn Arg Gly Asn Pro Gln Asn Gly Trp Asp Thr Asp Gln Phe Pro
305                 310                 315                 320

Thr Asp Leu Tyr Asp Thr Val Gly Ala Met Leu Val Val Leu Arg Gln
                325                 330                 335

Gly Gly Leu Ala Pro Gly Gly Leu Asn Phe Asp Ala Lys Val Arg Arg
            340                 345                 350

Glu Ser Ser Asp Pro Gln Asp Leu Phe Leu Ala His Ile Gly Gly Met
        355                 360                 365

Asp Ala Phe Ala Arg Gly Leu Glu Val Ala Asn Ala Leu Leu Thr Ser
    370                 375                 380

Ser Pro Leu Glu Thr Trp Arg Ala Glu Arg Tyr Ala Ser Phe Asp Ser
385                 390                 395                 400

Gly Ala Gly Ala Asp Phe Ala Asn Gly Thr Ser Thr Leu Ala Asp Leu
                405                 410                 415

Ala Lys Tyr Ala Ala Gly Asn Ala Pro Lys Gln Leu Ser Gly Arg Gln
            420                 425                 430

Glu Ala Tyr Glu Asn Leu Ile Asn Gln Tyr Leu Ile Arg
        435                 440                 445
```

<210> SEQ ID NO 13
<211> LENGTH: 1341
<212> TYPE: DNA
<213> ORGANISM: Treponema primitia

<400> SEQUENCE: 13

```
atggcaaatt attttaccgg cggcaaggaa tattttcccg gcataggaaa aatcccttat      60

gaaggaagcg gatcaaaaaa tcccctggcc tttaagtatt atgacgccga aaaaacggtg     120

cgtggaaaaa aaacaaagga ttggcttcgt tttgcaattg cgtattggca tagtttctgc     180

ggtgatggtg cggacccctt tggctccgct acccatatct tcccatggaa cagtaccaat     240

gaacccctgc agaacgctaa aaataaagcg gacgcggctt ttgaatttat caccaagatc     300
```

```
ggtgctccct actattgctg gcatgaccgg gatatagccc ccgaaggcaa ggacccccgat    360

gaaaccgcca agaacctcgg tattattgtt gatgagttga agaagcggca ggatgctacg    420

ggggtaaaac tcctctgggc aacggccaat gtgtttacca atccccggtt catgaacggg    480

gcggcgacca accctgattt taacattgtg gttcaggccg ccaatcaggt gaaacatgct    540

attgacggcg ccataaagct cggcgccgaa gggtacacct tctggggcgg ccgcgagggt    600

tatatgtctt tgcttaacac ggacatgaaa cgggaaaagg aacacctcgc catattcctg    660

accattgcac gggattatgc acgcaaacaa ggttttaaag gttctttcta tatcgaaccg    720

aaaccgatgg aaccgaccaa acatcagtat gattttgatt ccgaaacggt tatcggtttt    780

ttaaaagccc acggccttga gaaggacttt aagttgaata ttgaggctaa ccacgcggaa    840

cttgcgggcc atgatttcta tcatgaactg tcggtctgtg ttgataacga tatgctcgga    900

tcggttgacg caaaccgcgg cgaaccccgt aacggctggg atacggatca attcccctcc    960

agcgtttatg agaccaccct ggcgatgctt actatcctcc gcatgggcgg tttcaaaacc   1020

ggggggctta atttcgatgc aaaaatccgc cgcaactcaa ttgatcctga ggatcttttt   1080

atcgcccaca tcggcggtat ggacaccttt gcctacggac ttgaaaaggc ctctgcggtc   1140

cttgatgacg ggcgtattcc ggatctgatt aaaaaacgtt actcctcctt tgattcaggg   1200

gatggcgcga aatttgagaa gagcggattt accctggacg cgttggccgc tcttgccaag   1260

gattacggta aagccggctg gaccagcggc aagcaggaac tgtttgaaaa tctcttttct   1320

gatattatat tgttaaaata a                                             1341
```

```
<210> SEQ ID NO 14
<211> LENGTH: 446
<212> TYPE: PRT
<213> ORGANISM: Treponema primitia

<400> SEQUENCE: 14

Met Ala Asn Tyr Phe Thr Gly Gly Lys Glu Tyr Phe Pro Gly Ile Gly
1               5                   10                  15

Lys Ile Pro Tyr Glu Gly Ser Gly Ser Lys Asn Pro Leu Ala Phe Lys
            20                  25                  30

Tyr Tyr Asp Ala Glu Lys Thr Val Arg Gly Lys Lys Thr Lys Asp Trp
        35                  40                  45

Leu Arg Phe Ala Ile Ala Tyr Trp His Ser Phe Cys Gly Asp Gly Ala
    50                  55                  60

Asp Pro Phe Gly Ser Ala Thr His Ile Phe Pro Trp Asn Ser Thr Asn
65                  70                  75                  80

Glu Pro Leu Gln Asn Ala Lys Asn Lys Ala Asp Ala Ala Phe Glu Phe
                85                  90                  95

Ile Thr Lys Ile Gly Ala Pro Tyr Tyr Cys Trp His Asp Arg Asp Ile
            100                 105                 110

Ala Pro Glu Gly Lys Asp Pro Asp Glu Thr Ala Lys Asn Leu Gly Ile
        115                 120                 125

Ile Val Asp Glu Leu Lys Lys Arg Gln Asp Ala Thr Gly Val Lys Leu
    130                 135                 140

Leu Trp Ala Thr Ala Asn Val Phe Thr Asn Pro Arg Phe Met Asn Gly
145                 150                 155                 160

Ala Ala Thr Asn Pro Asp Phe Asn Ile Val Val Gln Ala Ala Asn Gln
                165                 170                 175

Val Lys His Ala Ile Asp Gly Ala Ile Lys Leu Gly Ala Glu Gly Tyr
```

```
            180                 185                 190

Thr Phe Trp Gly Gly Arg Glu Gly Tyr Met Ser Leu Leu Asn Thr Asp
        195                 200                 205

Met Lys Arg Glu Lys Glu His Leu Ala Ile Phe Leu Thr Ile Ala Arg
    210                 215                 220

Asp Tyr Ala Arg Lys Gln Gly Phe Lys Gly Ser Phe Tyr Ile Glu Pro
225                 230                 235                 240

Lys Pro Met Glu Pro Thr Lys His Gln Tyr Asp Phe Asp Ser Glu Thr
                245                 250                 255

Val Ile Gly Phe Leu Lys Ala His Gly Leu Glu Lys Asp Phe Lys Leu
            260                 265                 270

Asn Ile Glu Ala Asn His Ala Glu Leu Ala Gly His Asp Phe Tyr His
        275                 280                 285

Glu Leu Ser Val Cys Val Asp Asn Asp Met Leu Gly Ser Val Asp Ala
    290                 295                 300

Asn Arg Gly Glu Pro Arg Asn Gly Trp Asp Thr Asp Gln Phe Pro Ser
305                 310                 315                 320

Ser Val Tyr Glu Thr Thr Leu Ala Met Leu Thr Ile Leu Arg Met Gly
                325                 330                 335

Gly Phe Lys Thr Gly Gly Leu Asn Phe Asp Ala Lys Ile Arg Arg Asn
            340                 345                 350

Ser Ile Asp Pro Glu Asp Leu Phe Ile Ala His Ile Gly Gly Met Asp
        355                 360                 365

Thr Phe Ala Tyr Gly Leu Glu Lys Ala Ser Ala Val Leu Asp Asp Gly
    370                 375                 380

Arg Ile Pro Asp Leu Ile Lys Lys Arg Tyr Ser Ser Phe Asp Ser Gly
385                 390                 395                 400

Asp Gly Ala Lys Phe Glu Lys Ser Gly Phe Thr Leu Asp Ala Leu Ala
                405                 410                 415

Ala Leu Ala Lys Asp Tyr Gly Lys Ala Gly Trp Thr Ser Gly Lys Gln
            420                 425                 430

Glu Leu Phe Glu Asn Leu Phe Ser Asp Ile Ile Leu Leu Lys
        435                 440                 445
```

<210> SEQ ID NO 15
<211> LENGTH: 1329
<212> TYPE: DNA
<213> ORGANISM: Pedobacter heparinus

<400> SEQUENCE: 15

```
atgacaaaac ttactgcaga caacgaatat ttcaaaggga tcggacagat cagctttgaa     60

ggacaggaaa cagacaaccc gctggctttc agatggtaca atcctgaaca ggtggttgcc    120

ggcaaaaaga tgaaagagca cctgcgtttt gccggtgctt actggcattc tttctgcgga    180

aatggtacag atccctttgg cggtccgaca catatttttc cctgggacgc gaaagcggat    240

gtactggatc gtgcaaagga caaaatggat gcagcctttg aatttctgac caaaatgaac    300

ctgccctatt actgctttca tgatgtggat gtggtagatt atggcaacga catcaaagaa    360

aatgaaagac ggatgcagat catgaccgat tatgcaaaag ccaaacaggc agaaacaggt    420

gtaaaattgc tttggggtac ggctaatctt ttctctcacc gcaggtatat gaacggagcg    480

gctaccaatc ccgactttca tgtgctgagc catggcgcag cacaggtaaa agcagccctt    540

gatgccacca tagcccttaa tggggaaaat tatgtattct ggggtggccg cgaaggttac    600

atgagcctcc tgaacaccaa tatgaaacgc gaacaggaac atctggcaaa atttctgcat    660
```

```
acagccaaag attatgcccg taaaaatggt ttcaaaggca ccttctttat tgagcccaaa    720

ccttgtgaac ccaccaagca ccagtacgat tacgatgcag caaccgtact tggctttctc    780

cgtcagtacg acctgctggg tgattttaaa ctgaacctgg aagttaacca tgctacgctg    840

gccggacata ccttccagca tgagctgcag gtggctgctg atgccggaat gctgggctct    900

attgatgcca accgcggcga cgaacaaaat ggctgggata cagaccagtt tccaaacaac    960

atcaatgagg ttacagaatc catgctgatc atcctggaag cagggggcct gcaaggtggg   1020

ggtataaatt tcgatgccaa gatccgcagg aattcaacgg atccggccga ccttttccat   1080

gcacatattg gtggaatgga tattttcgcc cgggccctga ttaccgccga ccgcatcctt   1140

cagcattctg aatacaaaaa aataagggca gaaagatatg cgtcttacga cagtggaaaa   1200

ggcaaagcct ttgaagaagg gagcttaagc ctggaagacc tgcgcgatta tgcagtggca   1260

cagggcgaac cgcaaaccat cagcggcaaa caggaattcc tggaaaacct gatcaacagg   1320

tatatttaa                                                           1329
```

```
<210> SEQ ID NO 16
<211> LENGTH: 442
<212> TYPE: PRT
<213> ORGANISM: Pedobacter heparinus

<400> SEQUENCE: 16

Met Thr Lys Leu Thr Ala Asp Asn Glu Tyr Phe Lys Gly Ile Gly Gln
1               5                   10                  15

Ile Ser Phe Glu Gly Gln Glu Thr Asp Asn Pro Leu Ala Phe Arg Trp
            20                  25                  30

Tyr Asn Pro Glu Gln Val Val Ala Gly Lys Lys Met Lys Glu His Leu
        35                  40                  45

Arg Phe Ala Gly Ala Tyr Trp His Ser Phe Cys Gly Asn Gly Thr Asp
    50                  55                  60

Pro Phe Gly Gly Pro Thr His Ile Phe Pro Trp Asp Ala Lys Ala Asp
65                  70                  75                  80

Val Leu Asp Arg Ala Lys Asp Lys Met Asp Ala Ala Phe Glu Phe Leu
                85                  90                  95

Thr Lys Met Asn Leu Pro Tyr Tyr Cys Phe His Asp Val Asp Val Val
            100                 105                 110

Asp Tyr Gly Asn Asp Ile Lys Glu Asn Glu Arg Arg Met Gln Ile Met
        115                 120                 125

Thr Asp Tyr Ala Lys Ala Lys Gln Ala Glu Thr Gly Val Lys Leu Leu
    130                 135                 140

Trp Gly Thr Ala Asn Leu Phe Ser His Arg Arg Tyr Met Asn Gly Ala
145                 150                 155                 160

Ala Thr Asn Pro Asp Phe His Val Leu Ser His Gly Ala Ala Gln Val
                165                 170                 175

Lys Ala Ala Leu Asp Ala Thr Ile Ala Leu Asn Gly Glu Asn Tyr Val
            180                 185                 190

Phe Trp Gly Gly Arg Glu Gly Tyr Met Ser Leu Leu Asn Thr Asn Met
        195                 200                 205

Lys Arg Glu Gln Glu His Leu Ala Lys Phe Leu His Thr Ala Lys Asp
    210                 215                 220

Tyr Ala Arg Lys Asn Gly Phe Lys Gly Thr Phe Phe Ile Glu Pro Lys
225                 230                 235                 240

Pro Cys Glu Pro Thr Lys His Gln Tyr Asp Tyr Asp Ala Ala Thr Val
```

```
                245                 250                 255

Leu Gly Phe Leu Arg Gln Tyr Asp Leu Leu Gly Asp Phe Lys Leu Asn
            260                 265                 270

Leu Glu Val Asn His Ala Thr Leu Ala Gly His Thr Phe Gln His Glu
        275                 280                 285

Leu Gln Val Ala Ala Asp Ala Gly Met Leu Gly Ser Ile Asp Ala Asn
    290                 295                 300

Arg Gly Asp Glu Gln Asn Gly Trp Asp Thr Asp Gln Phe Pro Asn Asn
305                 310                 315                 320

Ile Asn Glu Val Thr Glu Ser Met Leu Ile Ile Leu Glu Ala Gly Gly
                325                 330                 335

Leu Gln Gly Gly Gly Ile Asn Phe Asp Ala Lys Ile Arg Arg Asn Ser
            340                 345                 350

Thr Asp Pro Ala Asp Leu Phe His Ala His Ile Gly Gly Met Asp Ile
        355                 360                 365

Phe Ala Arg Ala Leu Ile Thr Ala Asp Arg Ile Leu Gln His Ser Glu
    370                 375                 380

Tyr Lys Lys Ile Arg Ala Glu Arg Tyr Ala Ser Tyr Asp Ser Gly Lys
385                 390                 395                 400

Gly Lys Ala Phe Glu Glu Gly Ser Leu Ser Leu Glu Asp Leu Arg Asp
                405                 410                 415

Tyr Ala Val Ala Gln Gly Glu Pro Gln Thr Ile Ser Gly Lys Gln Glu
            420                 425                 430

Phe Leu Glu Asn Leu Ile Asn Arg Tyr Ile
        435                 440
```

<210> SEQ ID NO 17
<211> LENGTH: 876
<212> TYPE: DNA
<213> ORGANISM: Pyrolobus fumarii

<400> SEQUENCE: 17

```
gtggggggcc cactcgtgcc ggagaggata cgcttcggac cagcgggtaa gccggtcggc     60

atgaagagtg gcgactatgt caaggctatc gagtatgtgg cgaacgaggg tctcgacgca    120

ctcgagtatg aggcggtgcg cggcgtgcgt atcagcgaga agaaggctgt tgagataaag    180

agggctgcct tggagcacgg tatccttctc tcgatgcacg cgccctactt catcaaccta    240

gcgtcgccca acgaggacac cgttaagaag agccaacaga ggcttctcga cgcgctcaag    300

gcggctaact ggatgggcgc ctatgtggtc gtcttccacc cgggctacta caaggacaac    360

ccgagtaaag aagccgccct caagagggtg atcgagaacc tgaagcccgt tgtagagcag    420

gctaagcagc tcgggatcaa gggtgtcgag ctgggccccg agactaccgg gaagagagcc    480

caggtcggcg atatagacga ggtgatcaca atctgcaggg aggttgagat gtgccgcccg    540

gtggtagact gggcgcacat ctacgccagg taccggggcc aacacgtgac cagcatcgac    600

caggtgctca aggtgataga gaagattgag aaggagcttg ggagtcgcgc tgtcaacccg    660

ctacacactc acttctcgcg catcgagtac ggggagggag gagagaggga gcaccatacg    720

ctcgacgagg cggagtatgg accggagttt aggatagtgt gtgaggctta caaacaagcc    780

gggatacgcg cagtgataat ctcggagagc ccgatactag accaggacgc actcaagatg    840

aagaagattt gttgcgagga gctaggctac tgctag                              876
```

<210> SEQ ID NO 18
<211> LENGTH: 291

```
<212> TYPE: PRT
<213> ORGANISM: Pyrolobus fumarii

<400> SEQUENCE: 18

Val Gly Gly Pro Leu Val Pro Glu Arg Ile Arg Phe Gly Pro Ala Gly
1               5                   10                  15

Lys Pro Val Gly Met Lys Ser Gly Asp Tyr Val Lys Ala Ile Glu Tyr
            20                  25                  30

Val Ala Asn Glu Gly Leu Asp Ala Leu Glu Tyr Glu Ala Val Arg Gly
        35                  40                  45

Val Arg Ile Ser Glu Lys Lys Ala Val Glu Ile Lys Arg Ala Ala Leu
    50                  55                  60

Glu His Gly Ile Leu Leu Ser Met His Ala Pro Tyr Phe Ile Asn Leu
65                  70                  75                  80

Ala Ser Pro Asn Glu Asp Thr Val Lys Lys Ser Gln Gln Arg Leu Leu
                85                  90                  95

Asp Ala Leu Lys Ala Ala Asn Trp Met Gly Ala Tyr Val Val Val Phe
            100                 105                 110

His Pro Gly Tyr Tyr Lys Asp Asn Pro Ser Lys Glu Ala Ala Leu Lys
        115                 120                 125

Arg Val Ile Glu Asn Leu Lys Pro Val Val Glu Gln Ala Lys Gln Leu
    130                 135                 140

Gly Ile Lys Gly Val Glu Leu Gly Pro Glu Thr Thr Gly Lys Arg Ala
145                 150                 155                 160

Gln Val Gly Asp Ile Asp Glu Val Ile Thr Ile Cys Arg Glu Val Glu
                165                 170                 175

Met Cys Arg Pro Val Val Asp Trp Ala His Ile Tyr Ala Arg Tyr Arg
            180                 185                 190

Gly Gln His Val Thr Ser Ile Asp Gln Val Leu Lys Val Ile Glu Lys
        195                 200                 205

Ile Glu Lys Glu Leu Gly Ser Arg Ala Val Asn Pro Leu His Thr His
    210                 215                 220

Phe Ser Arg Ile Glu Tyr Gly Glu Gly Gly Glu Arg Glu His His Thr
225                 230                 235                 240

Leu Asp Glu Ala Glu Tyr Gly Pro Glu Phe Arg Ile Val Cys Glu Ala
                245                 250                 255

Tyr Lys Gln Ala Gly Ile Arg Ala Val Ile Ile Ser Glu Ser Pro Ile
            260                 265                 270

Leu Asp Gln Asp Ala Leu Lys Met Lys Lys Ile Cys Cys Glu Glu Leu
        275                 280                 285

Gly Tyr Cys
    290


<210> SEQ ID NO 19
<211> LENGTH: 972
<212> TYPE: DNA
<213> ORGANISM: Geobacillus species

<400> SEQUENCE: 19

atgaaagtag gcgtatttac cgtcttgtat caacagctgc cgttggaaga catgctcgac      60

aaagtcgccg ccatgggcat tgaggccgtt gagcttggca ccggcaatta cccgggcagc     120

gcccattgcg atcccgacgc gctgttggac cagccggaaa acatcaaagc gttgaaaaaa     180

gccgtcgccg accgcggcct tgtcatcagc gccttaagct gccatggcaa tccgcttcat     240

ccggacaaaa cgttcgcgaa acagtcgcat gacacgtggc ggaaaactgt caggctcgcc     300
```

```
gagcagcttg aagtcccggt catcaacgcc ttctccggct gcccgggcga ccatcccggc    360

gccaaatacc cgaactgggt cacatgctcc tggccgccgg attacttgga aattttaaaa    420

tggcaatggg aagaagtcgt catcccgtac tggcgcgaag aagcagcgtt cgccaaggag    480

cacggcatca cgcaaatcgc ctttgaaatg catccgggct tcgtcgtcta caacccggaa    540

acgctcctca aactgcgcga acacgtcggt gaagcgatcg gcgccaactt tgacccgagc    600

cacttgcttt ggcaaggcat cgacccggtt gaggcgatca aactgctcgg ccgcgaaaaa    660

gcgattttcc acgtccatgc gaaagacacg tacttagacg aagcgaacat ccgcaaaaac    720

ggcgtgctcg atacgaaaca ttacagccaa attctcgatc gctcatgggt gttccgcacc    780

gtcggctacg ggcaaagcga aaaaatgtgg cgcgacatcg tcagcgccct gcgcgccgtc    840

ggctacgact acgtgctgtc aatcgaacac gaagatatgc tcgcttcgat cgatgaaggg    900

ctgtcaaagg ccgtcgccct cttgaaaaag gtgttgttca aagaagaact gccggagatg    960

tggtgggcat aa                                                         972
```

```
<210> SEQ ID NO 20
<211> LENGTH: 323
<212> TYPE: PRT
<213> ORGANISM: Geobacillus species

<400> SEQUENCE: 20

Met Lys Val Gly Val Phe Thr Val Leu Tyr Gln Gln Leu Pro Leu Glu
1               5                   10                  15

Asp Met Leu Asp Lys Val Ala Ala Met Gly Ile Glu Ala Val Glu Leu
            20                  25                  30

Gly Thr Gly Asn Tyr Pro Gly Ser Ala His Cys Asp Pro Asp Ala Leu
        35                  40                  45

Leu Asp Gln Pro Glu Asn Ile Lys Ala Leu Lys Lys Ala Val Ala Asp
    50                  55                  60

Arg Gly Leu Val Ile Ser Ala Leu Ser Cys His Gly Asn Pro Leu His
65                  70                  75                  80

Pro Asp Lys Thr Phe Ala Lys Gln Ser His Asp Thr Trp Arg Lys Thr
                85                  90                  95

Val Arg Leu Ala Glu Gln Leu Glu Val Pro Val Ile Asn Ala Phe Ser
            100                 105                 110

Gly Cys Pro Gly Asp His Pro Gly Ala Lys Tyr Pro Asn Trp Val Thr
        115                 120                 125

Cys Ser Trp Pro Pro Asp Tyr Leu Glu Ile Leu Lys Trp Gln Trp Glu
    130                 135                 140

Glu Val Val Ile Pro Tyr Trp Arg Glu Glu Ala Ala Phe Ala Lys Glu
145                 150                 155                 160

His Gly Ile Thr Gln Ile Ala Phe Glu Met His Pro Gly Phe Val Val
                165                 170                 175

Tyr Asn Pro Glu Thr Leu Leu Lys Leu Arg Glu His Val Gly Glu Ala
            180                 185                 190

Ile Gly Ala Asn Phe Asp Pro Ser His Leu Leu Trp Gln Gly Ile Asp
        195                 200                 205

Pro Val Glu Ala Ile Lys Leu Leu Gly Arg Glu Lys Ala Ile Phe His
    210                 215                 220

Val His Ala Lys Asp Thr Tyr Leu Asp Glu Ala Asn Ile Arg Lys Asn
225                 230                 235                 240

Gly Val Leu Asp Thr Lys His Tyr Ser Gln Ile Leu Asp Arg Ser Trp
```

```
            245                 250                 255

Val Phe Arg Thr Val Gly Tyr Gly Gln Ser Glu Lys Met Trp Arg Asp
        260                 265                 270

Ile Val Ser Ala Leu Arg Ala Val Gly Tyr Asp Tyr Val Leu Ser Ile
    275                 280                 285

Glu His Glu Asp Met Leu Ala Ser Ile Asp Glu Gly Leu Ser Lys Ala
    290                 295                 300

Val Ala Leu Leu Lys Lys Val Leu Phe Lys Glu Glu Leu Pro Glu Met
305                 310                 315                 320

Trp Trp Ala


<210> SEQ ID NO 21
<211> LENGTH: 1335
<212> TYPE: DNA
<213> ORGANISM: Thermotoga neapolitana

<400> SEQUENCE: 21

atggctgaat tctttccaga aatcccgaaa gtgcagttcg aaggcaaaga aagcacaaat      60

ccacttgcgt tcaagttcta cgatccagaa gagatcatcg acggcaaacc cctcaaggac     120

catctgaagt tctccgttgc cttctggcac accttcgtga acgagggaag ggatcccttc     180

ggagacccaa cggccgatcg tccctggaac aggtacaccg atcccatgga caaggctttt     240

gcaagggtgg acgccctttt tgaattctgc gaaaaactca acatcgagta cttctgcttc     300

cacgacagag acatcgctcc cgagggaaaa acgctgaggg agacaaacaa aattttggac     360

aaagtagtgg agagaatcaa agagagaatg aaagacagca acgtgaagct cctctggggt     420

actgcaaacc tcttttccca cccaaggtac atgcatggtg cagcgacaac ctgcagtgct     480

gatgtttttg cgtacgcggc cgcccaggtg aaaaaagccc ttgagatcac caaagaactt     540

ggaggagaag ggtacgtctt ctggggtgga agagaaggat acgaaacact cctcaacacg     600

gaccttggat tcgaacttga aaacctcgcc cgcttcctca gaatggctgt ggattatgca     660

aaaaggatcg gtttcaccgg acagttcctc atcgaaccaa aaccgaaaga acccaccaaa     720

caccagtacg acttcgacgt tgcaaccgcc tatgccttcc tgaagagcca cggtctcgat     780

gaatacttca aattcaacat cgaggcaaac cacgccacac tcgccggtca caccttccag     840

cacgaactga gaatggcaag gatccttgga aaactcggaa gcatcgatgc aaaccaggga     900

gaccttcttc ttggatggga caccgatcag ttcccaacaa acgtctacga tacaaccctt     960

gcaatgtacg aagtgataaa agcgggaggc ttcacaaaag gtgggctcaa cttcgatgcg    1020

aaggtgagga gggcttctta caaagtggag gacctcttca tagggcacat agcgggaatg    1080

gacacctttg cactcggttt caaggtggca tacaaactcg tgaaggatgg tgttctggac    1140

aaattcatcg aagaaaagta cagaagtttc agggagggca ttggaaggga catcgtcgaa    1200

ggtaaagtgg attttgaaaa acttgaagag tatataatag acaaagaaac gatagaactt    1260

ccatctggaa agcaagaata cctggaaagc ctcatcaaca gttacatagt gaagaccatt    1320

ctggaactga ggtga                                                     1335


<210> SEQ ID NO 22
<211> LENGTH: 444
<212> TYPE: PRT
<213> ORGANISM: Thermotoga neapolitana

<400> SEQUENCE: 22

Met Ala Glu Phe Phe Pro Glu Ile Pro Lys Val Gln Phe Glu Gly Lys
```

-continued

```
1               5                   10                  15

Glu Ser Thr Asn Pro Leu Ala Phe Lys Phe Tyr Asp Pro Glu Glu Ile
            20                  25                  30

Ile Asp Gly Lys Pro Leu Lys Asp His Leu Lys Phe Ser Val Ala Phe
        35                  40                  45

Trp His Thr Phe Val Asn Glu Gly Arg Asp Pro Phe Gly Asp Pro Thr
    50                  55                  60

Ala Asp Arg Pro Trp Asn Arg Tyr Thr Asp Pro Met Asp Lys Ala Phe
65                  70                  75                  80

Ala Arg Val Asp Ala Leu Phe Glu Phe Cys Glu Lys Leu Asn Ile Glu
                85                  90                  95

Tyr Phe Cys Phe His Asp Arg Asp Ile Ala Pro Glu Gly Lys Thr Leu
            100                 105                 110

Arg Glu Thr Asn Lys Ile Leu Asp Lys Val Val Glu Arg Ile Lys Glu
        115                 120                 125

Arg Met Lys Asp Ser Asn Val Lys Leu Leu Trp Gly Thr Ala Asn Leu
    130                 135                 140

Phe Ser His Pro Arg Tyr Met His Gly Ala Ala Thr Thr Cys Ser Ala
145                 150                 155                 160

Asp Val Phe Ala Tyr Ala Ala Ala Gln Val Lys Lys Ala Leu Glu Ile
                165                 170                 175

Thr Lys Glu Leu Gly Gly Glu Gly Tyr Val Phe Trp Gly Gly Arg Glu
            180                 185                 190

Gly Tyr Glu Thr Leu Leu Asn Thr Asp Leu Gly Phe Glu Leu Glu Asn
        195                 200                 205

Leu Ala Arg Phe Leu Arg Met Ala Val Asp Tyr Ala Lys Arg Ile Gly
    210                 215                 220

Phe Thr Gly Gln Phe Leu Ile Glu Pro Lys Pro Lys Glu Pro Thr Lys
225                 230                 235                 240

His Gln Tyr Asp Phe Asp Val Ala Thr Ala Tyr Ala Phe Leu Lys Ser
                245                 250                 255

His Gly Leu Asp Glu Tyr Phe Lys Phe Asn Ile Glu Ala Asn His Ala
            260                 265                 270

Thr Leu Ala Gly His Thr Phe Gln His Glu Leu Arg Met Ala Arg Ile
        275                 280                 285

Leu Gly Lys Leu Gly Ser Ile Asp Ala Asn Gln Gly Asp Leu Leu Leu
    290                 295                 300

Gly Trp Asp Thr Asp Gln Phe Pro Thr Asn Val Tyr Asp Thr Thr Leu
305                 310                 315                 320

Ala Met Tyr Glu Val Ile Lys Ala Gly Gly Phe Thr Lys Gly Gly Leu
                325                 330                 335

Asn Phe Asp Ala Lys Val Arg Arg Ala Ser Tyr Lys Val Glu Asp Leu
            340                 345                 350

Phe Ile Gly His Ile Ala Gly Met Asp Thr Phe Ala Leu Gly Phe Lys
        355                 360                 365

Val Ala Tyr Lys Leu Val Lys Asp Gly Val Leu Asp Lys Phe Ile Glu
    370                 375                 380

Glu Lys Tyr Arg Ser Phe Arg Glu Gly Ile Gly Arg Asp Ile Val Glu
385                 390                 395                 400

Gly Lys Val Asp Phe Glu Lys Leu Glu Glu Tyr Ile Ile Asp Lys Glu
                405                 410                 415

Thr Ile Glu Leu Pro Ser Gly Lys Gln Glu Tyr Leu Glu Ser Leu Ile
            420                 425                 430
```

```
Asn Ser Tyr Ile Val Lys Thr Ile Leu Glu Leu Arg
        435                 440


<210> SEQ ID NO 23
<211> LENGTH: 663
<212> TYPE: DNA
<213> ORGANISM: Thermotoga maritima

<400> SEQUENCE: 23

gtgtggacca ttctgtgcga taaagatagc ggaggagttc tcttgagaaa aggtgtatcc     60

acgagcatca taagaagcaa tcccgatctg cttgaagcac tcccgaaagc agaactttac    120

gaactgggtt ttttcaaggc ggaagacttc gagaaggtcc tccgcttttt tcacgacaaa    180

aattttggaa tccacgctcc tttcatctac aggtacagat accaccatcc gaatccgacc    240

tctctgaacg aggaagaaag agaggacacc ttttctgtga acaaaaaatg cgctgagctt    300

gccaggaaga tcggcgcaga atacatgata attcacttcc caaatgccct tcagaaagaa    360

aactggcttt ctgtttacag agaggtggag agagaattct ccgagcttgc gggtgtcatc    420

agcgttcgag tggagaacgt ttatggaaac gatcatttcc actccgctga agattacagg    480

acctttcttg aaaacacagg ttgtaagatg tgcgttgaca tcggccatct tcttctagac    540

gctgaggttt acggtttttc tcccatcgaa ttcatagaaa aactctctga ttttgtagaa    600

gaatttcaca tttacacgcg gatttcgaaa cctacaaaaa tgccatcacg ctccctgggg    660

tga                                                                  663


<210> SEQ ID NO 24
<211> LENGTH: 220
<212> TYPE: PRT
<213> ORGANISM: Thermotoga maritima

<400> SEQUENCE: 24

Val Trp Thr Ile Leu Cys Asp Lys Asp Ser Gly Gly Val Leu Leu Arg
1               5                   10                  15

Lys Gly Val Ser Thr Ser Ile Ile Arg Ser Asn Pro Asp Leu Leu Glu
            20                  25                  30

Ala Leu Pro Lys Ala Glu Leu Tyr Glu Leu Gly Phe Phe Lys Ala Glu
        35                  40                  45

Asp Phe Glu Lys Val Leu Arg Phe Phe His Asp Lys Asn Phe Gly Ile
    50                  55                  60

His Ala Pro Phe Ile Tyr Arg Tyr Arg Tyr His His Pro Asn Pro Thr
65                  70                  75                  80

Ser Leu Asn Glu Glu Glu Arg Glu Asp Thr Phe Ser Val Asn Lys Lys
                85                  90                  95

Cys Ala Glu Leu Ala Arg Lys Ile Gly Ala Glu Tyr Met Ile Ile His
            100                 105                 110

Phe Pro Asn Ala Leu Gln Lys Glu Asn Trp Leu Ser Val Tyr Arg Glu
        115                 120                 125

Val Glu Arg Glu Phe Ser Glu Leu Ala Gly Val Ile Ser Val Arg Val
    130                 135                 140

Glu Asn Val Tyr Gly Asn Asp His Phe His Ser Ala Glu Asp Tyr Arg
145                 150                 155                 160

Thr Phe Leu Glu Asn Thr Gly Cys Lys Met Cys Val Asp Ile Gly His
                165                 170                 175

Leu Leu Leu Asp Ala Glu Val Tyr Gly Phe Ser Pro Ile Glu Phe Ile
            180                 185                 190
```

```
Glu Lys Leu Ser Asp Phe Val Glu Glu Phe His Ile Tyr Thr Arg Ile
        195                 200                 205

Ser Lys Pro Thr Lys Met Pro Ser Arg Ser Leu Gly
    210                 215                 220


<210> SEQ ID NO 25
<211> LENGTH: 1320
<212> TYPE: DNA
<213> ORGANISM: Clostridium clariflavum

<400> SEQUENCE: 25

atgtcagagt attttaaagg aatatcaaaa atacagtatg aaggaaagga ttcagacaat      60

cctttagcct ttaagtacta taatcctgat gaggttgtcg gagacaagac aatgaaagaa     120

cacctcaggt ttgctgttgc ttattggcat acattccagg gcacaggagc agacccattc     180

ggtgtaggca cagctcaaag accgtgggaa aatattactg atccaatgga tttggcaaaa     240

gcaaaggtag aagctaactt tgaattttgt gaaaagttag ggttcctttt cttctgcttc     300

catgacagag atatagctcc tgaagctgac aatctcagag agacaaataa aagacttgat     360

gagattgtag cagtaataaa ggatcgcatg aagaacagcc ctgtaaaact tctctgggga     420

acaaccaatg cgtttggcaa tccaagattt gttcatgggg cttcaacttc tccaaatgca     480

gatgtatttg catatgcagc tgcccaagta aagaaagcta tggagataac taaggaactt     540

ggcggtcaga actatgtatt ctggggcgga agagaaggtt atgagacact gctcaatacc     600

gatatgaagc ttgagttgga caatatggca agattcttaa gaatggctgt ggaatataaa     660

aaggaaatag gatttgacgg ccagctctta attgagccta agccaaagga acctacaaaa     720

catcagtatg attttgatac tgctacagtg atcggattct tgagaaccta cggacttgaa     780

aaagaattta aaatgaacat tgaggctaac catgctaccc tcgctgctca cacattccag     840

catgaactta gggtggcagc tataaacaat gcattaggaa gcattgacgc aaatcagggt     900

gacttgttgt taggatggga tactgaccaa ttcccgacaa acttatatga tacaaccctc     960

gcaatgtatg aagtattgaa ggccggcgga tttacaaaag gcggtttgaa ctttgactcg    1020

aaagtgagaa gaggttcctt tgaaccggtt gatctcttct atgctcatat tgcaggtatg    1080

gatgcttttg caagaggctt gaaagttgct tacaagatgc ttcaggacgg taaatttgaa    1140

aagttcattg aagaaagata ccagagctat aagaccggaa tcggaaaaga tattgttgaa    1200

ggaaaagttg gatttaaaga actcgaaaag tatgttttag agcttgaaac ggtaaaaaat    1260

acatccggta ggcaggaagt tcttgaagca atgttgaata aatatattat tgaaagctaa    1320


<210> SEQ ID NO 26
<211> LENGTH: 439
<212> TYPE: PRT
<213> ORGANISM: Clostridium clariflavum

<400> SEQUENCE: 26

Met Ser Glu Tyr Phe Lys Gly Ile Ser Lys Ile Gln Tyr Glu Gly Lys
1               5                   10                  15

Asp Ser Asp Asn Pro Leu Ala Phe Lys Tyr Tyr Asn Pro Asp Glu Val
            20                  25                  30

Val Gly Asp Lys Thr Met Lys Glu His Leu Arg Phe Ala Val Ala Tyr
        35                  40                  45

Trp His Thr Phe Gln Gly Thr Gly Ala Asp Pro Phe Gly Val Gly Thr
    50                  55                  60
```

```
Ala Gln Arg Pro Trp Glu Asn Ile Thr Asp Pro Met Asp Leu Ala Lys
65                  70                  75                  80

Ala Lys Val Glu Ala Asn Phe Glu Phe Cys Glu Lys Leu Gly Val Pro
                85                  90                  95

Phe Phe Cys Phe His Asp Arg Asp Ile Ala Pro Glu Ala Asp Asn Leu
            100                 105                 110

Arg Glu Thr Asn Lys Arg Leu Asp Glu Ile Val Ala Val Ile Lys Asp
        115                 120                 125

Arg Met Lys Asn Ser Pro Val Lys Leu Leu Trp Gly Thr Thr Asn Ala
    130                 135                 140

Phe Gly Asn Pro Arg Phe Val His Gly Ala Ser Thr Ser Pro Asn Ala
145                 150                 155                 160

Asp Val Phe Ala Tyr Ala Ala Ala Gln Val Lys Lys Ala Met Glu Ile
                165                 170                 175

Thr Lys Glu Leu Gly Gly Gln Asn Tyr Val Phe Trp Gly Gly Arg Glu
            180                 185                 190

Gly Tyr Glu Thr Leu Leu Asn Thr Asp Met Lys Leu Glu Leu Asp Asn
        195                 200                 205

Met Ala Arg Phe Leu Arg Met Ala Val Glu Tyr Lys Lys Glu Ile Gly
    210                 215                 220

Phe Asp Gly Gln Leu Leu Ile Glu Pro Lys Pro Lys Glu Pro Thr Lys
225                 230                 235                 240

His Gln Tyr Asp Phe Asp Thr Ala Thr Val Ile Gly Phe Leu Arg Thr
                245                 250                 255

Tyr Gly Leu Glu Lys Glu Phe Lys Met Asn Ile Glu Ala Asn His Ala
            260                 265                 270

Thr Leu Ala Ala His Thr Phe Gln His Glu Leu Arg Val Ala Ala Ile
        275                 280                 285

Asn Asn Ala Leu Gly Ser Ile Asp Ala Asn Gln Gly Asp Leu Leu Leu
    290                 295                 300

Gly Trp Asp Thr Asp Gln Phe Pro Thr Asn Leu Tyr Asp Thr Thr Leu
305                 310                 315                 320

Ala Met Tyr Glu Val Leu Lys Ala Gly Gly Phe Thr Lys Gly Gly Leu
                325                 330                 335

Asn Phe Asp Ser Lys Val Arg Arg Gly Ser Phe Glu Pro Val Asp Leu
            340                 345                 350

Phe Tyr Ala His Ile Ala Gly Met Asp Ala Phe Ala Arg Gly Leu Lys
        355                 360                 365

Val Ala Tyr Lys Met Leu Gln Asp Gly Lys Phe Glu Lys Phe Ile Glu
    370                 375                 380

Glu Arg Tyr Gln Ser Tyr Lys Thr Gly Ile Gly Lys Asp Ile Val Glu
385                 390                 395                 400

Gly Lys Val Gly Phe Lys Glu Leu Glu Lys Tyr Val Leu Glu Leu Glu
                405                 410                 415

Thr Val Lys Asn Thr Ser Gly Arg Gln Glu Val Leu Glu Ala Met Leu
            420                 425                 430

Asn Lys Tyr Ile Ile Glu Ser
        435
```

<210> SEQ ID NO 27
<211> LENGTH: 1329
<212> TYPE: DNA
<213> ORGANISM: Chryseobacterium sp.

<400> SEQUENCE: 27

```
atgaacactt taacaggtac aaaagagttt tttacaggta ttgaaaaaat taagtttgag     60

gggaaggaaa gcaggaatcc gttggcattc cgttattatg atgctgaaaa gatcgtaatg    120

ggaaaaccaa tgaaagactg gaccagattt gcaatggcat ggtggcatac cttatgtgca    180

aacggaagcg atccattcgg aggacctact atccaccacc catgggatat cggaaatgat    240

cctgtgacca gagcaatgca taagatggat gcaggctttg aattcatgtc taaaatgggc    300

ttcaattatt actgtttcca tgatatcgat ttggtagacc ccgccaataa ttggaaagac    360

tatgagaaga atatgcagac tattgtggag tatgcaaaac aaaagcagaa ggaaacagga    420

attaaacttt tatggggaac agcaaatgtt ttcacgcatg aaagatacat gaatggagct    480

tctaccaatc ccaattttga tgttgtagcc tgcgcaggaa cccaggtgaa aaattcaata    540

gatgccacca ttgcacttgg aggtgaaaac tatgttttct ggggtggaag agaaggatat    600

atgagtcttt taaataccga tatgaagcgt gaaaaagatc atctggcccg tttcctttcc    660

atgtcgagag attatgcccg tcagcaagga tttaaaggaa ctttccttat tgaacctaaa    720

ccaatggagc ctaccaaaca tcagtatgat tatgactctg aaaccgtaat cggattcctg    780

agacactatg gactagacaa agactttaaa ctgaatatcg aagtgaatca tgctacattg    840

gcaggtcata catttgaaca tgaacttcag gttgctgttg atgcagggct tttaggaagt    900

attgatgcga acagaggaga ttatcaaaac ggctgggata cggatcagtt tccgatcgat    960

tattatgata tggttcaggc atggttggta ctgcttccgg caggaggtct gggaaccgga   1020

ggcgtaaact ttgatgccaa aatcagaaga aattctattg atgctgaaga tttattcatt   1080

tctcatattt caggaatgga tgtattcgct aaaggtcttc ttgcggcagc ggatattttt   1140

gaaaattcgg attacaaaaa actgaaaaca aaccgttatg cttcttttga taacggaagt   1200

ggaaaagcat tcgaggaagg tacgcttacc ttggaagatc ttcagagaat tgctcacgaa   1260

ataggcgaac cacagccaaa aagcggaaaa caggaactgt ttgaggccat cgtgaatatg   1320

tatatataa                                                           1329
```

<210> SEQ ID NO 28
<211> LENGTH: 442
<212> TYPE: PRT
<213> ORGANISM: Chryseobacterium sp.

<400> SEQUENCE: 28

```
Met Asn Thr Leu Thr Gly Thr Lys Glu Phe Phe Thr Gly Ile Glu Lys
1               5                   10                  15

Ile Lys Phe Glu Gly Lys Glu Ser Arg Asn Pro Leu Ala Phe Arg Tyr
            20                  25                  30

Tyr Asp Ala Glu Lys Ile Val Met Gly Lys Pro Met Lys Asp Trp Thr
        35                  40                  45

Arg Phe Ala Met Ala Trp Trp His Thr Leu Cys Ala Asn Gly Ser Asp
    50                  55                  60

Pro Phe Gly Gly Pro Thr Ile His His Pro Trp Asp Ile Gly Asn Asp
65                  70                  75                  80

Pro Val Thr Arg Ala Met His Lys Met Asp Ala Gly Phe Glu Phe Met
                85                  90                  95

Ser Lys Met Gly Phe Asn Tyr Tyr Cys Phe His Asp Ile Asp Leu Val
            100                 105                 110

Asp Pro Ala Asn Asn Trp Lys Asp Tyr Glu Lys Asn Met Gln Thr Ile
        115                 120                 125
```

```
Val Glu Tyr Ala Lys Gln Lys Gln Lys Glu Thr Gly Ile Lys Leu Leu
    130                 135                 140

Trp Gly Thr Ala Asn Val Phe Thr His Glu Arg Tyr Met Asn Gly Ala
145                 150                 155                 160

Ser Thr Asn Pro Asn Phe Asp Val Val Ala Cys Ala Gly Thr Gln Val
                165                 170                 175

Lys Asn Ser Ile Asp Ala Thr Ile Ala Leu Gly Gly Glu Asn Tyr Val
            180                 185                 190

Phe Trp Gly Gly Arg Glu Gly Tyr Met Ser Leu Leu Asn Thr Asp Met
        195                 200                 205

Lys Arg Glu Lys Asp His Leu Ala Arg Phe Leu Ser Met Ser Arg Asp
    210                 215                 220

Tyr Ala Arg Gln Gln Gly Phe Lys Gly Thr Phe Leu Ile Glu Pro Lys
225                 230                 235                 240

Pro Met Glu Pro Thr Lys His Gln Tyr Asp Tyr Asp Ser Glu Thr Val
                245                 250                 255

Ile Gly Phe Leu Arg His Tyr Gly Leu Asp Lys Asp Phe Lys Leu Asn
            260                 265                 270

Ile Glu Val Asn His Ala Thr Leu Ala Gly His Thr Phe Glu His Glu
        275                 280                 285

Leu Gln Val Ala Val Asp Ala Gly Leu Leu Gly Ser Ile Asp Ala Asn
    290                 295                 300

Arg Gly Asp Tyr Gln Asn Gly Trp Asp Thr Asp Gln Phe Pro Ile Asp
305                 310                 315                 320

Tyr Tyr Asp Met Val Gln Ala Trp Leu Val Leu Leu Pro Ala Gly Gly
                325                 330                 335

Leu Gly Thr Gly Gly Val Asn Phe Asp Ala Lys Ile Arg Arg Asn Ser
            340                 345                 350

Ile Asp Ala Glu Asp Leu Phe Ile Ser His Ile Ser Gly Met Asp Val
        355                 360                 365

Phe Ala Lys Gly Leu Leu Ala Ala Ala Asp Ile Phe Glu Asn Ser Asp
    370                 375                 380

Tyr Lys Lys Leu Lys Thr Asn Arg Tyr Ala Ser Phe Asp Asn Gly Ser
385                 390                 395                 400

Gly Lys Ala Phe Glu Glu Gly Thr Leu Thr Leu Glu Asp Leu Gln Arg
                405                 410                 415

Ile Ala His Glu Ile Gly Glu Pro Gln Pro Lys Ser Gly Lys Gln Glu
            420                 425                 430

Leu Phe Glu Ala Ile Val Asn Met Tyr Ile
        435                 440
```

<210> SEQ ID NO 29
<211> LENGTH: 39
<212> TYPE: DNA
<213> ORGANISM: Artificial Sequence
<220> FEATURE:
<223> OTHER INFORMATION: CJ5_pTDH3_fwd

<400> SEQUENCE: 29
atatcgaatt cctgcagccc acagtttatt cctggcatc 39

<210> SEQ ID NO 30
<211> LENGTH: 35
<212> TYPE: DNA
<213> ORGANISM: Artificial Sequence
<220> FEATURE:
<223> OTHER INFORMATION: CJ6_pTDH3_rev

<400> SEQUENCE: 30
aacacaacat tttgtttgtt tatgtgtgtt tattc 35

<210> SEQ ID NO 31
<211> LENGTH: 31
<212> TYPE: DNA
<213> ORGANISM: Artificial Sequence
<220> FEATURE:
<223> OTHER INFORMATION: CJ7_XKS1_fwd

<400> SEQUENCE: 31
aacaaacaaa atgttgtgtt cagtaattca g 31

<210> SEQ ID NO 32
<211> LENGTH: 31
<212> TYPE: DNA
<213> ORGANISM: Artificial Sequence
<220> FEATURE:
<223> OTHER INFORMATION: CJ8_XKS1_rev

<400> SEQUENCE: 32
tcttacttta ttagatgaga gtcttttcca g 31

<210> SEQ ID NO 33
<211> LENGTH: 31
<212> TYPE: DNA
<213> ORGANISM: Artificial Sequence
<220> FEATURE:
<223> OTHER INFORMATION: CJ9_tDIT1_fwd

<400> SEQUENCE: 33
tctcatctaa taaagtaaga gcgctacatt g 31

<210> SEQ ID NO 34
<211> LENGTH: 46
<212> TYPE: DNA
<213> ORGANISM: Artificial Sequence
<220> FEATURE:
<223> OTHER INFORMATION: CJ10_tDIT1_rev

<400> SEQUENCE: 34
ctagaactag tggatccccc gaaattcaaa atatcatctt tgacag 46

<210> SEQ ID NO 35
<211> LENGTH: 41
<212> TYPE: DNA
<213> ORGANISM: Artificial Sequence
<220> FEATURE:
<223> OTHER INFORMATION: CJ11_pPGK1_fwd

<400> SEQUENCE: 35
atatcgaatt cctgcagccc tgtttgcaaa aagaacaaaa c 41

<210> SEQ ID NO 36
<211> LENGTH: 44
<212> TYPE: DNA
<213> ORGANISM: Artificial Sequence
<220> FEATURE:
<223> OTHER INFORMATION: CJ12_pPGK1_rev

<400> SEQUENCE: 36
gttcagacat tgttttatat ttgttgtaaa aagtagataa ttac 44

<210> SEQ ID NO 37

<211> LENGTH: 32
<212> TYPE: DNA
<213> ORGANISM: Artificial Sequence
<220> FEATURE:
<223> OTHER INFORMATION: CJ13_TAL1_fwd

<400> SEQUENCE: 37
aatataaaac aatgtctgaa ccagctcaaa ag 32

<210> SEQ ID NO 38
<211> LENGTH: 31
<212> TYPE: DNA
<213> ORGANISM: Artificial Sequence
<220> FEATURE:
<223> OTHER INFORMATION: CJ14_TAL1_rev

<400> SEQUENCE: 38
gtttagaatc ttaagcggta actttctttt c 31

<210> SEQ ID NO 39
<211> LENGTH: 40
<212> TYPE: DNA
<213> ORGANISM: Artificial Sequence
<220> FEATURE:
<223> OTHER INFORMATION: CJ15_tYHI9_fwd

<400> SEQUENCE: 39
taccgcttaa gattctaaac gcatagttgt aaggttgatg 40

<210> SEQ ID NO 40
<211> LENGTH: 38
<212> TYPE: DNA
<213> ORGANISM: Artificial Sequence
<220> FEATURE:
<223> OTHER INFORMATION: CJ16_tYHI9_rev

<400> SEQUENCE: 40
ctagaactag tggatccccc tcaataccgc ctccggcg 38

<210> SEQ ID NO 41
<211> LENGTH: 42
<212> TYPE: DNA
<213> ORGANISM: Artificial Sequence
<220> FEATURE:
<223> OTHER INFORMATION: CJ17_pCYC19_fwd

<400> SEQUENCE: 41
atatcgaatt cctgcagccc acagattggg agattttcat ag 42

<210> SEQ ID NO 42
<211> LENGTH: 34
<212> TYPE: DNA
<213> ORGANISM: Artificial Sequence
<220> FEATURE:
<223> OTHER INFORMATION: CJ18_pCYC19_rev

<400> SEQUENCE: 42
attgagtcat tgtgatgatg ttttatttgt tttg 34

<210> SEQ ID NO 43
<211> LENGTH: 32
<212> TYPE: DNA
<213> ORGANISM: Artificial Sequence
<220> FEATURE:
<223> OTHER INFORMATION: CJ19_TKL1_fwd

<400> SEQUENCE: 43
catcatcaca atgactcaat tcactgacat tg 32

<210> SEQ ID NO 44
<211> LENGTH: 33
<212> TYPE: DNA
<213> ORGANISM: Artificial Sequence
<220> FEATURE:
<223> OTHER INFORMATION: CJ20_TKL1_rev

<400> SEQUENCE: 44
cagatcaaag ttagaaagct tttttcaaag gag 33

<210> SEQ ID NO 45
<211> LENGTH: 39
<212> TYPE: DNA
<213> ORGANISM: Artificial Sequence
<220> FEATURE:
<223> OTHER INFORMATION: CJ21_tEFM1_fwd

<400> SEQUENCE: 45
agctttctaa ctttgatctg tagcctaagt ataaaattc 39

<210> SEQ ID NO 46
<211> LENGTH: 50
<212> TYPE: DNA
<213> ORGANISM: Artificial Sequence
<220> FEATURE:
<223> OTHER INFORMATION: CJ22_tEFM1_rev

<400> SEQUENCE: 46
ctagaactag tggatccccc tagataatat cattggccta ttatcaaatg 50

<210> SEQ ID NO 47
<211> LENGTH: 49
<212> TYPE: DNA
<213> ORGANISM: Artificial Sequence
<220> FEATURE:
<223> OTHER INFORMATION: CJ23_pPFK1_fwd

<400> SEQUENCE: 47
atatcgaatt cctgcagccc gaaaaatata aggatgagaa agtgaaatc 49

<210> SEQ ID NO 48
<211> LENGTH: 48
<212> TYPE: DNA
<213> ORGANISM: Artificial Sequence
<220> FEATURE:
<223> OTHER INFORMATION: CJ24_pPFK1_rev

<400> SEQUENCE: 48
actgtgccat ctttgatatg attttgtttc agattttta tataaaag 48

<210> SEQ ID NO 49
<211> LENGTH: 28
<212> TYPE: DNA
<213> ORGANISM: Artificial Sequence
<220> FEATURE:
<223> OTHER INFORMATION: CJ25_TKL2_fwd

<400> SEQUENCE: 49
catatcaaag atggcacagt tctccgac 28

<210> SEQ ID NO 50
<211> LENGTH: 31
<212> TYPE: DNA

<213> ORGANISM: Artificial Sequence
<220> FEATURE:
<223> OTHER INFORMATION: CJ26_TKL2_rev

<400> SEQUENCE: 50
atcaaccagc ttagaaagct cttcccatag g 31

<210> SEQ ID NO 51
<211> LENGTH: 39
<212> TYPE: DNA
<213> ORGANISM: Artificial Sequence
<220> FEATURE:
<223> OTHER INFORMATION: CJ27_tRPL15A_fwd

<400> SEQUENCE: 51
agctttctaa gctggttgat ggaaaatata attttattg 39

<210> SEQ ID NO 52
<211> LENGTH: 43
<212> TYPE: DNA
<213> ORGANISM: Artificial Sequence
<220> FEATURE:
<223> OTHER INFORMATION: CJ28_tRPL15A_rev

<400> SEQUENCE: 52
ctagaactag tggatccccc gcttgatagc agaataaaag tac 43

<210> SEQ ID NO 53
<211> LENGTH: 55
<212> TYPE: DNA
<213> ORGANISM: Artificial Sequence
<220> FEATURE:
<223> OTHER INFORMATION: CJ29_module_TKL1_fwd

<400> SEQUENCE: 53
gcttgatatc gaattcctgc agccctagat aatatcattg gcctattatc aaatg 55

<210> SEQ ID NO 54
<211> LENGTH: 35
<212> TYPE: DNA
<213> ORGANISM: Artificial Sequence
<220> FEATURE:
<223> OTHER INFORMATION: CJ30_module_TKL1_rev

<400> SEQUENCE: 54
aggaataaac tgtacagatt gggagatttt catag 35

<210> SEQ ID NO 55
<211> LENGTH: 32
<212> TYPE: DNA
<213> ORGANISM: Artificial Sequence
<220> FEATURE:
<223> OTHER INFORMATION: CJ31_module_XKS1_fwd

<400> SEQUENCE: 55
tctcccaatc tgtacagttt attcctggca tc 32

<210> SEQ ID NO 56
<211> LENGTH: 51
<212> TYPE: DNA
<213> ORGANISM: Artificial Sequence
<220> FEATURE:
<223> OTHER INFORMATION: CJ32_module_XKS1_rev

<400> SEQUENCE: 56
ccgctctaga actagtggat cccccgaaat tcaaaatatc atctttgaca g 51

<210> SEQ ID NO 57
<211> LENGTH: 43
<212> TYPE: DNA
<213> ORGANISM: Artificial Sequence
<220> FEATURE:
<223> OTHER INFORMATION: CJ33_module_TAL1_fwd

<400> SEQUENCE: 57
gcttgatatc gaattcctgc agccctcaat accgcctccg gcg 43

<210> SEQ ID NO 58
<211> LENGTH: 44
<212> TYPE: DNA
<213> ORGANISM: Artificial Sequence
<220> FEATURE:
<223> OTHER INFORMATION: CJ34_module_TAL1_rev

<400> SEQUENCE: 58
ccttatattt ttctgtttgc aaaaagaaca aaactgaaaa aacc 44

<210> SEQ ID NO 59
<211> LENGTH: 42
<212> TYPE: DNA
<213> ORGANISM: Artificial Sequence
<220> FEATURE:
<223> OTHER INFORMATION: CJ35_module_TKL2_fwd

<400> SEQUENCE: 59
ctttttgcaa acagaaaaat ataaggatga gaaagtgaaa tc 42

<210> SEQ ID NO 60
<211> LENGTH: 48
<212> TYPE: DNA
<213> ORGANISM: Artificial Sequence
<220> FEATURE:
<223> OTHER INFORMATION: CJ36_module_TKL2_rev

<400> SEQUENCE: 60
ccgctctaga actagtggat cccccgcttg atagcagaat aaaagtac 48

<210> SEQ ID NO 61
<211> LENGTH: 55
<212> TYPE: DNA
<213> ORGANISM: Artificial Sequence
<220> FEATURE:
<223> OTHER INFORMATION: CJ39_mTKL1-mXKS1_fwd

<400> SEQUENCE: 61
gcttgatatc gaattcctgc agccctagat aatatcattg gcctattatc aaatg 55

<210> SEQ ID NO 62
<211> LENGTH: 39
<212> TYPE: DNA
<213> ORGANISM: Artificial Sequence
<220> FEATURE:
<223> OTHER INFORMATION: CJ40_mTKL1-mXKS1_rev

<400> SEQUENCE: 62
ctccatgtcg ctggaaattc aaaatatcat ctttgacag 39

<210> SEQ ID NO 63
<211> LENGTH: 31
<212> TYPE: DNA
<213> ORGANISM: Artificial Sequence
<220> FEATURE:

<223> OTHER INFORMATION: CJ41_KANMX6_fwd

<400> SEQUENCE: 63
tattttgaat ttccagcgac atggaggccc a 31

<210> SEQ ID NO 64
<211> LENGTH: 31
<212> TYPE: DNA
<213> ORGANISM: Artificial Sequence
<220> FEATURE:
<223> OTHER INFORMATION: CJ42_KANMX6_rev

<400> SEQUENCE: 64
gaggcggtat tgatcgacac tggatggcgg c 31

<210> SEQ ID NO 65
<211> LENGTH: 31
<212> TYPE: DNA
<213> ORGANISM: Artificial Sequence
<220> FEATURE:
<223> OTHER INFORMATION: CJ43_mTKL2-mTAL1_fwd

<400> SEQUENCE: 65
catccagtgt cgatcaatac cgcctccggc g 31

<210> SEQ ID NO 66
<211> LENGTH: 53
<212> TYPE: DNA
<213> ORGANISM: Artificial Sequence
<220> FEATURE:
<223> OTHER INFORMATION: CJ44_mTKL2-mTAL1_rev

<400> SEQUENCE: 66
ccgctctaga actagtggat cccccgcttg atagcagaat aaaagtacag ctc 53

<210> SEQ ID NO 67
<211> LENGTH: 43
<212> TYPE: DNA
<213> ORGANISM: Artificial Sequence
<220> FEATURE:
<223> OTHER INFORMATION: CJ49_PPP-KAN_fwd

<400> SEQUENCE: 67
cctgcaaatc gtgtagataa tatcattggc ctattatcaa atg 43

<210> SEQ ID NO 68
<211> LENGTH: 36
<212> TYPE: DNA
<213> ORGANISM: Artificial Sequence
<220> FEATURE:
<223> OTHER INFORMATION: CJ50_PPP-KAN_rev

<400> SEQUENCE: 68
ttgataaatt actgcttgat agcagaataa aagtac 36

<210> SEQ ID NO 69
<211> LENGTH: 51
<212> TYPE: DNA
<213> ORGANISM: Artificial Sequence
<220> FEATURE:
<223> OTHER INFORMATION: CJ53_CHR16-UP-1000_fwd

<400> SEQUENCE: 69
gcttgatatc gaattcctgc agcccgagaa tagaatacgt gtctataggt g 51

<210> SEQ ID NO 70
<211> LENGTH: 35
<212> TYPE: DNA
<213> ORGANISM: Artificial Sequence
<220> FEATURE:
<223> OTHER INFORMATION: CJ54_CHR16-UP-1000_rev

<400> SEQUENCE: 70
atgatattat ctacacgatt tgcaggacag tttac 35

<210> SEQ ID NO 71
<211> LENGTH: 41
<212> TYPE: DNA
<213> ORGANISM: Artificial Sequence
<220> FEATURE:
<223> OTHER INFORMATION: CJ55_CHR16_DOWN-1000_fwd

<400> SEQUENCE: 71
tctgctatca agcagtaatt tatcaagctt taataagttt g 41

<210> SEQ ID NO 72
<211> LENGTH: 44
<212> TYPE: DNA
<213> ORGANISM: Artificial Sequence
<220> FEATURE:
<223> OTHER INFORMATION: CJ56_CHR16_DOWN-1000_rev

<400> SEQUENCE: 72
ccgctctaga actagtggat cccccctggtt tagaatcctg aacc 44

<210> SEQ ID NO 73
<211> LENGTH: 500
<212> TYPE: DNA
<213> ORGANISM: Saccharomyces cerevisae

<400> SEQUENCE: 73
acagtttatt cctggcatcc actaaatata atggagcccg ctttttaagc tggcatccag 60
aaaaaaaaag aatcccagca ccaaaatatt gttttcttca ccaaccatca gttcataggt 120
ccattctctt agcgcaacta cagagaacag gggcacaaac aggcaaaaaa cgggcacaac 180
ctcaatggag tgatgcaacc tgcctggagt aaatgatgac acaaggcaat tgacccacgc 240
atgtatctat ctcattttct tacaccttct attaccttct gctctctctg atttggaaaa 300
agctgaaaaa aaaggttgaa accagttccc tgaaattatt cccctacttg actaataagt 360
atataaagac ggtaggtatt gattgtaatt ctgtaaatct atttcttaaa cttcttaaat 420
tctactttta tagttagtct ttttttagt tttaaaacac caagaactta gtttcgaata 480
aacacacata aacaaacaaa 500

<210> SEQ ID NO 74
<211> LENGTH: 1803
<212> TYPE: DNA
<213> ORGANISM: Saccharomyces cerevisae

<400> SEQUENCE: 74
atgttgtgtt cagtaattca gagacagaca agagaggttt ccaacacaat gtctttagac 60
tcatactatc ttgggtttga tctttcgacc caacaactga aatgtctcgc cattaaccag 120
gacctaaaaa ttgtccattc agaaacagtg gaatttgaaa aggatcttcc gcattatcac 180
acaaagaagg gtgtctatat acacggcgac actatcgaat gtcccgtagc catgtggtta 240
gaggctctag atctggttct ctcgaaatat cgcgaggcta aatttccatt gaacaaagtt 300

```
atggccgtct cagggtcctg ccagcagcac gggtctgtct actggtcctc ccaagccgaa    360

tctctgttag agcaattgaa taagaaaccg gaaaaagatt tattgcacta cgtgagctct    420

gtagcatttg caaggcaaac cgcccccaat tggcaagacc acagtactgc aaagcaatgt    480

caagagtttg aagagtgcat aggtgggcct gaaaaaatgg ctcaattaac agggtccaga    540

gcccatttta gatttactgg tcctcaaatt ctgaaaattg cacaattaga accagaagct    600

tacgaaaaaa caaagaccat ttctttagtg tctaattttt tgacttctat cttagtgggc    660

catcttgttg aattagagga ggcagatgcc tgtggtatga acctttatga tatacgtgaa    720

agaaaattca gtgatgagct actacatcta attgatagtt cttctaagga taaaactatc    780

agacaaaaat taatgagagc acccatgaaa aatttgatag cgggtaccat ctgtaaatat    840

tttattgaga agtacggttt caatacaaac tgcaaggtct ctcccatgac tggggataat    900

ttagccacta tatgttcttt accccctgcgg aagaatgacg ttctcgtttc cctaggaaca    960

agtactacag ttcttctggt caccgataag tatcacccct ctccgaacta tcatcttttc   1020

attcatccaa ctctgccaaa ccattatatg ggtatgattt gttattgtaa tggttctttg   1080

gcaagggaga ggataagaga cgagttaaac aaagaacggg aaaataatta tgagaagact   1140

aacgattgga ctctttttaa tcaagctgtg ctagatgact cagaaagtag tgaaaatgaa   1200

ttaggtgtat attttcctct gggggagatc gttcctagcg taaaagccat aaacaaaagg   1260

gttatcttca atccaaaaac gggtatgatt gaaagagagg tggccaagtt caaagacaag   1320

aggcacgatg ccaaaaatat tgtagaatca caggctttaa gttgcagggt aagaatatct   1380

cccctgcttt cggattcaaa cgcaagctca caacagagac tgaacgaaga tacaatcgtg   1440

aagtttgatt acgatgaatc tccgctgcgg gactacctaa ataaaaggcc agaaaggact   1500

ttttttgtag gtggggcttc taaaaacgat gctattgtga agaagtttgc tcaagtcatt   1560

ggtgctacaa agggtaattt taggctagaa acaccaaact catgtgccct tggtggttgt   1620

tataaggcca tgtggtcatt gttatatgac tctaataaaa ttgcagttcc ttttgataaa   1680

tttctgaatg acaattttcc atggcatgta atggaaagca tatccgatgt ggataatgaa   1740

aattgggatc gctataattc caagattgtc cccttaagcg aactggaaaa gactctcatc   1800

taa                                                                 1803
```

<210> SEQ ID NO 75
<211> LENGTH: 300
<212> TYPE: DNA
<213> ORGANISM: Saccharomyces cerevisae

<400> SEQUENCE: 75

```
taaagtaaga gcgctacatt ggtctacctt tttgttcttt tacttaaaca ttagttagtt     60

cgttttcttt ttctcatttt tttatgtttc ccccccaaag ttctgatttt ataatatttt    120

atttcacaca attccattta acagaggggg aatagattct ttagcttaga aaattagtga    180

tcaatatata tttgcctttc ttttcatctt ttcagtgata ttaatggttt cgagacactg    240

caatggccct agttgtctaa gaggatagat gttactgtca aagatgatat tttgaatttc    300
```

<210> SEQ ID NO 76
<211> LENGTH: 500
<212> TYPE: DNA
<213> ORGANISM: Saccharomyces cerevisae

<400> SEQUENCE: 76

```
tgtttgcaaa aagaacaaaa ctgaaaaaac ccagacacgc tcgacttcct gtcttcctat     60
```

```
tgattgcagc ttccaatttc gtcacacaac aaggtcctag cgacggctca caggttttgt    120

aacaagcaat cgaaggttct ggaatggcgg gaaagggttt agtaccacat gctatgatgc    180

ccactgtgat ctccagagca aagttcgttc gatcgtactg ttactctctc tctttcaaac    240

agaattgtcc gaatcgtgtg acaacaacag cctgttctca cacactcttt tcttctaacc    300

aagggggtgg tttagtttag tagaacctcg tgaaacttac atttacatat atataaactt    360

gcataaattg gtcaatgcaa gaaatacata tttggtcttt tctaattcgt agtttttcaa    420

gttcttagat gctttctttt tctctttttt acagatcatc aaggaagtaa ttatctactt    480

tttacaacaa atataaaaca                                                500


<210> SEQ ID NO 77
<211> LENGTH: 1008
<212> TYPE: DNA
<213> ORGANISM: Saccharomyces cerevisae

<400> SEQUENCE: 77

atgtctgaac cagctcaaaa gaaacaaaag gttgctaaca actctctaga acaattgaaa     60

gcctccggca ctgtcgttgt tgccgacact ggtgatttcg gctctattgc caagtttcaa    120

cctcaagact ccacaactaa cccatcattg atcttggctg ctgccaagca accaacttac    180

gccaagttga tcgatgttgc cgtggaatac ggtaagaagc atggtaagac caccgaagaa    240

caagtcgaaa atgctgtgga cagattgtta gtcgaattcg gtaaggagat cttaaagatt    300

gttccaggca gagtctccac cgaagttgat gctagattgt cttttgacac tcaagctacc    360

attgaaaagg ctagacatat cattaaattg tttgaacaag aaggtgtctc caaggaaaga    420

gtccttatta aaattgcttc cacttgggaa ggtattcaag ctgccaaaga attggaagaa    480

aaggacggta tccactgtaa tttgactcta ttattctcct tcgttcaagc agttgcctgt    540

gccgaggccc aagttacttt gatttcccca tttgttggta gaattctaga ctggtacaaa    600

tccagcactg gtaaagatta caagggtgaa gccgacccag gtgttatttc cgtcaagaaa    660

atctacaact actacaagaa gtacggttac aagactattg ttatgggtgc ttctttcaga    720

agcactgacg aaatcaaaaa cttggctggt gttgactatc taacaatttc tccagcttta    780

ttggacaagt tgatgaacag tactgaacct ttcccaagag ttttggaccc tgtctccgct    840

aagaaggaag ccggcgacaa gatttcttac atcagcgacg aatctaaatt cagattcgac    900

ttgaatgaag acgctatggc cactgaaaaa ttgtccgaag gtatcagaaa attctctgcc    960

gatattgtta ctctattcga cttgattgaa aagaaagtta ccgcttaa                1008


<210> SEQ ID NO 78
<211> LENGTH: 120
<212> TYPE: DNA
<213> ORGANISM: Saccharomyces cerevisae

<400> SEQUENCE: 78

gattctaaac gcatagttgt aaggttgatg tatatatata tatatatatg tatatattaa     60

ttacaataat atgctcccgc ccaaattttt ctccttcaat accgccggag gcggtattga    120


<210> SEQ ID NO 79
<211> LENGTH: 500
<212> TYPE: DNA
<213> ORGANISM: Saccharomyces cerevisae

<400> SEQUENCE: 79
```

```
acagattggg agattttcat agtagaattc agcatgatag ctacgtaaat gtgttccgca     60
ccgtcacaaa gtgttttcta ctgttctttc ttctttcgtt cattcagttg agttgagtga    120
gtgctttgtt caatggatct tagctaaaat gcatattttt tctcttggta aatgaatgct    180
tgtgatgtct tccaagtgat ttcctttcct tcccatatga tgctaggtac ctttagtgtc    240
ttcctaaaaa aaaaaaaagg ctcgccatca aaacgatatt cgttggcttt tttttctgaa    300
ttataaatac tctttggtaa cttttcattt ccaagaacct cttttttcca gttatatcat    360
ggtccccttt caaagttatt ctctactctt tttcatattc attctttttc atcctttggt    420
tttttattct taacttgttt attattctct cttgtttcta tttacaagac accaatcaaa    480
acaaataaaa catcatcaca                                                500
```

```
<210> SEQ ID NO 80
<211> LENGTH: 2043
<212> TYPE: DNA
<213> ORGANISM: Saccharomyces cerevisae

<400> SEQUENCE: 80

atgactcaat tcactgacat tgataagcta gccgtctcca ccataagaat tttggctgtg     60
gacaccgtat ccaaggccaa ctcaggtcac ccaggtgctc cattgggtat ggcaccagct    120
gcacacgttc tatggagtca aatgcgcatg aacccaacca acccagactg gatcaacaga    180
gatagatttg tcttgtctaa cggtcacgcg gtcgctttgt tgtattctat gctacatttg    240
actggttacg atctgtctat tgaagacttg aaacagttca gacagttggg ttccagaaca    300
ccaggtcatc ctgaatttga gttgccaggt gttgaagtta ctaccggtcc attaggtcaa    360
ggtatctcca acgctgttgg tatggccatg gctcaagcta acctggctgc cacttacaac    420
aagccgggct ttaccttgtc tgacaactac acctatgttt tcttgggtga cggttgtttg    480
caagaaggta tttcttcaga agcttcctcc ttggctggtc atttgaaatt gggtaacttg    540
attgccatct acgatgacaa caagatcact atcgatggtg ctaccagtat ctcattcgat    600
gaagatgttg ctaagagata cgaagcctac ggttgggaag ttttgtacgt agaaaatggt    660
aacgaagatc tagccggtat tgccaaggct attgctcaag ctaagttatc caaggacaaa    720
ccaactttga tcaaaatgac cacaaccatt ggttacggtt ccttgcatgc cggctctcac    780
tctgtgcacg gtgccccatt gaaagcagat gatgttaaac aactaaagag caaattcggt    840
ttcaacccag acaagtcctt tgttgttcca caagaagttt acgaccacta ccaaaagaca    900
attttaaagc caggtgtcga agccaacaac aagtggaaca agttgttcag cgaataccaa    960
aagaaattcc cagaattagg tgctgaattg gctagaagat tgagcggcca actacccgca   1020
aattgggaat ctaagttgcc aacttacacc gccaaggact ctgccgtggc cactagaaaa   1080
ttatcagaaa ctgttcttga ggatgtttac aatcaattgc cagagttgat tggtggttct   1140
gccgatttaa caccttctaa cttgaccaga tggaaggaag cccttgactt ccaacctcct   1200
tcttccggtt caggtaacta ctctggtaga tacattaggt acggtattag agaacacgct   1260
atgggtgcca taatgaacgg tatttcagct ttcggtgcca actacaaacc atacggtggt   1320
actttcttga acttcgtttc ttatgctgct ggtgccgtta gattgtccgc tttgtctggc   1380
cacccagtta tttgggttgc tacacatgac tctatcggtg tcggtgaaga tggtccaaca   1440
catcaaccta ttgaaacttt agcacacttc agatccctac caaacattca agtttggaga   1500
ccagctgatg gtaacgaagt ttctgccgcc tacaagaact ctttagaatc caagcatact   1560
ccaagtatca ttgctttgtc cagacaaaac ttgccacaat tggaaggtag ctctattgaa   1620
```

```
agcgcttcta agggtggtta cgtactacaa gatgttgcta acccagatat tattttagtg   1680

gctactggtt ccgaagtgtc tttgagtgtt gaagctgcta agactttggc cgcaaagaac   1740

atcaaggctc gtgttgtttc tctaccagat ttcttcactt ttgacaaaca acccctagaa   1800

tacagactat cagtcttacc agacaacgtt ccaatcatgt ctgttgaagt tttggctacc   1860

acatgttggg gcaaatacgc tcatcaatcc ttcggtattg acagatttgg tgcctccggt   1920

aaggcaccag aagtcttcaa gttcttcggt ttcaccccag aaggtgttgc tgaaagagct   1980

caaaagacca ttgcattcta taagggtgac aagctaattt ctcctttgaa aaaagctttc   2040

taa                                                                 2043
```

<210> SEQ ID NO 81
<211> LENGTH: 120
<212> TYPE: DNA
<213> ORGANISM: Saccharomyces cerevisae

<400> SEQUENCE: 81

```
ctttgatctg tagcctaagt ataaaattct acgtatgtat atatttacat gcaatttttt     60

ctttttccaa ttcatgttaa tgttcttcat catttgataa taggccaatg atattatcta    120
```

<210> SEQ ID NO 82
<211> LENGTH: 500
<212> TYPE: DNA
<213> ORGANISM: Saccharomyces cerevisae

<400> SEQUENCE: 82

```
gaaaaatata aggatgagaa agtgaaatcg gttttttttt tccattgtcg tcatcaacat     60

gatttttaa ataaataaat acgatttttt atttttttc ccttctttgt ttttgttttg    120

cttattccca tcttcattat taaattcttc cgctcttaat aaaggagttt ttttattatc    180

ttcttgtgta atcatccttt ttctttaatt ttcttccttt tctttttctc tttactggtt    240

tttttacttc tttattctca accatctaaa gaatattatt gctttctacc aataaaatct    300

gttaattcta tttggattgt cgtctactca agtctcgcct agtaaataaa cgataaacaa    360

atttgaagta agaataacaa tatagggaga gaaatttttc tatttttaat ttcgaaacag    420

gtaccaaaaa atctaagttc actttagcac tatttgggaa agcttttata taaaaaatct    480

gaaacaaaat catatcaaag                                                500
```

<210> SEQ ID NO 83
<211> LENGTH: 2046
<212> TYPE: DNA
<213> ORGANISM: Saccharomyces cerevisae

<400> SEQUENCE: 83

```
atggcacagt tctccgacat tgataaactt gcggtttcca ctttaagatt actttccgtt     60

gaccaggtgg aaagcgcaca atctggccac ccaggtgcac cactaggatt ggcaccagtt    120

gcccatgtaa ttttcaagca actgcgctgt aaccctaaca atgaacattg gatcaataga    180

gacaggtttg ttctgtcgaa cggtcactca tgcgctcttc tgtactcaat gctccatcta    240

ttaggatacg attactctat cgaggacttg agacaattta gacaagtaaa ctcaaggaca    300

ccgggtcatc cagaattcca ctcagcggga gtggaaatca cttccggtcc gctaggccag    360

ggtatctcaa atgctgttgg tatggcaata gcgcaggcca actttgccgc cacttataac    420

gaggatggct ttcccatttc cgactcatat acgtttgcta ttgtagggga tggttgctta    480
```

```
caagagggtg tttcttcgga gacctcttcc ttagcgggac atctgcaatt gggtaacttg    540

attacgtttt atgacagtaa tagcatttcc attgacggta aaacctcgta ctcgttcgac    600

gaagatgttt tgaagcgata cgaggcatat ggttgggaag tcatggaagt cgataaagga    660

gacgacgata tggaatccat ttctagcgct ttggaaaagg caaaactatc gaaggacaag    720

ccaaccataa tcaaggtaac tactacaatt ggatttgggt ccctacaaca gggtactgct    780

ggtgttcatg ggtccgcttt gaaggcagat gatgttaaac agttgaagaa gaggtggggg    840

tttgacccaa ataaatcatt tgtagtacct caagaggtgt acgattatta taagaagact    900

gttgtggaac ccggtcaaaa acttaatgag gaatgggata ggatgtttga agaatacaaa    960

accaaatttc ccgagaaggg taaagaattg caaagaagat tgaatggtga gttaccggaa   1020

ggttgggaaa agcatttacc gaagtttact ccggacgacg atgctctggc aacaagaaag   1080

acatcccagc aggtgctgac gaacatggtc caagttttgc ctgaattgat cggtggttct   1140

gccgatttga caccttcgaa tctgacaagg tgggaaggcg cggtagattt ccaacctccc   1200

attacccaac taggtaacta tgcaggaagg tacattagat acggtgtgag ggaacacgga   1260

atgggtgcca ttatgaacgg tatctctgcc tttggtgcaa actacaagcc ttacggtggt   1320

acctttttga acttcgtctc ttatgctgca ggagccgtta ggttagccgc cttgtctggt   1380

aatccagtca tttgggttgc aacacatgac tctatcgggc ttggtgagga tggtccaacg   1440

caccaaccta ttgaaactct ggctcacttg agggctattc caaacatgca tgtatggaga   1500

cctgctgatg gtaacgaaac ttctgctgcg tattattctg ctatcaaatc tggtcgaaca   1560

ccatctgttg tggctttatc acgacagaat cttcctcaat tggagcattc ctcttttgaa   1620

aaagccttga agggtggcta tgtgatccat gacgtggaga atcctgatat tatcctggtg   1680

tcaacaggat cagaagtctc catttctata gatgcagcca aaaaattgta cgatactaaa   1740

aaaatcaaag caagagttgt ttccctgcca gacttttata cttttgacag gcaaagtgaa   1800

gaatacagat tctctgttct accagacggt gttccgatca tgtcctttga agtattggct   1860

acttcaagct ggggtaagta tgctcatcaa tcgttcggac tcgacgaatt tggtcgttca   1920

ggcaaggggc ctgaaattta caaattgttc gatttcacag cggacggtgt tgcgtcaagg   1980

gctgaaaaga caatcaatta ctacaaagga aagcagttgc tttctcctat gggaagagct   2040

ttctaa                                                              2046
```

```
<210> SEQ ID NO 84
<211> LENGTH: 168
<212> TYPE: DNA
<213> ORGANISM: Saccharomyces cerevisae

<400> SEQUENCE: 84

gctggttgat ggaaaatata attttattgg gcaaactttt gtttatctga tgtgttttat     60

actattatct ttttaattaa tgattctata tacaaacctg tatatttttt ctttaaccaa    120

ttttttttt tatagaccta gagctgtact tttattctgc tatcaagc                  168
```

```
<210> SEQ ID NO 85
<211> LENGTH: 348
<212> TYPE: DNA
<213> ORGANISM: Saccharomyces cerevisae

<400> SEQUENCE: 85

cagcgacatg gaggcccaga ataccctcct tgacagtctt gacgtgcgca gctcaggggc     60

atgatgtgac tgtcgcccgt acatttagcc catacatccc catgtataat catttgcatc    120
```

```
catacatttt gatggccgca cggcgcgaag caaaaattac ggctcctcgc tgcagacctg    180

cgagcaggga aacgctcccc tcacagacgc gttgaattgt ccccacgccg cgcccctgta    240

gagaaatata aaaggttagg atttgccact gaggttcttc tttcatatac ttccttttaa    300

aatcttgcta ggatacagtt ctcacatcac atccgaacat aaacaacc                348
```

<210> SEQ ID NO 86
<211> LENGTH: 810
<212> TYPE: DNA
<213> ORGANISM: Saccharomyces cerevisae

<400> SEQUENCE: 86

```
atgggtaagg aaaagactca cgtttcgagg ccgcgattaa attccaacat ggatgctgat     60

ttatatgggt ataaatgggc tcgcgataat gtcgggcaat caggtgcgac aatctatcga    120

ttgtatggga agcccgatgc gccagagttg tttctgaaac atggcaaagg tagcgttgcc    180

aatgatgtta cagatgagat ggtcagacta aactggctga cggaatttat gcctcttccg    240

accatcaagc attttatccg tactcctgat gatgcatggt tactcaccac tgcgatcccc    300

ggcaaaacag cattccaggt attagaagaa tatcctgatt caggtgaaaa tattgttgat    360

gcgctggcag tgttcctgcg ccggttgcat tcgattcctg tttgtaattg tccttttaac    420

agcgatcgcg tatttcgtct cgctcaggcg caatcacgaa tgaataacgg tttggttgat    480

gcgagtgatt ttgatgacga gcgtaatggc tggcctgttg aacaagtctg gaaagaaatg    540

cataagcttt tgccattctc accggattca gtcgtcactc atggtgattt ctcacttgat    600

aaccttattt ttgacgaggg gaaattaata ggttgtattg atgttggacg agtcggaatc    660

gcagaccgat accaggatct tgccatccta tggaactgcc tcggtgagtt ttctccttca    720

ttacagaaac ggctttttca aaaatatggt attgataatc ctgatatgaa taaattgcag    780

tttcatttga tgctcgatga gtttttctaa                                     810
```

<210> SEQ ID NO 87
<211> LENGTH: 240
<212> TYPE: DNA
<213> ORGANISM: Saccharomyces cerevisae

<400> SEQUENCE: 87

```
tcagtactga caataaaaag attcttgttt tcaagaactt gtcatttgta tagttttttt     60

atattgtagt tgttctattt taatcaaatg ttagcgtgat ttatattttt tttcgcctcg    120

acatcatctg cccagatgcg aagttaagtg cgcagaaagt aatatcatgc gtcaatcgta    180

tgtgaatgct ggtcgctata ctgctgtcga ttcgatacta acgccgccat ccagtgtcga    240
```

<210> SEQ ID NO 88
<211> LENGTH: 1000
<212> TYPE: DNA
<213> ORGANISM: Saccharomyces cerevisae

<400> SEQUENCE: 88

```
gagaatagaa tacgtgtcta taggtgctac tatgtgatta agaggttgca aagtgaaagg     60

cagtatttga ttcctgcaag gatcttccgt gcaggacaat agggtttaat gccacattgt    120

actctgcgtg ctatgcgaat aaaggaagcg cacgccgaat ctgaaatagg caatttggta    180

caaaaatcac gttattccat taagcagagg cagttcatat tactttggcc tgtcttacga    240

atgttcttct gaatacccaa ttctcctgag aacatctatc atataatttt tgagtttagg    300
```

```
cagacttgag gaaaaagtgg gttttgaggt ggttgtttgg agtctatctc tgataagaat    360

ggctttattg catatattct aacaggccct ctcgtaggta aaggaatccc caaaaaagag    420

tgggcagctt tacatggtaa aattacaatt cgttctttcg tttcacacgt cggcacttac    480

tatcctatta cattattaat ccttacattt cagcttccac taaattcgat ggccgtttct    540

cgtcatttat gtgatatcat aacaccatat atggcagtac atcaggcata agcactaatc    600

cgtagaaatt agttgatccc aagtttaacg gactcgaagt cctgttaatt atgtgagccg    660

aagcgtagga atattaatgt aatagaatca ataaatgact gtatattaaa acgaagaacg    720

aaagaatttt accactttgt aaaatattag attgcgttga ggggcttgtg gtcacctgtc    780

ataggatgcc tatgttcccc ccaaaaattt aattctgaag taagtttttg ttgagtactt    840

caactttatt tccttcaatt gtgaaatgtt gataactagc atctattact atccgataac    900

gccaggcgcc tttatatcat ataattaaga cacaaaagga taaaacaaag gtgttaacta    960

ttctgcatac tcactatcgt aaactgtcct gcaaatcgtg                          1000
```

<210> SEQ ID NO 89
<211> LENGTH: 1000
<212> TYPE: DNA
<213> ORGANISM: Saccharomyces cerevisae

<400> SEQUENCE: 89

```
agtaatttat caagctttaa taagtttggg tagtttaact gtgcaaaaag gtatttacct     60

tacatactga atcttgtctg tttggtagcg gctgctttat gggtgtttca tagatgtcca    120

aaatatattg agatattgag atataacatt ctaggataat caaaattacc ataattcaaa    180

agctcgtatg gcgcagtggt agcgcagcag attgcaaatc tgttggtcct tagttcgatc    240

ctgagtgcga gctttctttt ttagactact aattttattt tgctagtcat ttttttttta    300

tactcaaaaa gtaaaaagac tacgagtata ttcaaagtaa aaaacgaacg tcaaactatc    360

tcgattaaaa cttgtcatac tgtgggtatc atattctgtg ccctcagtga aaagaaccag    420

caaaagaacg cgcatctcga gtgaagacgc gcccttgatg gtacaaaatt taacgggaag    480

gcgcgtcgtg atgttcacgc gctttgccca cattgggata gcgcccacag catatctgtg    540

ctaaactcac ttttcctagt gactgccgat agctactgcc atctaccgcg aagggaactt    600

catttgcgtt catcggttta ttagaagcta cttggaacta attcttaagc ttctcaagaa    660

aagttttttt tctgtctatc tattgaagtc tttttgtctt tgtacttcaa gagactcaat    720

cacctaaagc ttttcacggc caattagttg tctcacacaa agcaaaataa gcttaataat    780

tagcagtaac gcgcttttcc ctgtatttaa agccgctgaa cacctttact gaacaatggg    840

agagaaccac gaccatgagc agagtattaa aagaaattct atgatttata atgaaaatga    900

gaggcagttg tgcaattcaa acctaaagat tcttcaaaat aaaagggccc tttcaaaaaa    960

tgacagctct agtaagcagc aggttcagga ttctaaacca                          1000
```

<210> SEQ ID NO 90
<211> LENGTH: 391
<212> TYPE: DNA
<213> ORGANISM: Saccharomyces cerevisae

<400> SEQUENCE: 90

```
ctcgtaggaa caatttcggg cccctgcgtg ttcttctgag gttcatcttt tacatttgct     60

tctgctggat aattttcaga ggcaacaagg aaaaattaga tggcaaaaag tcgtctttca    120

aggaaaaatc cccaccatct ttcgagatcc cctgtaactt attggcaact gaaagaatga    180
```

aaaggaggaa aatacaaaat atactagaac tgaaaaaaaa aaagtataaa tagagacgat 240
atatgccaat acttcacaat gttcgaatct attcttcatt tgcagctatt gtaaaataat 300
aaaacatcaa gaacaaacaa gctcaacttg tcttttctaa gaacaaagaa taaacacaaa 360
aacaaaaagt ttttttaatt ttaatcaaaa a 391

<210> SEQ ID NO 91
<211> LENGTH: 248
<212> TYPE: DNA
<213> ORGANISM: Saccharomyces cerevisae

<400> SEQUENCE: 91
tcatgtaatt agttatgtca cgcttacatt cacgccctcc ccccacatcc gctctaaccg 60
aaaaggaagg agttagacaa cctgaagtct aggtccctat ttattttttt atagttatgt 120
tagtattaag aacgttattt atatttcaaa tttttctttt ttttctgtac agacgcgtgt 180
acgcatgtaa cattatactg aaaaccttgc ttgagaaggt tttgggacgc tcgaaggctt 240
taatttgc 248

<210> SEQ ID NO 92
<211> LENGTH: 278
<212> TYPE: DNA
<213> ORGANISM: Saccharomyces cerevisae

<400> SEQUENCE: 92
tcaataccgc ctccggcggt attgaaggag aaaaatttgg gcgggagcat attattgtaa 60
ttaatatata catatatata tatatatata catcaacctt acaactatgc gtttagaatc 120
ttaagcggta actttctttt caatcaagtc gaatagagta acaatatcgg cagagaattt 180
tctgatacct tcggacaatt tttcagtggc catagcgtct tcattcaagt cgaatctgaa 240
tttagattcg tcgctgatgt aagaaatctt gtcgccgg 278

<210> SEQ ID NO 93
<211> LENGTH: 576
<212> TYPE: DNA
<213> ORGANISM: Artificial Sequence
<220> FEATURE:
<223> OTHER INFORMATION: NATR

<400> SEQUENCE: 93
atgggtacca ctcttgacga cacggcttac cggtaccgca ccagtgtccc gggggacgcc 60
gaggccatcg aggcactgga tgggtccttc accaccgaca ccgtcttccg cgtcaccgcc 120
accggggacg gcttcaccct gcgggaggtg ccggtggacc cgcccctgac caaggtgttc 180
cccgacgacg aatcggacga cgaatcggac gacggggagg acggcgaccc ggactcccgg 240
acgttcgtcg cgtacgggga cgacggcgac ctggcgggct tcgtggtcat ctcgtactcg 300
gcgtggaacc gccggctgac cgtcgaggac atcgaggtcg ccccggagca ccgggggcac 360
ggggtcgggc gcgcgttgat ggggctcgcg acggagttcg ccggcgagcg gggcgccggg 420
cacctctggc tggaggtcac caacgtcaac gcaccggcga tccacgcgta ccggcggatg 480
gggttcaccc tctgcggcct ggacaccgcc ctgtacgacg gcaccgcctc ggacggcgag 540
cggcaggcgc tctacatgag catgccctgc ccctaa 576

<210> SEQ ID NO 94
<211> LENGTH: 306
<212> TYPE: DNA

-continued

```
<213> ORGANISM: Saccharomyces cerevisae

<400> SEQUENCE: 94

gcgaatttct tatgatttat gatttttatt attaaataag ttataaaaaa aataagtgta     60

tacaaatttt aaagtgactc ttaggtttta aaacgaaaat tcttgttctt gagtaactct    120

ttcctgtagg tcaggttgct ttctcaggta tagcatgagg tcgctcttat tgaccacacc    180

tctaccggca tgccgagcaa atgcctgcaa atcgctcccc atttcaccca attgtagata    240

tgctaactcc agcaatgagt tgatgaatct cggtgtgtat tttatgtcct cagaggacaa    300

cacctg                                                               306
```

XYLOSE METABOLIZING YEAST

CROSS-REFERENCE TO RELATED APPLICATIONS

This application is a U.S. National Phase Application of International Patent Application No. PCT/EP2019/057753, filed on Mar. 27, 2019, which claims the benefit of priority to U.S. Provisional Patent Application No. 62/648,619, filed Mar. 27, 2018, the entire contents of which are hereby incorporated by reference herein.

The present invention relates to microorganisms, in particular yeast, which have been transformed with one or more expression construct(s) for i) the overexpression of the native genes encoding xylulose kinase (XKS1), transaldolase (TAL1), transketolase 1 (TKL1) and transketolase 2 (TKL2) and ii) the expression of a functional heterologous gene encoding a xylose isomerase (XI), wherein the xylose isomerase (XI) gene is derived from a microorganism selected from the group consisting of *Thermotoga neapolitana, Anditalea andensis* and *Clostridium clariflavum*. The invention also relates to expression constructs for the transgenic expression of xylose isomerase, methods for fermenting pentose sugars using the microorganisms according to the invention and methods for producing such microorganisms.

Xylose is a product of hydrolysis of hemicellulose and constitutes a significant portion of sugar monomers in lignocellulosic hydrolysate liquor. While many organisms, including *Escherichia coli*, can naturally utilize xylose as a carbon source, *Saccharomyces cerevisiae* does not have such capability. However, higher growth inhibitor tolerance and general robustness make yeast a better candidate for utilization of lignocellulosic biomass as a feedstock for the biotech and biofuel industry. Substantial efforts have been made during the last two decades to allow yeast, the world's largest ethanol producer, to metabolize 5 carbon sugars that constitute up to one third of the sugars in lignocellulosic hydrolysate. Among the 5 carbon sugars in lignocellulosic material, xylose is the dominant component.

Two alternative pathways exist in nature that allow incorporation of xylose into metabolic flux—xylose reductase/xylitol dehydrogenase (XR/XDH) and xylose isomerase (XI) (FIG. 1) (Ref. 8). Both processes produce xylulose that is then processed further by xylulose kinase (XKS) and the oxidative phase of the pentose phosphate pathway (PPP). The XI route is predominantly found in prokaryotes and the XR/XDH route in eukaryotes, although exceptions from this rule exist. As a rule of thumb, heterologous gene expression is more efficient in closely related organisms because of the similarities in gene expression and protein maturation machineries as well as in the environment these organisms inhabit—i.e. enzymes from a hyperthermophile may require temperatures that are inaccessible to the new host. This suggests that the use of XR/XDH enzymes might be preferred in *S. cerevisiae*. Reduction of xylose to xylitol is catalyzed by XR and requires NADPH as a cofactor. Oxidation of xylitol to xylulose is catalyzed by XDH, and generates NADH from $NAD^+$. Rapid utilization of xylose as a carbon source would cause equally rapid NADP and NADH imbalance, resulting in growth inhibition. Therefore, efforts through using the XR/XDH pathway have often resulted in strains with low rate of xylose metabolism and the generation of significant amounts of xylitol as a byproduct, which in turn reduce the product yield (Ref. 9).

The other alternative pathway to engineer xylose metabolism through xylose isomerase appears simple as only one enzyme is required and there is no cofactor imbalance problem as mentioned above via XR-XDH pathway. This pathway is common in bacteria but rare in eukaryotic species such as yeast. An anaerobic fungus, *Piromyces* sp. E2 is one of the very few known species that possess a gene that expresses an active XI enzyme. U.S. Pat. No. 7,622,284 B2 describes the method of expressing *Piromyces* sp XI in *S. cerevisiae* that resulted in a yeast strain that can metabolize xylose at a low rate.

According to U.S. Pat. No. 8,114,974 B2, chimeric enzymes comprising contiguous amino acids of a fungal xylose isomerase and of a *Ruminococcus flavefaciens* xylose isomerase are expressed in a host cell such as *Saccharomyces cerevisiae*. U.S. Pat. No. 7,943,366 B2 relates to yeast cells, which are transformed with an exogenous xylose isomerase gene, which may be derived from fungi such as *Piromyces* sp or *Cyllamyces aberensis* or from a bacterium, i.e. *Bacteroides thetaiotaomicron*. In US 2011/0244525 A1, a *Saccharomyces* cell is transformed with a xylose isomerase derived from a *Lactococcus* species and in US 2011/0269180 A1, a yeast cell or a filamentous fungal cell expresses a prokaryotic xylose isomerase derived from *Clostridium phytofermentans*.

However, expression of most of xylose isomerase genes from bacterial origin does not result in the presence of an active xylose isomerase in *S. cerevisiae*, and the exact mechanism for this is not completely understood (Ref. 10). Only a few of XI enzymes from bacterial origins expressed in yeast led to functionally active proteins, but activity is too low to support anaerobic growth on xylose. Therefore, there is still a strong need to identify functional XI enzymes that can be expressed in yeast that have sufficient activities to allow for the use of xylose as carbon source for biobased chemical production.

Moreover, the *Saccharomyces cerevisiae* pentose phosphate pathway (PPP) is the primary metabolic pathway for pentose sugars, which includes xylulose. It acts in parallel to the initial steps of the glycolysis pathway, producing glyceraldehyde-3-phosphate and fructose-6-phosphate from pentose sugars (FIG. 2). In the presence of hexose sugars which can be preferentially metabolized, the PPP is principally required to produce ribose sugars. To produce a yeast strain which is capable of efficiently metabolizing xylose at a high rate, expression of a functional XI gene may not be sufficient as the flux into and trough the pentose phosphate pathway might become the limiting factor. In particular, the xylulose kinase (XKS1), which converts D-xylulose to D-xylulose-5-phosphate and thereby provides the entry into the pentose phosphate pathway and the transketolases TLK1 and TLK2 as well as the transaldolase (TAL1) of the pentose phosphate pathway are of major importance in this context.

It was an objective of the present invention to provide a method for efficient large-scale metabolization of pentose sugars such as xylose. In particular, it was objective of the present invention to provide an inhibitor tolerant and generally robust microorganism such as yeast, preferably of the species *Saccharomyces cerevisiae*, which is capable of metabolizing pentose sugars, in particular xylose, and produce metabolites such as ethanol in a high yield. Such a microorganism should express an exogenous xylose isomerase, which shows high activity in vivo and provides a substantial yield of the desired product. Further objectives can be derived from the below specification, the provided examples and, in particular, the attached claims.

The above identified objectives are met by a microorganism, in particular a yeast, preferably of the species *Saccha-*

*romyces cerevisiae*, which has been transformed with one or more expression construct(s) for i) the overexpression of native genes encoding xylulose kinase (XKS1), transaldolase (TAL1), transketolase 1 (TKL1) and transketolase 2 (TKL2) and ii) the expression of a functional heterologous gene encoding a xylose isomerase (XI), wherein the xylose isomerase (XI) gene is derived from a microorganism selected from the group consisting of *Thermotoga neapolitana, Anditalea andensis* and *Clostridium clariflavum.*

A number of xylose isomerase (XI) genes from different bacterial origins have been tested in *Saccharomyces cerevisiae* overexpressing the native xylulose kinase as well and the mentioned enzymes of the PPP. Only three of the XI genes, namely from *Thermotoga neapolitana* (*T. neapolitana*), *Anditalea andensis* (*A. andensis*) and *Clostridium clariflavum* (*C. clariflavum*) were found to show significant activity in *Saccharomyces cerevisiae*, the XI from *A. andensis* being the most active. As already mentioned above, the reasons why most XI genes from bacterial origin do not result in the expression of active enzymes are not understood. Consequently, there appears to be no reasonable approach to predict which XI's will show significant activity (if any activity at all) when they are expressed in *Saccharomyces cerevisiae.*

A microorganism as described above is preferably a yeast cell, in particular of the species *Saccharomyces cerevisiae*, which contains native xylose kinase (XKS1), transaldolase (TAL1), transketolase 1 (TKL1) and transketolase 2 (TKL2) and is therefore able to introduce and metabolize pentose sugars via the pentose phosphate pathway. Xylulose kinase (XKS1) is an enzyme capable of phosphorylating D-xylulose to D-xylulose-5-phosphate using ATP (EC 2.7.1.17). Transaldolase 1 (TAL1) catalyzes the reaction of sedoheptulose-7-phosphate and D-glyceraldehyde-3-phosphate to D-fructose-6-phosphate and D-erythrose-4-phosphate (EC 2.2.1.2). Transketolases 1 and 2 (TKL1 and TKL2) catalyze the transfer of a 2-carbon fragment from D-xylulose-5-phosphate to D-ribose-5-phosphate to form sedoheptulose-7-phosphate and glyceraldehyde-3-phosphate as well as the transfer of a 2-carbon fragment from D-xylulose-5-phosphate to erythrose-4-phosphate yielding fructose-6-phosphate and glyceraldehyde-3-phosphate (EC 2.2.1.1). Xylose isomerase (XI) catalyzes the interconversion of D-xylose and D-xylulose and is found in many bacteria (EC 5.3.1.5).

Expression constructs in the context of the present invention are nucleic acid sequences comprising one or more promoters, respectively followed by one or more genes to be expressed. Promoters are nucleic acid sequences that control the transcription of one or more genes and are located near the transcription start site of the respective gene(s). Each gene to be expressed is usually also followed by a terminator sequence. Promoters capable of overexpression are preferably constitutive promoters, which are active at all times. In the context of the present invention, preferably native genes of *Saccharomyces cerevisiae* are overexpressed by placing them under the control of suitable promoters, which leads to increased expression of the genes with respect to the unmodified organism expressing the respective endogenous genes.

In contrast, a copy of the XI gene does not naturally exist in the unmodified host organism, *Saccharomyces cerevisiae*, but is introduced and expressed as a transgene derived from a donor organism. To achieve the expression of a transgene in a host cell, the sequence of the transgene is preferably codon optimized for the host cell and placed under the control of a promoter sequence derived from the host cell. A functional heterologous gene leads to the expression of an enzyme, capable of performing its designated role in the host organism.

The donor organisms, from which the XI genes are derived, are bacteria. *Thermotoga neapolitana* is a thermophilic bacterium, which can be found in hot spring environments. *Anditalea andensis* is an alkaliphilic, halotolerant bacterium, which was isolated from very alkaline soil. *Clostridium clariflavum* is a thermophilic bacterium capable of metabolizing cellulose. Particularly preferred in the context of the present invention is the XI gene from *Anditalea andensis* because the in vivo activity of the expressed XI is the highest of the genes tested for expression in *Saccharomyces cerevisiae.*

According to a preferred embodiment the xylose isomerase (XI) is encoded by a nucleic acid sequence having at least 66%, preferably at least 80%, more preferably at least 90% and most preferably at least 95% sequence identity to SEQ ID No 21, SEQ ID No 5 or SEQ ID No 25.

Whenever the present disclosure relates to the percentage of identity of nucleic acid or amino acid sequences to each other, these values define those values as obtained by using the EMBOSS Water Pairwise Sequence Alignments (nucleotide) program (www.ebi.ac.uk/Tools/psa/emboss_water/nucleotide.html) nucleic acids or the EMBOSS Water Pairwise Sequence Alignments (protein) program (www.ebi.ac.uk/Tools/psa/emboss_water/) for amino acid sequences. Alignments or sequence comparisons as used herein refer to an alignment over the whole length of two sequences compared to each other. Those tools provided by the European Molecular Biology Laboratory (EMBL) European Bioinformatics Institute (EBI) for local sequence alignments use a modified Smith-Waterman algorithm (see www.ebi.ac.uk/Tools/psa/ and Smith, T. F. & Waterman, M. S. "Identification of common molecular subsequences" *Journal of Molecular Biology,* 1981 147 (1):195-197). When conducting an alignment, the default parameters defined by the EMBL-EBI are used. Those parameters are (i) for amino acid sequences: Matrix=BLOSUM62, gap open penalty=10 and gap extend penalty=0.5 or (ii) for nucleic acid sequences: Matrix=DNAfull, gap open penalty=10 and gap extend penalty=0.5.

SEQ ID No 21 corresponds to the nucleic acid sequence of the native XI gene of *T. neapolitana*, SEQ ID No 5 to the native XI gene of *A. andensis* and SEQ ID No 25 to the native XI gene of *C. clariflavum*. Sequences having a sequence identity of at least 66%, 70%, 75%, 80%, 85%, 90%, 95%, 96%, 97%, 98% or 99%, respectively, may be used in the context of the present invention as long as they allow expression of a functional xylose isomerase. Since the genes are expressed in a host organism different from the respective donor, the sequences are preferably codon optimized for the expression in *Saccharomyces cerevisiae*. Hence, differences due to the codon-optimization for *Saccharomyces cerevisiae* covered by the above given sequences identities are known to the skilled person and can easily be identified.

Preferably the xylose isomerase (XI) is represented by an amino acid sequence having at least 80%, preferably at least 90%, more preferably at least 95% and most preferably at least 99% sequence identity to SEQ ID No 22, SEQ ID No 6 or SEQ ID No 26.

SEQ ID No 22 corresponds to the amino acid sequence of the native XI from *T. neapolitana*, SEQ ID No 6 to the native XI of *A. andensis* and SEQ ID No 26 to the native XI of *C. clariflavum*. Sequences having a sequence identity of at least 80%, 85%, 90%, 95%, 96%, 97%, 98% or 99%, respectively, may be used in the context of the present invention as long as they constitute a functional xylose isomerase.

According to a preferred embodiment, the xylulose kinase (XKS1) is encoded by a nucleic acid sequence having at least 80%, preferably at least 90%, more preferably at least 95% and most preferably at least 99% sequence identity to SEQ ID No 74, the transaldolase (TAL1) is encoded by a nucleic acid sequence having at least 80%, preferably at least 90%, more preferably at least 95% and most preferably at least 99% sequence identity to SEQ ID No 77, the transketolase 1 (TKL1) is encoded by a nucleic acid sequence having at least 80%, preferably at least 90%, more preferably at least 95% and most preferably at least 99% sequence identity to SEQ ID No 80 and the transketolase 2 (TKL2) is encoded by a nucleic acid sequence having at least 80%, preferably at least 90%, more preferably at least 95% and most preferably at least 99% sequence identity to SEQ ID No 83.

SEQ IDs No 74, 77, 80 and 83 correspond to the nucleic acid sequence of the native XKS1 gene, the native TAL1 gene and the native TKL1 and TKL2 genes of *Saccharomyces cerevisiae*. Sequences having a sequence identity of at least 80%, 85%, 90%, 95%, 96%, 97%, 98% or 99%, respectively, may be used in the context of the present invention as long as they allow expression of an enzyme capable of performing the respective function.

In a further preferred embodiment, each of the genes encoding xylulose kinase (XKS1), transaldolase (TAL1), transketolase 1 (TKL1), transketolase 2 (TKL2) and xylose isomerase (XI) is under the control of a constitutive promoter, wherein the constitutive promoter is selected from TDH3 encoded by a nucleic acid sequence having at least 80%, preferably at least 90%, more preferably at least 95% and most preferably at least 99% sequence identity to SEQ ID No 73, PGK1 encoded by a nucleic acid sequence having at least 80%, preferably at least 90%, more preferably at least 95% and most preferably at least 99% sequence identity to SEQ ID No 76, CYC19 encoded by a nucleic acid sequence having at least 80%, preferably at least 90%, more preferably at least 95% and most preferably at least 99% sequence identity to SEQ ID No 79, PFK1 encoded by a nucleic acid sequence having at least 80%, preferably at least 90%, more preferably at least 95% and most preferably at least 99% sequence identity to SEQ ID No 82, truncated HXT7 encoded by a nucleic acid sequence having at least 80%, preferably at least 90%, more preferably at least 95% and most preferably at least 99% sequence identity to SEQ ID No 90 and TEF encoded by a nucleic acid sequence having at least 80%, preferably at least 90%, more preferably at least 95% and most preferably at least 99% sequence identity to SEQ ID No 85.

The genes of the expression construct according to the present invention are preferably placed under the control of constitutive promoters of *Saccharomyces cerevisiae*. Sequences having a sequence identity of at least 80%, 85%, 90%, 95%, 96%, 97%, 98% or 99%, respectively, may be used in the context of the present invention as long as they are able to promote expression or, respectively, overexpression of the genes as described hererin.

Preferably, the XKS1 gene is placed under the control of the TDH3 promoter and/or the TAL1 gene is placed under the control of the PGK1 promoter and/or the TKL1 gene is placed under the control of the CYC19 promoter and the TKL2 gene is placed under the control of the PFK1 promoter. Further preferably, the XI gene is placed under the control of the truncated HXT7 or the TEF promoter. These combinations of genes and promoters resulted in higher expression levels than other combinations.

In the respective expression construct(s), the sequences of the genes described above are preferably followed by terminator sequences derived from *Saccharomyces cerevisiae*. Such terminator sequences may be selected from tDIT1 (SEQ ID No 75), tYHI9 (SEQ ID No 78), tEFM (SEQ ID No 81), tRPL15A (SEQ ID No 84), tTEF (SEQ ID No 87), tCYC1 (SEQ ID No 91) and tADH1 (SEQ IS No 94).

Preferably, the XKS1 is followed by the DIT1 terminator and/or the TAL1 gene is followed by the YHI9 terminator and/or the TKL1 gene is followed by the EFM1 terminator and the TKL2 gene is followed by the RPL15A terminator. Further preferably, the XI gene is followed by the CYC1 terminator or the ADH1 terminator. The combinations of genes and promoters as specified above with the terminators as specified above resulted in particularly high expression levels.

The present invention also relates to an expression construct for the expression of a gene encoding a xylose isomerase (XI) derived from a microorganism selected from the group consisting of *T. neapolitana*, *A. andensis* and *C. clariflavum*, wherein the xylose isomerase (XI) gene is under the control of a constitutive promoter of *Saccharomyces cerevisiae*. Particularly preferred is a gene encoding XI derived from *A. andensis*.

Preferably, the gene encoding the xylose isomerase (XI) is represented by a nucleic acid sequence having at least 66%, preferably at least 80%, more preferably at least 90% and most preferably at least 95% sequence identity to SEQ ID No 21, SEQ ID No 5 or SEQ ID No 25.

SEQ ID No 21 corresponds to the nucleic acid sequence of the native XI gene of *T. neapolitana*, SEQ ID No 5 to the native XI gene of *A. andensis* and SEQ ID No 25 to the native XI gene of *C. clariflavum*. Sequences having a sequence identity of at least 80%, 85%, 90%, 95%, 96%, 97%, 98% or 99%, respectively, may be used in the context of the present invention as long as they allow expression of a functional xylose isomerase. Since the genes are intended to be expressed in *Saccharomyces cerevisiae*, the sequences are preferably codon optimized for *Saccharomyces cerevisiae*. Differences due to codon-optimization covered by the sequence identities given above are known to the skilled person.

Further preferably, the constitutive promoter is selected from truncated HXT7 encoded by a nucleic acid sequence having at least 80%, preferably at least 90%, more preferably at least 95% and most preferably at least 99% sequence identity to SEQ ID No 90 and TEF encoded by a nucleic acid sequence having at least 80%, preferably at least 90%, more preferably at least 95% and most preferably at least 99% sequence identity to SEQ ID No 85.

The XI gene of the expression construct described above is preferably placed under the control of constitutive promoters of *Saccharomyces cerevisiae*. Sequences having a sequence identity of at least 80%, 85%, 90%, 95%, 96%, 97%, 98% or 99%, respectively, may be used in the context of the present invention as long as they are able to promote expression of a functional XI.

The present invention further relates to a method for fermenting pentose sugar(s) comprising culturing a microorganism as described above in a culture medium comprising pentose sugar(s) under conditions, in which the pentose sugar(s) can be metabolized.

Preferably, the method is a method for fermenting xylose. As already mentioned above, xylose is a product of hydrolysis of hemicellulose and represents a significant portion of sugar monomers in lignocellulosic hydrolysate liquor. It is therefore particularly desirable to be able to ferment xylose to use lignocellulosic biomass as a feedstock for the biotech and biofuel industry.

According to a particularly preferred embodiment, the culture medium therefore comprises or consists of lignocellulosic biomass and/or a hydrolysate thereof.

Useful products of pentose sugar fermentation, in particular xylose fermentation, are ethanol, methanol, propanol, isopropanol, butanol, ethylene glycol, propylene glycol, 1,4-butanediol, glycerin, formic acid, acetic acid, propionic acid, butyric acid, valeric acid, caproic acid, palmitic acid, stearic acid, oxalic acid, malonic acid, succinic acid or succinate, glutaric acid, oleic acid, linoleic acid, glycolic acid, lactic acid or lactate, gamma-hydroxybutyric acid, 3-hydroxyalkanoic acid, alanine, methane, ethane, propane, pentane, n-hexane, pyruvate, aspartate, malate, valine, leucine and combinations thereof. Particularly preferred is the production of ethanol, which besides being used as a biofuel has many other uses.

In a method as described above the fermentation therefore produces one or more compounds selected from ethanol, methanol, propanol, isopropanol, butanol, ethylene glycol, propylene glycol, 1,4-butanediol, glycerin, formic acid, acetic acid, propionic acid, butyric acid, valeric acid, caproic acid, palmitic acid, stearic acid, oxalic acid, malonic acid, succinic acid or succinate, glutaric acid, oleic acid, linoleic acid, glycolic acid, lactic acid or lactate, gamma-hydroxybutyric acid, 3-hydroxyalkanoic acid, alanine, methane, ethane, propane, pentane, n-hexane, pyruvate, aspartate, malate, valine and leucine, preferably ethanol.

The present invention also relates to the use of a microorganism as described above for the fermentation of pentose sugar(s), in particular xylose, preferably for the production of ethanol from lignocellulosic biomass.

A microorganism according to the present invention is capable of efficiently fermenting pentose sugar(s) such as xylose on a large scale and therefore allows industrial production of desired metabolites. Advantageously, it can be used to produce ethanol from lignocellulosic biomass.

Furthermore, the present invention also relates to a method of producing a microorganism as described above comprising the transformation of a *Saccharomyces cerevisiae* strain with any expression construct(s) as described above. In particular, the *Saccharomyces cerevisiae* strain is transformed with expression construct(s) for i) the overexpression of native genes encoding xylulose kinase (XKS1), transaldolase (TAL1), transketolase 1 (TKL1) and transketolase 2 (TKL2) and
ii) the expression of a functional heterologous gene encoding a xylose isomerase (XI), wherein the xylose isomerase (XI) gene is derived from a microorganism selected from the group consisting of *T. neapolitana, A. andensis* and *C. clariflavum.*

Particularly preferred is the XI gene derived from *A. andensis.*

With respect to the respective genes and sequences, the previous remarks apply accordingly.

The expression construct may be delivered to the cell on a plasmid and may be expressed from the plasmid or integrated into the genome of the *Saccharomyces cerevisiae* strain. A person skilled in the art is well aware of suitable transformation methods and the related advantages.

According to a preferred embodiment, the expression construct is integrated into a chromosome of the *Saccharomyces cerevisiae* strain, preferably chromosome 16. A preferred assembly of the PPP pathway targeting an integration site at chromosome 16 is shown in FIG. 4. It has been demonstrated by Flagfeldt, D. B., Siewers, V., Huang, L. and Nielsen, J. in "Characterization of chromosomal integration sites for heterologous gene expression in *Saccharomyces cerevisiae*". Yeast, 26 (10), 545-551, 2009, that this integration site resulted in the highest expression for heterologous genes. In the assembly shown in FIG. 4, the kanamycin resistance marker may then be replaced by the XI integration module.

In a further preferred embodiment, the expression construct for the xylose isomerase (XI) as described above is integrated into a recombinant expression construct for the overexpression of the native genes for xylulose kinase (XKS1), transaldolase (TAL1), transketolase 1 (TKL1) and transketolase 2 (TKL2).

Advantageously, this embodiment results in an expression construct containing all the necessary genes, which allows transformation in one step. A particularly preferred embodiment of such an expression construct is described in the following examples. However, variations according to the above disclosure are possible as can be appreciated by the skilled person.

SHORT DESCRIPTION OF THE FIGURES

FIG. 1 shows the two routes for consumption of xylose as a carbon source. Xylose is converted to xylulose by either xylose reductase and xylitol dehydrogenase (A) or xylose isomerase (B). Both pathways consume ATP but xylose reductase and xylitol dehydrogenase also utilize NADPH and produce NADH causing cofactor imbalance (Ref 8).

Figure 5:
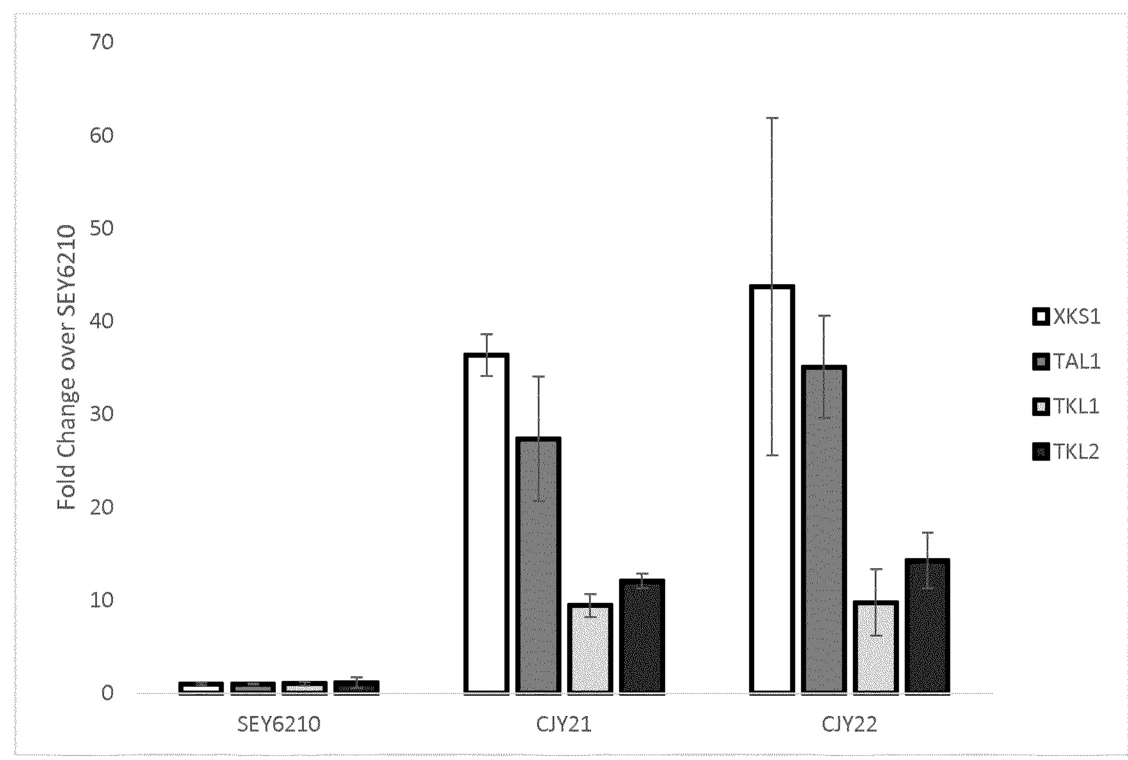

FIG. 5 shows XKS and pentose phosphate pathway (PPP) expression by RT-qPCR. SEY6210 is the parental *Saccharomyces* laboratory strain; CJY21 and CJY22 are two isogenic clones isolated by transforming SEY6210 with the XKS-PPP overexpression module.

Figure 6:
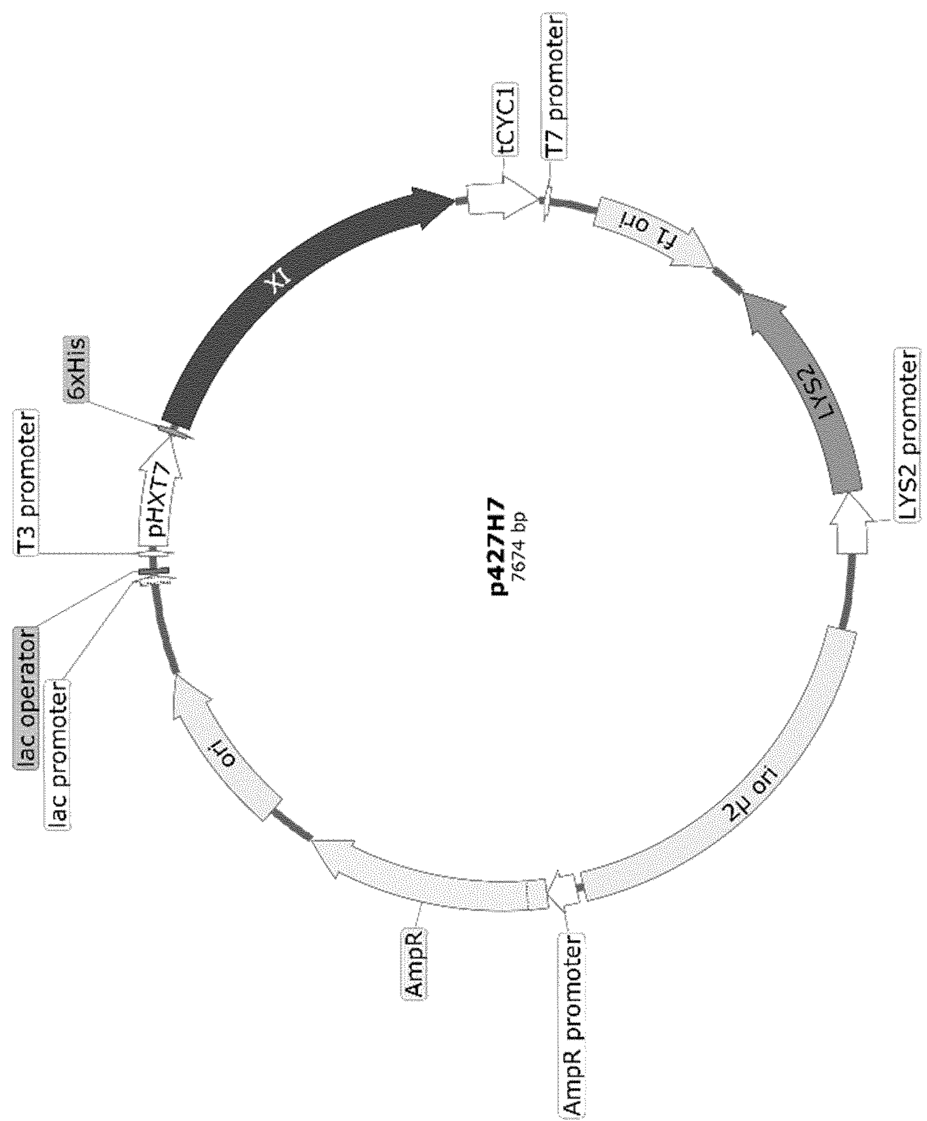

FIG. 6 shows the gene expression cassette generated for overexpression of xylose isomerase under the truncated HXT7 promoter.

Figure 7:
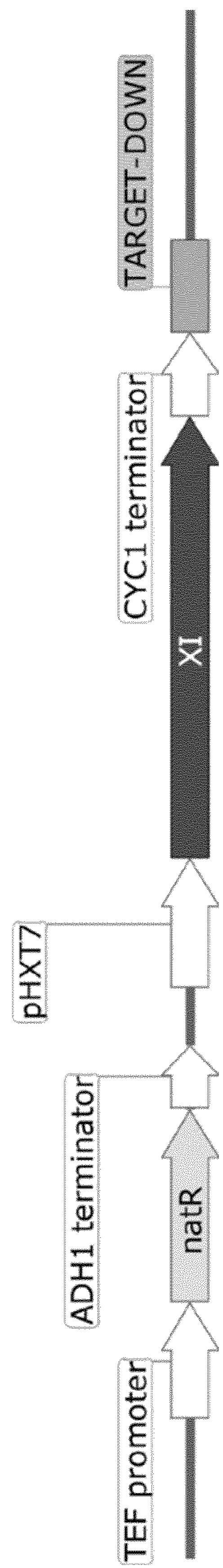

FIG. 7 shows the integration cassette generated for replacing the KanR resistance marker with a single copy of the candidate xylose isomerase module.

Figure 8:
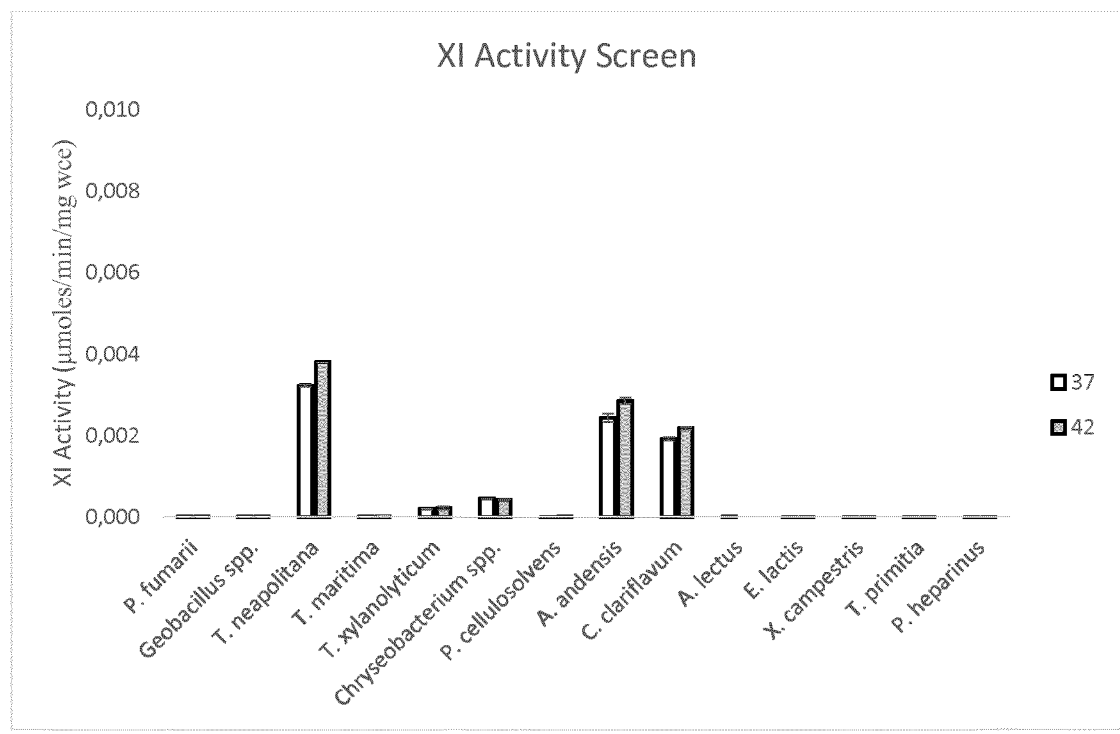

FIG. 8 shows the result of the xylose isomerase activity assay using whole cell extracts performed at 37° C. and 42° C.

Figure 9:
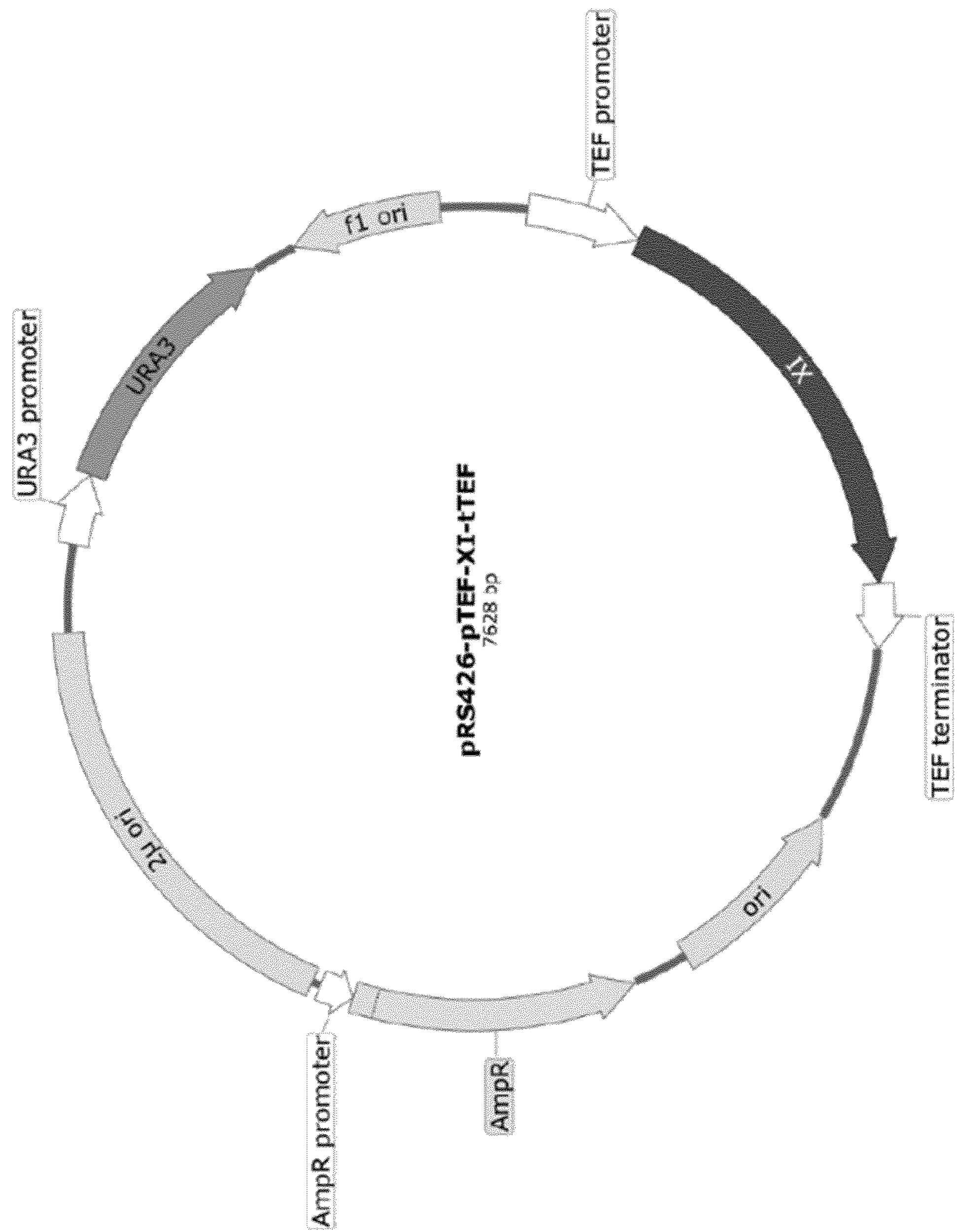

FIG. 9 shows the pRS426 expression vector used in example 2.

Figure 10:
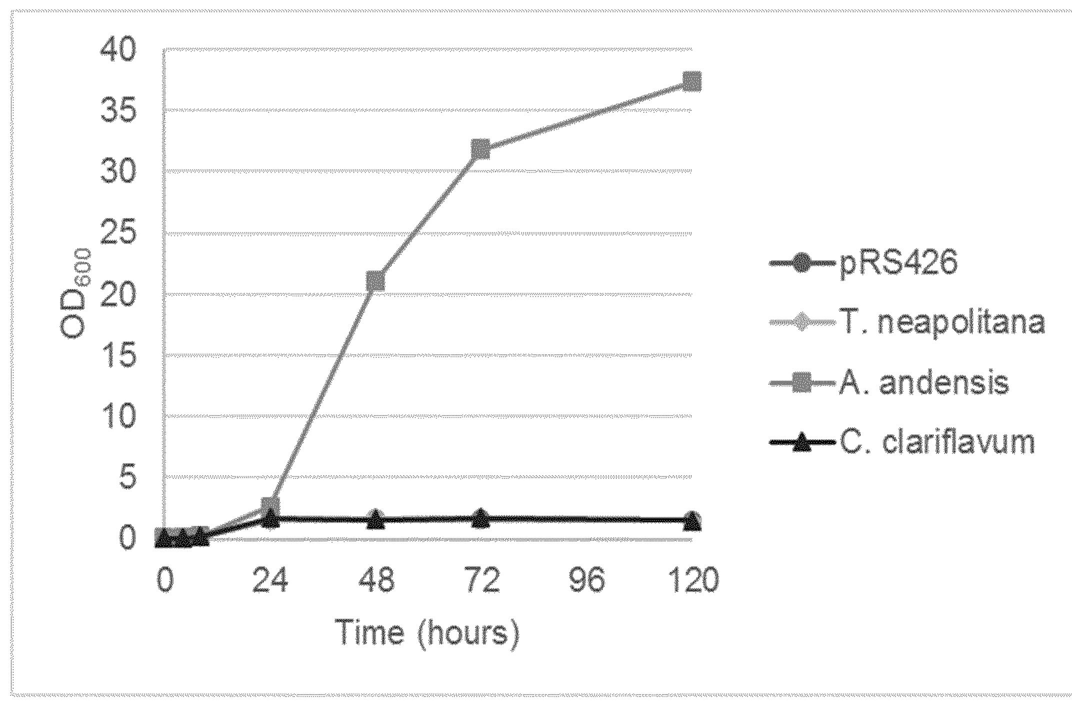

FIG. 10 shows the aerobic growth of the (transformed) strains on xylose using YEP medium with 20 g/L xylose at 30° C. and shaking at 200 rpm.

Figure 11:
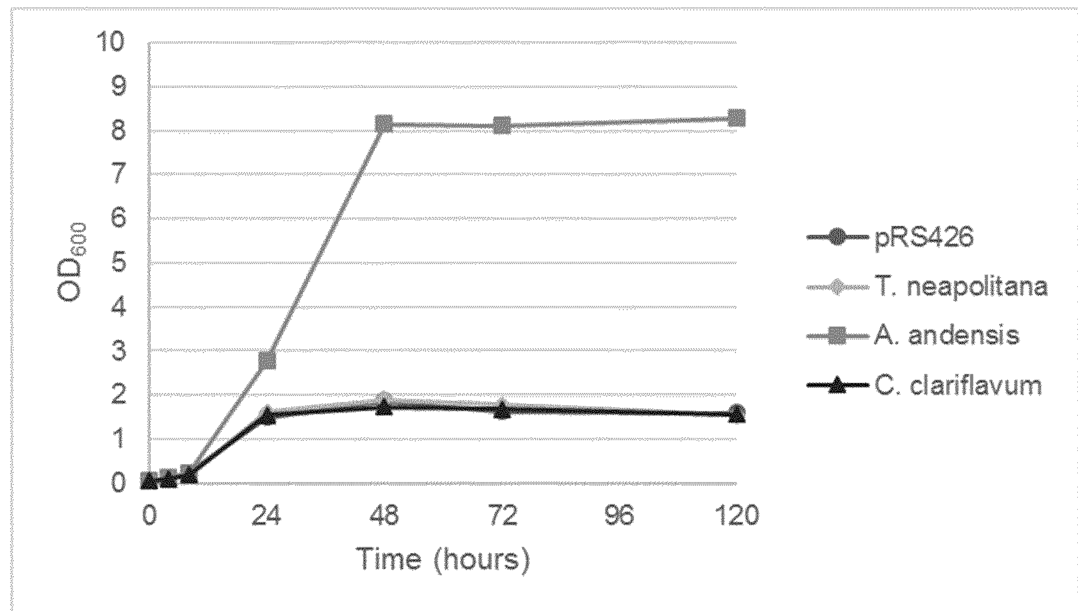

FIG. 11 shows the anaerobic growth of the (transformed) strains on xylose using YEP medium with 20 g/L xylose at 30° C. and shaking at 200 rpm.

Figure 12:
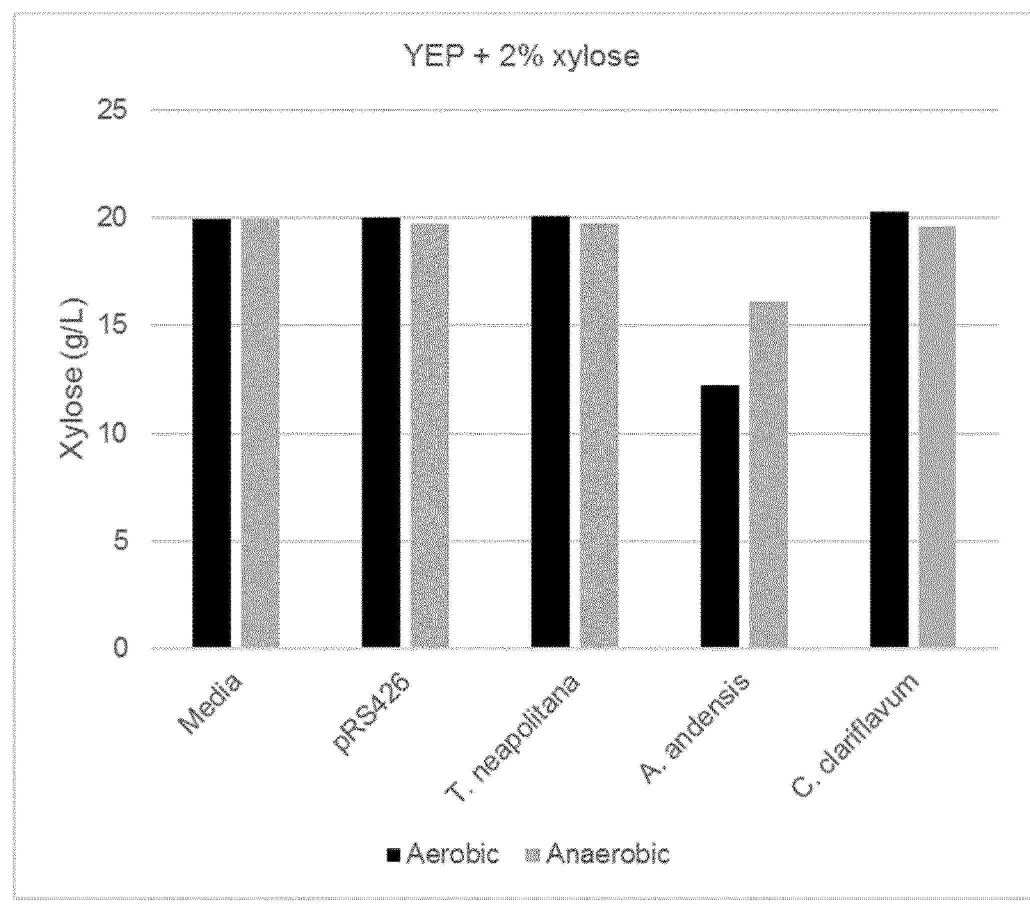

FIG. 12 shows the xylose consumption in aerobic (left column) and anaerobic (right column) fermentation using YEP medium with 20 g/L xylose at 30° C. and shaking at 200 rpm.

Figure 13:
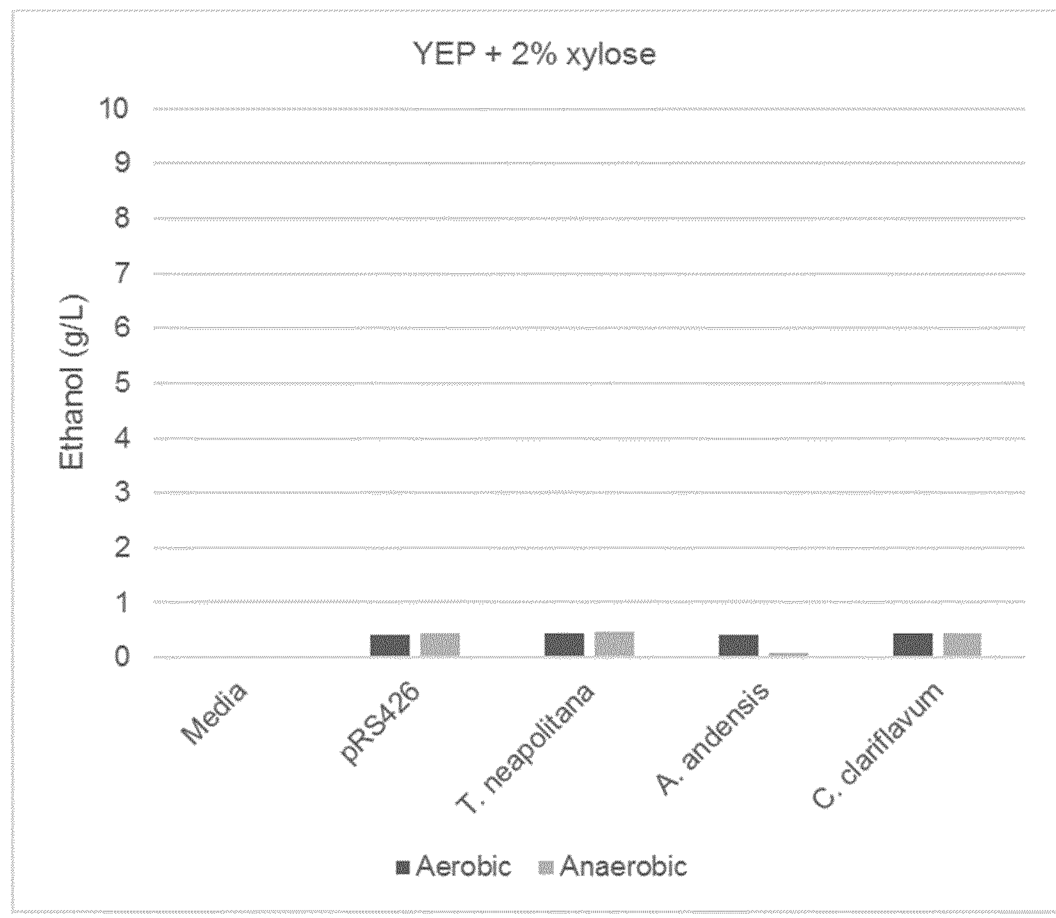

FIG. 13 shows the ethanol production in aerobic (left column) and anaerobic (right column) fermentation using YEP medium with 20 g/L xylose at 30° C. and shaking at 200 rpm.

EXAMPLE 1: CONSTRUCTION OF A XKS-PPP EXPRESSION MODULE

Figure 1:
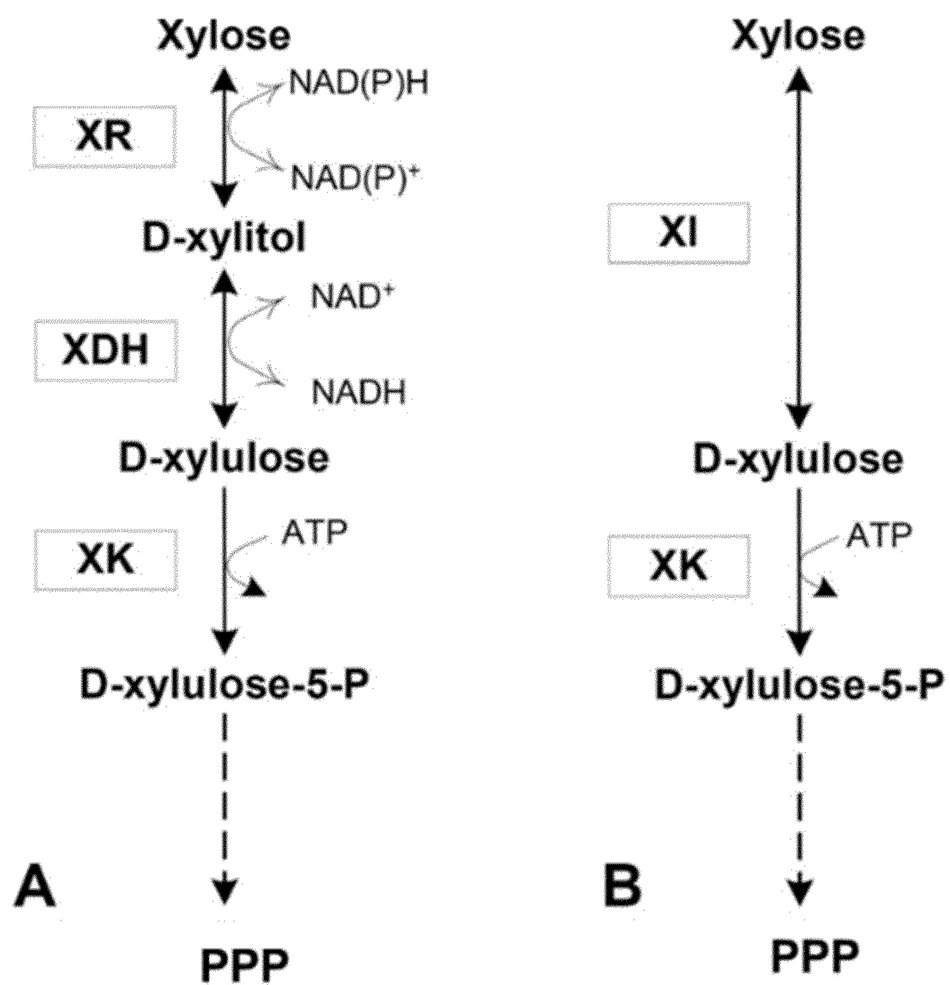
Figure 2:
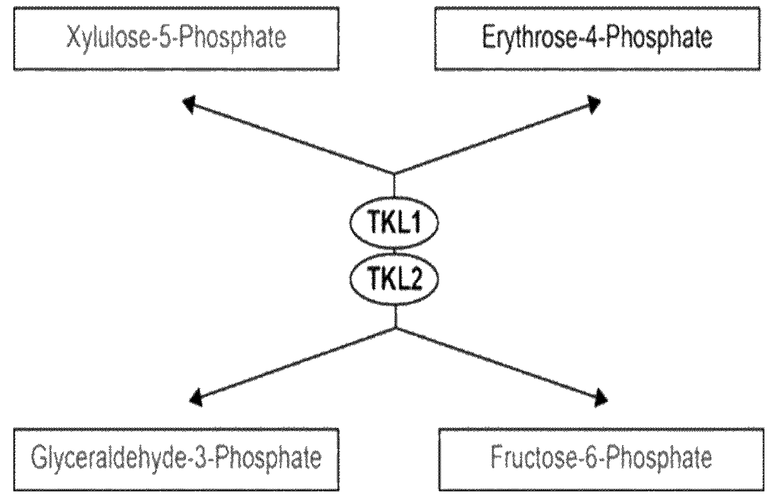
FIG. 2 shows a schematic overview of the pentose phosphate pathway in *Saccharomyces cerevisiae.*
Figure 2:
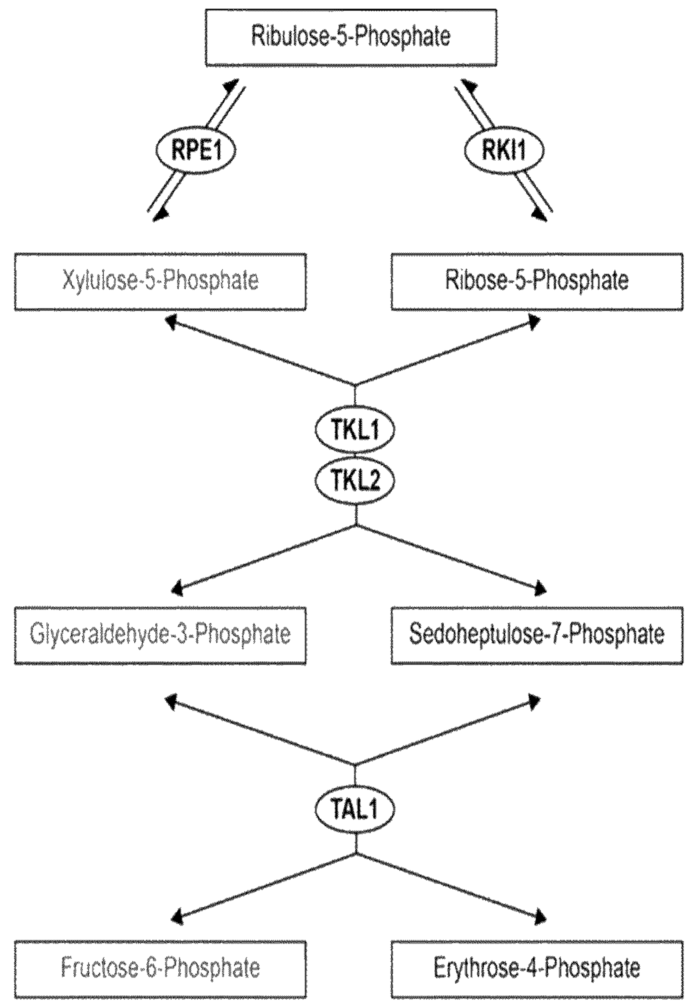
Figure 3:
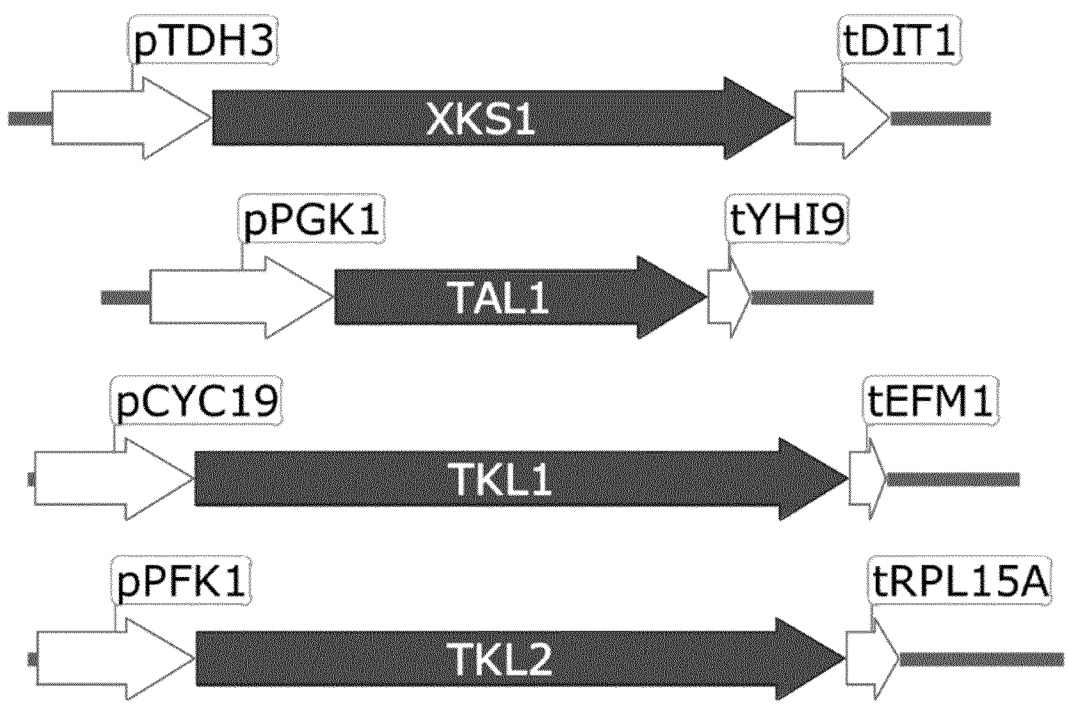
FIG. 3 shows the expression cassette fragments generated for the overexpression of XKS1, TAL1, TKL1 and TKL2.

A *Saccharomyces* test strain was engineered to overexpress the yeast pentose phosphate pathway. Gene expression cassette fragments were generated for overexpression of XKS1 under the TDH3 promoter, TAL1 under the PGK1 promoter, TKL1 under the CYC19 promoter and TKL2 under the PFK1 promoter (FIG. 3).

Construction of XKS expression module: the TDH3 promoter was PCR amplified from SEY6210 genomic DNA using the primers identified by SEQ. ID. No. 29 and SEQ. ID. No. 30. The coding region of XKS1 gene was PCR amplified from SEY6210 genomic DNA using the primers identified by SEQ. ID. No. 31 and SEQ. ID. No. 32. The DIT1 terminator was PCR amplified from SEY6210 genomic DNA using the primers identified by SEQ. ID. No. 33 and SEQ. ID. No. 34. PCR products were then column purified and assembled into SmaI-linearized pRS426 (Ref. 2) vector by Gibson isothermal assembly (Ref. 1).

Construction of TAL1 expression module: the PGK1 promoter was PCR amplified from SEY6210 genomic DNA using the primers identified by SEQ. ID. No. 35 and SEQ. ID. No. 36. The coding region of TAL1 gene was PCR amplified from SEY6210 genomic DNA using the primers identified by SEQ. ID. No. 37 and SEQ. ID. No. 38. The YHI9 terminator was PCR amplified from SEY6210 genomic DNA using the primers identified by SEQ. ID. No. 39 and SEQ. ID. No. 40. PCR products were then column purified and assembled into SmaI-linearized pRS426 (Ref. 2) vector by Gibson isothermal assembly (Ref. 1).

Construction of TKL1 expression module: the CYC19 promoter was PCR amplified from SEY6210 genomic DNA using the primers identified by SEQ. ID. No. 41 and SEQ. ID. No. 42. The coding region of TKL1 gene was PCR amplified from SEY6210 genomic DNA using the primers identified by SEQ. ID. No. 43 and SEQ. ID. No. 44. The EFM1 terminator was PCR amplified from SEY6210 genomic DNA using the primers identified by SEQ. ID. No. 45 and SEQ. ID. No. 46. PCR products were then column purified and assembled into SmaI-linearized pRS426 (Ref. 2) vector by Gibson isothermal assembly (Ref. 1).

Construction of TKL2 expression module: the PFK1 promoter was PCR amplified from SEY6210 genomic DNA using the primers identified by SEQ. ID. No. 47 and SEQ. ID. No. 48. The coding region of TKL2 gene was PCR amplified from SEY6210 genomic DNA using the primers identified by SEQ. ID. No. 49 and SEQ. ID. No. 50. The RPL15A terminator was PCR amplified from SEY6210 genomic DNA using the primers identified by SEQ. ID. No. 51 and SEQ. ID. No. 52. PCR products were then column purified and assembled into SmaI-linearized pRS426 (Ref. 2) vector by Gibson isothermal assembly (Ref. 1).

Construction of TKL1-XKS1 expression module: the TKL1 cassette was PCR amplified from pRS426 vector containing TKL1 expression module using the primers identified by SEQ. ID. No. 53 and SEQ. ID. No. 54. The XKS1 cassette was PCR amplified from pRS426 vector containing XKS1 expression module using the primers identified by SEQ. ID. No. 55 and SEQ. ID. No. 56. PCR products were then column purified and assembled into SmaI-linearized pRS426 (Ref. 2) vector by Gibson isothermal assembly (Ref. 1).

Construction of TKL2-TAL1 expression module: the TKL2 cassette was PCR amplified from pRS426 vector containing TKL2 expression module using the primers identified by SEQ. ID. No. 59 and SEQ. ID. No. 60. The TAL1 cassette was PCR amplified from pRS426 vector containing TAL1 expression module using the primers identified by SEQ. ID. No. 57 and SEQ. ID. No. 58. PCR products were then column purified and assembled into SmaI-linearized pRS426 (Ref. 2) vector by Gibson isothermal assembly (Ref. 1).

Construction of XKS-PPP expression module: The TKL1-XKS1 cassette was PCR amplified from pRS426 vector containing TKL1-XKS1 expression module using the primers identified by SEQ. ID. No. 61 and SEQ. ID. No. 62. The $Kan^R$ selection marker (SEQ ID No: 86) was PCR amplified from pRS42K (Ref. 1) using the primers identified by SEQ. ID No. 63 and SEQ. ID. No. 64. The TAL1-TKL2 cassette was PCR amplified from pRS426 vector containing TAL1-TKL2 expression module using the primers identified by SEQ. ID No. 65 and SEQ. ID. No. 66. PCR products were then column purified and assembled into SmaI-linearized pRS426 (Ref. 2) vector by Gibson isothermal assembly (Ref. 1).

Figure 4:
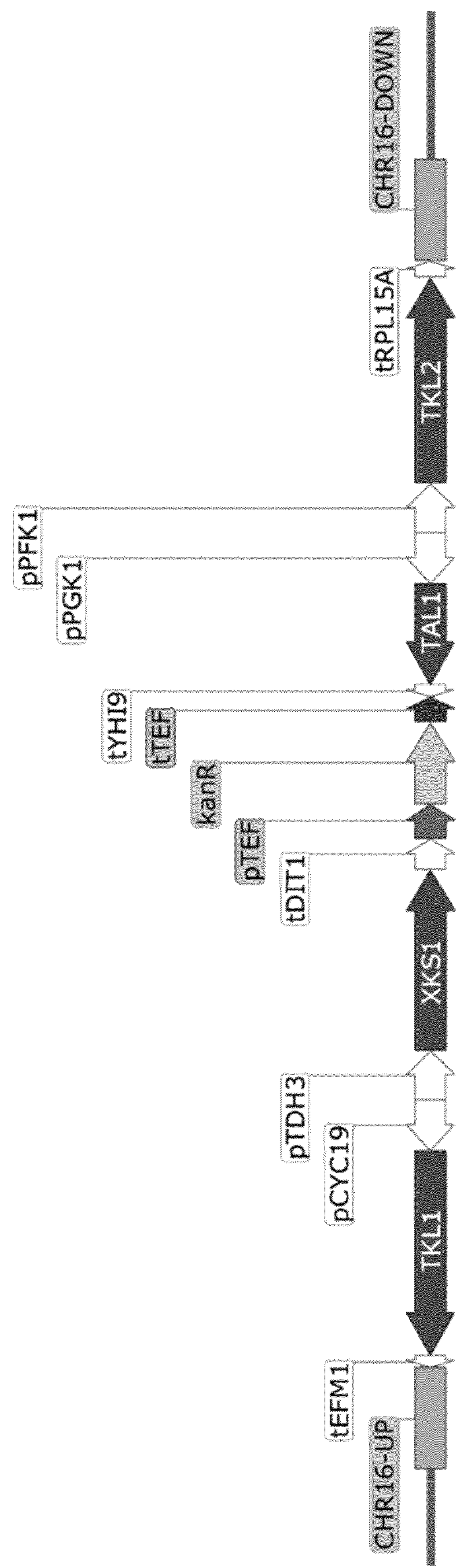
FIG. 4 shows the pentose phosphate pathway (PPP) assembly with Kan$^R$ selection marker targeting an integration site at chromosome 16 of the *Saccharomyces* laboratory strain SEY6210.

Construction of XKS-PPP chromosome 16 integration module: A 5' homology arm, CHR16-UP (SEQ ID No: 88), targeting chromosome 16 of the *Saccharomyces* laboratory strain SEY6210 was amplified from SEY6210 genomic DNA using the primers identified by SEQ. ID No. 69 and SEQ. ID. No. 70. The PPP-KanR module was amplified from pRS426 vector containing PPP-KanR using the primers identified by SEQ. ID No. 67 and SEQ. ID. No. 68. A 3' homology arm, CHR16-DOWN (SEQ ID No: 89), targeting chromosome 16 of the *Saccharomyces* laboratory strain SEY6210 was amplified from SEY6210 genomic DNA using the primers identified by SEQ. ID No. 71 and SEQ. ID. No. 72. PCR products were then column purified and assembled into SmaI-linearized pRS426 (Ref. 2) vector by Gibson isothermal assembly (Ref. 1). The integration cassette containing homology arms, the PPP, and the KanR marker was liberated from the plasmid backbone with BamHI and SalI to create a linear recombination cassette (FIG. 4), and then transformed into SEY6210. Screening transformants resulted in isogenic clones CJY21 and CJY22. Overexpression of the XKS and PPP genes was verified by RT-qPCR (FIG. 5).

EXAMPLE 2: XI CANDIDATE SCREENING

A total of 14 xylose isomerase enzyme candidates were translated from nucleotide SEQ. ID. No. 1, 3, 5, 7, 9, 11, 13, 15, 17, 19, 21, 23, 25 and 27 into protein sequences SEQ. ID. No. 2, 4, 6, 8, 10, 12, 14, 16, 18, 20, 22, 24, 26 and 28, codon-optimized for *Saccharomyces*, and synthesized (IDT). These synthesized candidate genes were then cloned into pRS427[2] under control of the truncated, constitutive $HXT7_{7-391}$ (Ref. 3) promoter (SEQ. ID. No. 90) and CYC1 terminator from *S. cerevisiae* (SEQ. ID. No. 91) (FIG. 6).

The HXT7 promoter-XI gene-CYC1 terminator cassette was further subcloned into an integration vector with the TEF promoter (SEQ ID. No. 87), which is homologous to the TEF promoter on the 5' end of the $KAN^R$ marker in the PPP cassette, the $NAT^R$ resistance marker (Ref. 4) (SEQ. ID. No. 93), the ADH1 terminator (SEQ. ID. No. 94) and a TARGET-DOWN sequence (SEQ. ID. No 92) homologous to the 3' end of the $KAN^R$ marker in the PPP cassette (FIG. 7). This integration module was then transformed into CJY21, replacing the $KAN^R$ resistance marker with a single copy of the candidate xylose isomerase module.

Xylose isomerase candidates were assayed for enzymatic activity in vitro. Strains were grown in 5 ml of YPD overnight, harvested, washed, and lysed by mechanical bead beating (MP Biomedical Fastprep) in XI assay lysis buffer (50 mM TRIS pH 7.5, 150 mM NaCl, 0.01% Triton X-100, 10 mM $MgCl_2$, 50 μM $CoCl_2$, 50 μM $MnCl_2$, with Pierce Protease Inhibitors [Pierce 88666]). Protein concentration was determined by Bradford assay (Ref. 5). 50 μl of cleared whole-cell extract (WCE) was incubated with 50 μl of 100 mM D-xylose for 16 hours separately at 37° C. and at 42° C., then stopped by heating to 95° C. for 5 minutes and cleared by centrifugation.

Quantification of xylulose was done by sorbitol dehydrogenase (SDH)-based, NADH-linked assay (Ref. 6). In a 96-well plate (Corning #3635), SDH buffer (Megazymes) and 150 μM NADH were combined with 10 μl of assayed sugar solution at a total volume of 200 μl, mixed, and then scanned for $A_{340}$. 3.5 μl of SDH solution (Megazymes) was added, mixed, and allowed to incubate at room temperature for 15 minutes. The plate was then scanned again for A340. NADH concentration in the assay solution was determined using the extinction coefficient at A340 (6220 $M^{-1}$ $cm^{-1}$) and path length of 0.58 cm, then used to calculate the xylulose concentration. Xylose isomerase reaction velocity [μmoles/min/mg WCE] was then calculated for the enzymatic conversion of D-xylose to xylulose. Three candidates were identified with in vitro xylose isomerase activity when expressed in *Saccharomyces* (FIG. 8).

XI candidates showing strong activity in the initial screen from *T. neapolitana* (SEQ. ID. No. 22), *A. andensis*, (SEQ. ID. No. 6) and *C. clariflavum* (SEQ. ID. No. 26) were then subcloned into pRS426 (FIG. 9) under control of the strong constitutive pTEF promoter (SEQ. ID. No. 85).

These plasmids were then transformed into CJY21 and growth were determined by measuring absorbance at 600 nm in aerobic shake flasks (FIG. 10) and anaerobic pressure bottles (FIG. 11) in YEP+20 g/l D-xylose. Xylose consumption and ethanol formation were also monitored by HPLC at fermentation time of 48 h (for *A. andensis,* 120 h sample was also measured for ethanol production) (FIGS. 12 and 13).

Enzyme kinetics for strains CJY21 containing pRS426 expression vector expressing XI's from *T. neapolitana* (SEQ. ID. No. 22), *A. andensis*, (SEQ. ID. No. 6) and *C. clariflavum* (SEQ. ID. No. 26) were repeated as above using D-xylose concentrations of 50 mM, 25 mM, 5 mM, and 1 mM in 30 minute reactions at 30° C. $V_{max}$ was calculated using the Michaelis-Menten kinetic equation and shown in Table 1 along with reference XI activities for *Piromyces* sp. and *Clostridium phytofermentas* xylose isomerases taken from literature.

TABLE 1

In-vitro xylose isomerase activities

| Xylose Isomerase | $V_{max}$ [μmoles/min/mg] |
| --- | --- |
| *Thermotoga neopolitana* | 0.0223 |
| *Anditalea andensis* | 0.0426 |
| *Clostridium clariflavum* | 0.0051 |
| *Piromyces* sp. | 0.0538[7] |
| *Clostridium phytofermentas* | 0.0344[7] |

REFERENCES

1. Taxis, C. & Knop, M. System of centromeric, episomal, and integrative vectors based on drug resistance markers for *Saccharomyces cerevisiae. BioTechniques* 40, 73-78 (2006).

2. Fang, F. et al. A vector set for systematic metabolic engineering in *Saccharomyces cerevisiae. Yeast* (Chichester, England) 28, 123-136, doi:10.1002/yea.1824 (2011).

3. Lai, M. T., Liu, D. Y. & Hseu, T. H. Cell growth restoration and high level protein expression by the promoter of hexose transporter, HXT7, from *Saccharomyces cerevisiae. Biotechnology letters* 29, 1287-1292, doi:10.1007/s10529-007-9397-3 (2007).

4. Goldstein, A. L. & McCusker, J. H. Three new dominant drug resistance cassettes for gene disruption in *Saccharomyces cerevisiae. Yeast* 15, 1541-1553, doi:10.1002/(sici)1097-0061(199910)15:14<1541::aid-yea476>3.0.co;2-k (1999).

5. Bradford, M. M. A rapid and sensitive method for the quantitation of microgram quantities of protein utilizing the principle of protein-dye binding. *Analytical biochemistry* 72, 248-254 (1976).

6. Kersters-Hilderson, H., Callens, M., Van Opstal, O., Vangrysperre, W. & De Bruyne, C. K. Kinetic characterization of d-xylose isomerases by enzymatic assays using d-sorbitol dehydrogenase. *Enzyme and Microbial Technology* 9, 145-148, doi:10.1016/0141-0229(87)90067-6 (1987).

7. Brat, D., Boles, E. & Wiedemann, B. Functional expression of a bacterial xylose isomerase in *Saccharomyces cerevisiae. Applied and environmental microbiology* 75, 2304-2311, doi:10.1128/aem.02522-08 (2009).

8. Karhumaa, K., Sanchez, R. G., Hahn-Hagerdal, B. and Gorwa-Grauslund, M. Comparison of the xylose reductase-xylitol dehydrogenase and the xylose isomerase pathways for xylose fermentation by recombinant *Saccharomyces cerevisiae.* Microbial Cell Factories, 6, 5-15 (2007).

9. van Maris, A. J. A., Winkler, A. A., Kuyper, M, de Laat, W. T. A. M., van Dijken, J. P., Pronk, J. T. Development of efficient xylose fermentation in *Saccharomyces cerevisiae*: xylose isomerase as a key component. Adv Biochem Engin/Biotechnol 108, 179-204 (2007)

10. Brat, D., Boles, E. and Wiedemann, B. Fuctional expression of a bacterial xylose isomerase in *Saccharomyces cerevisiae*. Applied and Environmental Microbiology, 75 (8). 2304-2311 (2009)

The invention claimed is:

1. A method for fermenting pentose sugar comprising culturing a microorganism in a culture medium comprising pentose sugar(s) under conditions in which the pentose sugar(s) can be metabolized, wherein the microorganism has been transformed with a single expression construct(s) for i) the overexpression of native genes encoding xylulose kinase (XKS1), transaldolase (TAL1), transketolase 1 (TKL1) and transketolase 2 (TKL2) and ii) the expression of a functional heterologous gene encoding a xylose isomerase (XI), wherein the xylose isomerase (XI) gene is encoded by a nucleic acid sequence having at least 95% sequence identify to SEQ ID No 21, wherein the xylulose kinase (XKS1) is encoded by a nucleic acid sequence having at least 95% sequence identity to SEQ ID No 74, the transaldolase (TAL1) is encoded by a nucleic acid sequence having at least 95% sequence identity to SEQ ID No 77, the transketolase 1 (TKL1) is encoded by a nucleic acid sequence having at least 95% sequence identity to SEQ ID No 80 and the transketolase 2 (TKL2) is encoded by a nucleic acid sequence having at least 95% sequence identity to SEQ ID No 83, wherein the xylose isomerase (XI) gene is under the control of a constitutive promoter of *Saccharomyces cerevisiae;* wherein the pentose sugar is xylose; and wherein the microorganism is a yeast of the species *Saccharomyces cerevisiae.*

2. The method according to claim 1, wherein the culture medium comprises lignocellulosic biomass and/or a hydrolysate thereof.

3. The method according to claim 1, wherein the fermentation produces one or more compounds selected from the group consisting of ethanol, methanol, propanol, isopropanol, butanol, ethylene glycol, propylene glycol, 1,4-butanediol, glycerin, formic acid, acetic acid, propionic acid, butyric acid, valeric acid, caproic acid, palmitic acid, stearic acid, oxalic acid, malonic acid, succinic acid or succinate, glutaric acid, oleic acid, linoleic acid, glycolic acid, lactic acid or lactate, gamma-hydroxybutyric acid, 3-hydroxyalkanoic acid, alanine, methane, ethane, propane, pentane, n-hexane, pyruvate, aspartate, malate, valine and leucine.

4. The method according to claim 1, wherein the fermentation produces ethanol.

5. The method according to claim 1, wherein each of the genes encoding xylulose kinase (XKS1), transaldolase (TAL1), transketolase 1 (TKL1), transketolase 2 (TKL2) and xylose isomerase (XI) is under the control of a constitutive promoter, wherein the constitutive promoter is selected from TDH3 encoded by a nucleic acid sequence having at least 80% sequence identity to SEQ ID No 73, PGK1 encoded by a nucleic acid sequence having at least 80% sequence identity to SEQ ID No 76, CYC19 encoded by a nucleic acid sequence having at least 80% sequence identity to SEQ ID No 79, PFK1 encoded by a nucleic acid sequence having at least 80% sequence identity to SEQ ID No 82, truncated HXT7 encoded by a nucleic acid sequence having at least 80% sequence identity to SEQ ID No 90 and TEF encoded by a nucleic acid sequence having at least 80% sequence identity to SEQ ID No 85.

6. A method of using a microorganism, the method comprising fermenting pentose sugar(s) using the microorganism, wherein the microorganism has been transformed with a single expression construct(s) for i) the overexpression of the native genes for xylulose kinase (XKS1), transaldolase (TAL1), transketolase 1 (TKL1) and transketolase 2 (TKL2), and ii) the expression of a functional heterologous gene encoding a xylose isomerase (XI), wherein the xylose isomerase (XI) is encoded by a nucleic acid sequence having at least 95% sequence identity to SEQ ID No 21, wherein the xylulose kinase (XKS1) is encoded by a nucleic acid sequence having at least 95% sequence identity to SEQ ID No 74, the transaldolase (TAL1) is encoded by nucleic acid sequence having at least 95% sequence identity to SEQ ID No 77, the transketolase 1 (TKL1) is encoded by a nucleic acid sequence having at least 95% sequence identity to SEQ ID No 80 and the transketolase 2 (TKL2) is encoded by a nucleic acid sequence having at least 95% sequence identity to SEQ ID No 83, wherein the xylose isomerase (XI) gene is under the control of a constitutive promoter of *Saccharomyces cerevisiae;* wherein the pentose sugar is xylose; and wherein the microorganism is a yeast of the species *Saccharomyces cerevisiae.*

7. The method according to claim 6, wherein the method comprises producing ethanol from lignocellulosic biomass using the microorganism.

* * * * *